US010172361B2

(12) United States Patent
Gedanken et al.

(10) Patent No.: US 10,172,361 B2
(45) Date of Patent: Jan. 8, 2019

(54) DOPED METAL OXIDE NANOPARTICLES OF AND USES THEREOF

(71) Applicant: Bar-Ilan University, Ramat-Gan (IL)

(72) Inventors: Aharon Gedanken, Givataim (IL); Ehud Banin, Tel-Aviv (IL); Ilana Perelshtein, Rishon-LeZion (IL); Rachel Lubart, Tel-Aviv (IL); Anat Lipovsky, Kfar-Saba (IL); Eyal Malka, Yavne (IL); Nitzan Yeshayahu, Givat Shmuel (IL); Nina Perkas, Petach-Tikva (IL); Yakov Shalom, Lod (IL); Jonathan Lellouche, Ashdod (IL); Tal Patick, Givat Shmuel (IL); Michal Eshed, Yahud (IL); Livnat Naparstek, Hashmoniam (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 56 days.

(21) Appl. No.: 14/889,740

(22) PCT Filed: May 5, 2014

(86) PCT No.: PCT/IL2014/050406
§ 371 (c)(1),
(2) Date: Nov. 6, 2015

(87) PCT Pub. No.: WO2014/181329
PCT Pub. Date: Nov. 13, 2014

(65) Prior Publication Data
US 2016/0120184 A1 May 5, 2016

Related U.S. Application Data

(60) Provisional application No. 61/833,946, filed on Jun. 12, 2013, provisional application No. 61/819,661, filed on May 6, 2013.

(51) Int. Cl.
*A01N 59/20* (2006.01)
*B82Y 30/00* (2011.01)
*C30B 29/16* (2006.01)
*C30B 7/14* (2006.01)
*C30B 29/60* (2006.01)
*C30B 30/06* (2006.01)
*A61L 26/00* (2006.01)
*A61L 29/12* (2006.01)
*A61L 29/16* (2006.01)
*A61L 15/44* (2006.01)
*A01N 59/16* (2006.01)
*C01G 3/00* (2006.01)
(Continued)

(52) U.S. Cl.
CPC ............. *A01N 59/20* (2013.01); *A01N 59/16* (2013.01); *A61L 15/44* (2013.01); *A61L 26/0066* (2013.01); *A61L 26/0095* (2013.01); *A61L 29/123* (2013.01); *A61L 29/16* (2013.01); *B82Y 30/00* (2013.01); *C01F 5/02* (2013.01); *C01G 3/00* (2013.01); *C01G 9/00* (2013.01); *C01G 9/02* (2013.01); *C04B 35/053* (2013.01); *C04B 35/45* (2013.01); *C30B 7/14* (2013.01); *C30B 29/16* (2013.01); *C30B 29/60* (2013.01); *C30B 30/06* (2013.01); *A61L 2300/404* (2013.01); *A61L 2400/12* (2013.01); *C01P 2002/50* (2013.01); *C01P 2002/52* (2013.01); *C01P 2002/54* (2013.01); *C01P 2002/72* (2013.01); *C01P 2002/77* (2013.01); *C01P 2002/86* (2013.01); *C01P 2002/88* (2013.01); *C01P 2004/03* (2013.01); *C01P 2004/62* (2013.01); *C01P 2004/64* (2013.01); *C01P 2006/22* (2013.01); *C04B 2235/3206* (2013.01); *C04B 2235/3281* (2013.01); *C04B 2235/3284* (2013.01); *C04B 2235/5454* (2013.01)

(58) Field of Classification Search
CPC ........... A61L 2400/12; A61L 2300/404; A61L 29/16; A61L 15/44; A61L 26/0066; A61L 26/0095; A61L 29/123; A61L 2420/02; A61L 2430/02; A61L 27/32; A61L 27/56; A61L 31/086; A61L 15/46; A61L 2300/102; A61L 2300/106; A61L 29/106; A01N 59/16; A01N 59/20; A01N 25/10; A01N 25/34; A01N 25/08; A01N 37/28; A01N 31/16; A01N 55/00; A01N 59/10; A01N 63/02
See application file for complete search history.

(56) References Cited

FOREIGN PATENT DOCUMENTS

WO WO2004/076056 * 9/2004
WO WO2004076056 A2 9/2004

OTHER PUBLICATIONS

Xiong et al. "Sonochemical Synthesis of Highly Luminescent Zinc Oxide Nanoparticles Doped with Magnesium(II)", Angewandte Chemie, 2009, 121, 2765-2769, provided in IDS filed Mar. 28, 2016.*

(Continued)

Primary Examiner — Audrea B Coniglio
(74) Attorney, Agent, or Firm — Symbus Law Group, LLC; Clifford D. Hyra

(57) ABSTRACT

Nanoparticle composites comprised of a metal oxide and ions of a metallic element included within a crystal lattice of said metal oxide are disclosed. Process of preparing the nanoparticle composites per se and incorporated in or on a substrate are also disclosed. Uses of the nanoparticle composites and of substrates incorporating same, particularly for reducing a formation of a load of a microorganism or of a biofilm, are also disclosed.

20 Claims, 31 Drawing Sheets

(51) Int. Cl.
*C04B 35/053* (2006.01)
*C04B 35/45* (2006.01)
*C01G 9/00* (2006.01)
*C01G 9/02* (2006.01)
*C01F 5/02* (2006.01)

(56) References Cited

OTHER PUBLICATIONS

Xiong et al. ("Sonochemical Synthesis of Highly Luminescent Zinc Oxide Nanoparticles Doped with Magnesium(II)", Angew Chem Int Ed Eng, 48(15):2727-31, 2009).*
Ruby Chauhan et al., "Synthesis and characterization of copper doped ZnO nanoparticles" Dec. 2010.
Y. Arthoba Nayaka et al., "Structural and optical properties of Mg doped ZnO nanoparticles" Dec. 2012.
Xiong HM et al., "Sonochemical synthesis of highly luminescent zinc oxide nanoparticles doped with magnesium(II)". Dec. 2009.
Jun Geng et al., "Sonochecmical Synthesis of Er3+-Doped ZnO Nanospheres with Enhanced Upconversion Photoluminescence". Dec. 2012.
Ah Young Choi, Chul-Hee Han, "Comparison of doping limits among sonochemically prepared metal-doped TiO2 nanopowders in view of physicochemical properties" Jun. 2012.
ISR and WO as issued in PCT/IL2014/050406 dated Aug. 10, 2014.

* cited by examiner

Zeta Potential (mV)

Zeta Potential (mV)

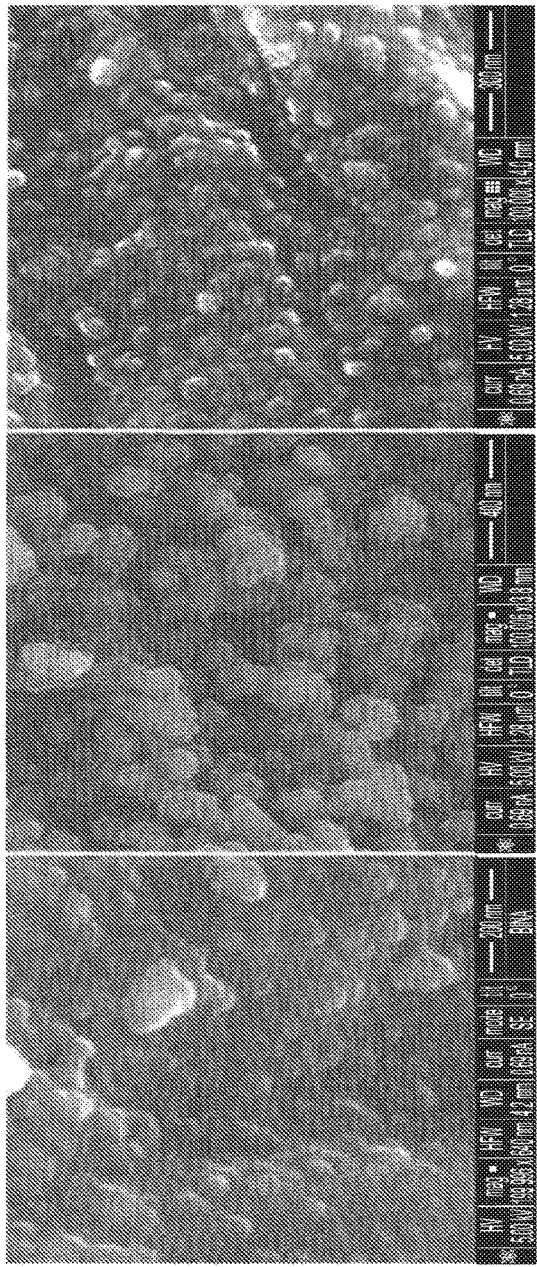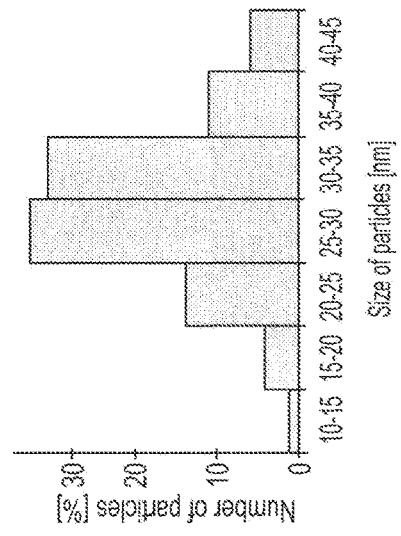
FIG. 7A  FIG. 7B  FIG. 7C  FIG. 7D

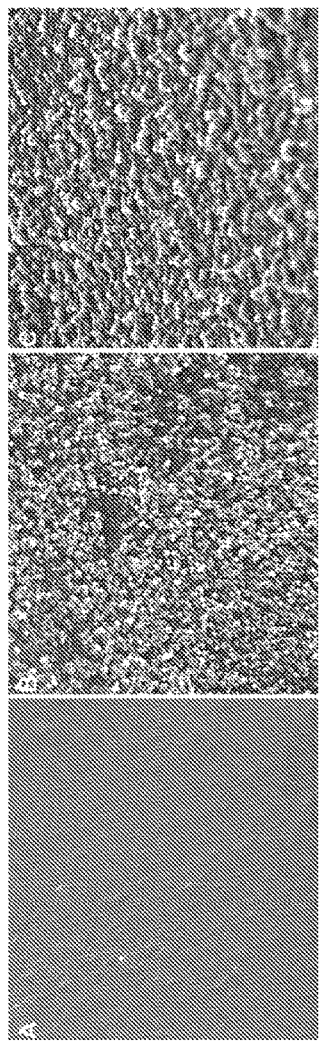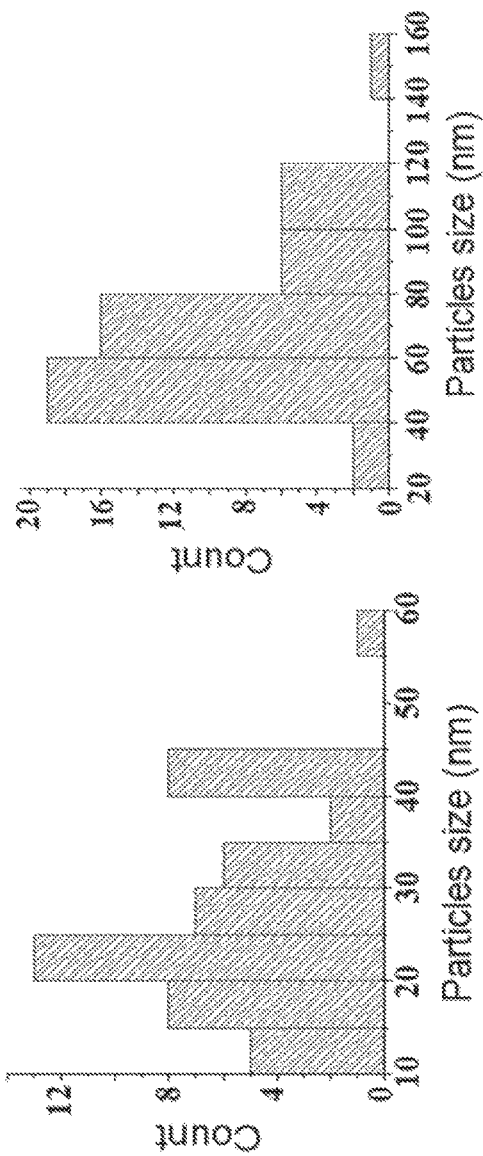

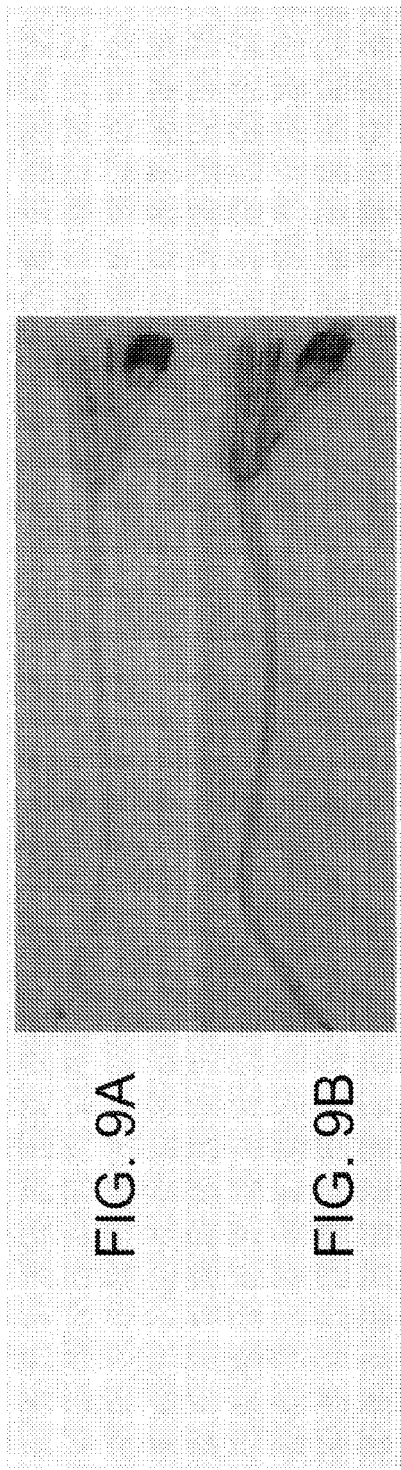
FIG. 9A
FIG. 9B
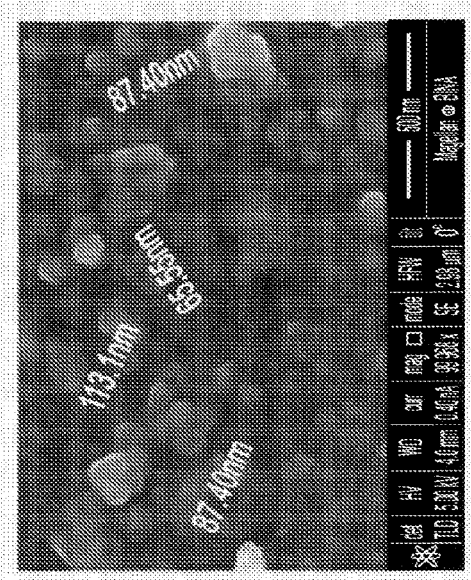
FIG. 10B
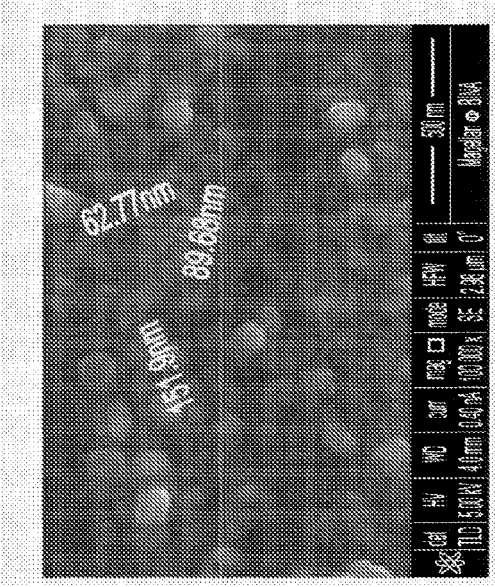
FIG. 10A

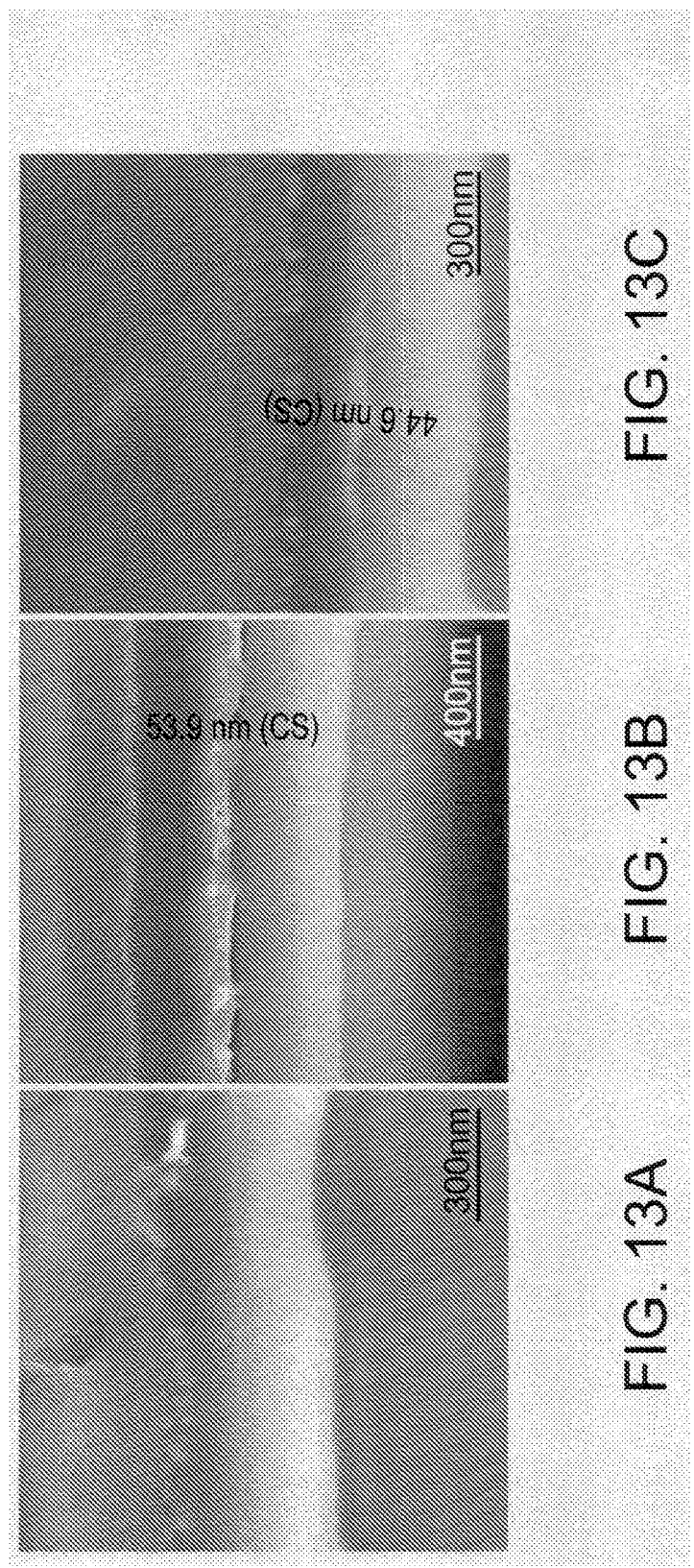

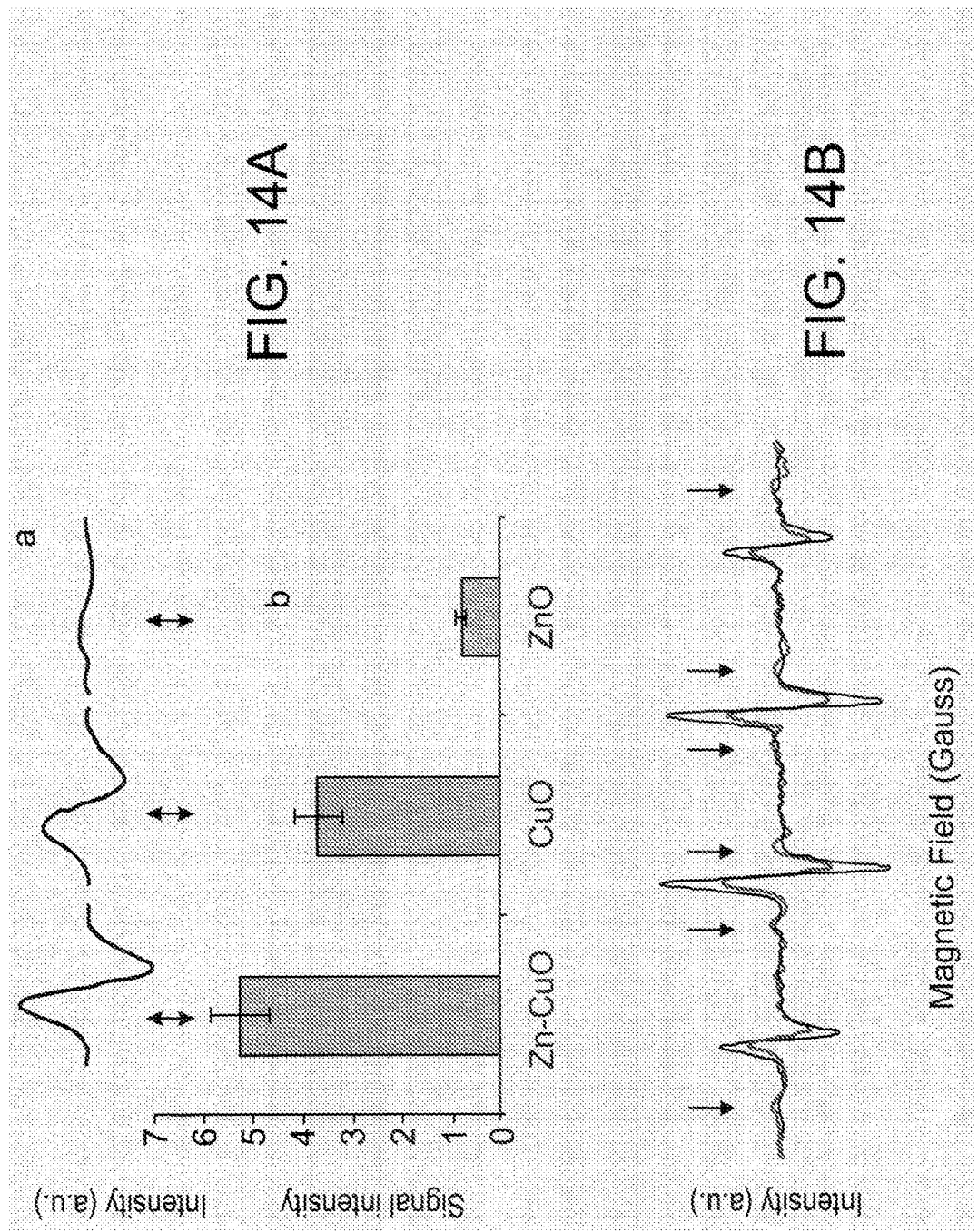

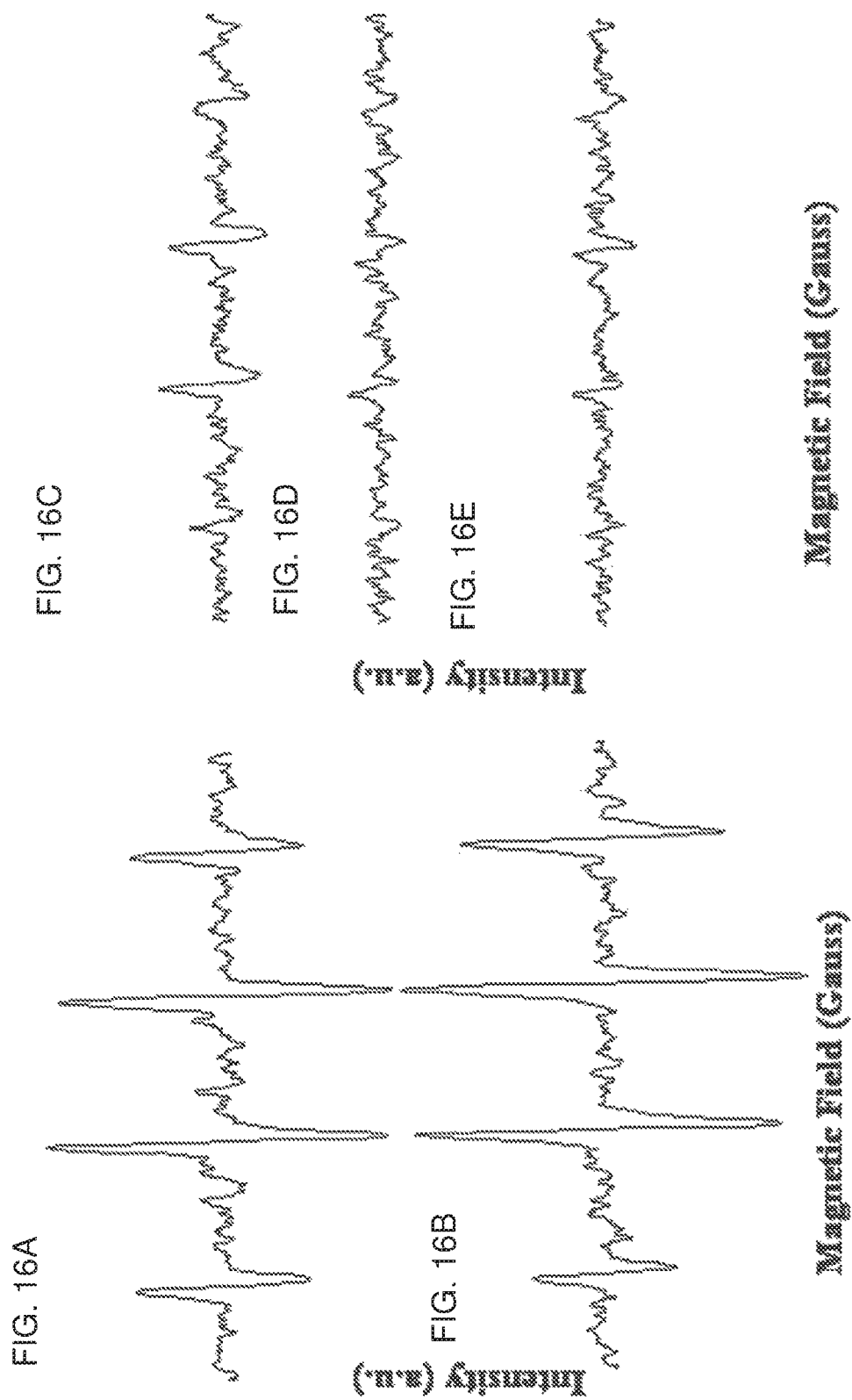

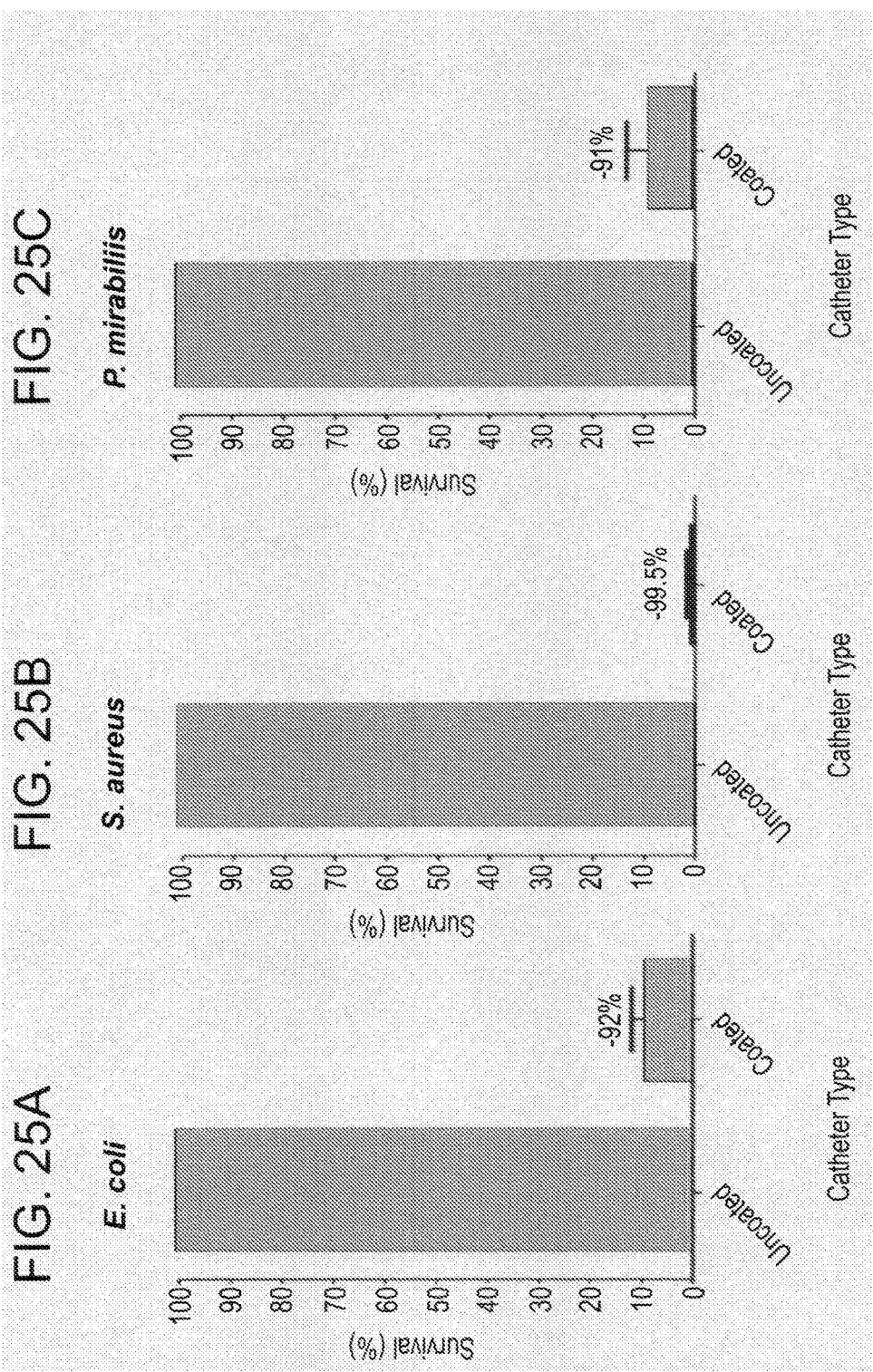

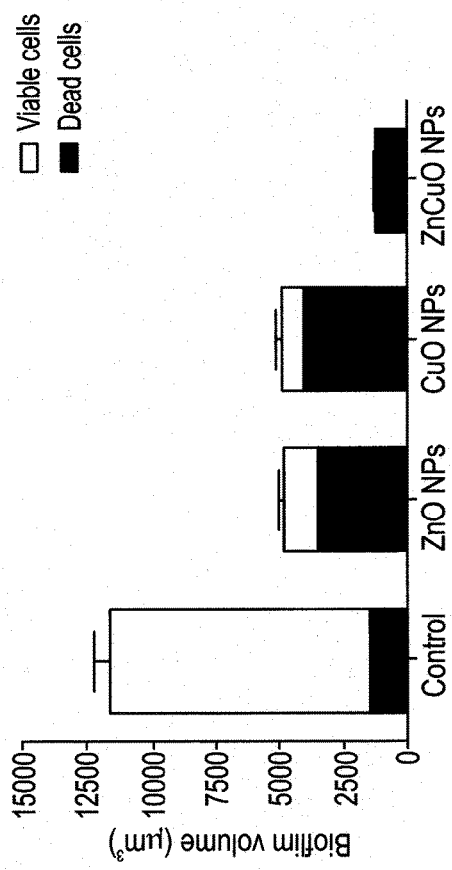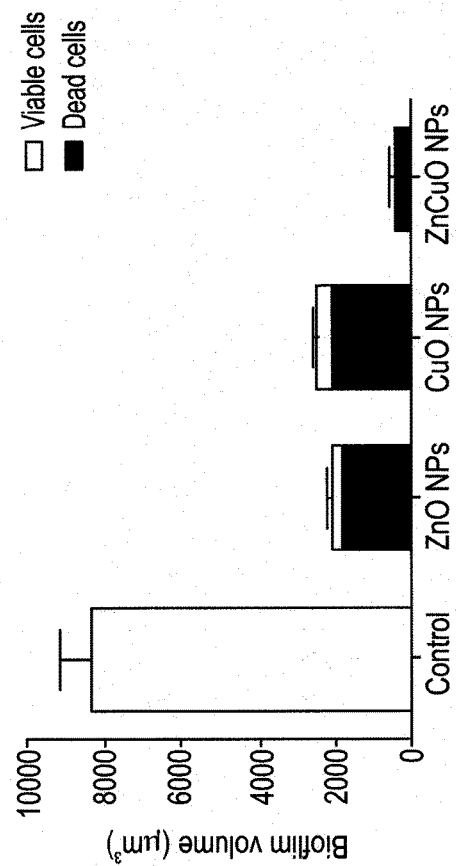

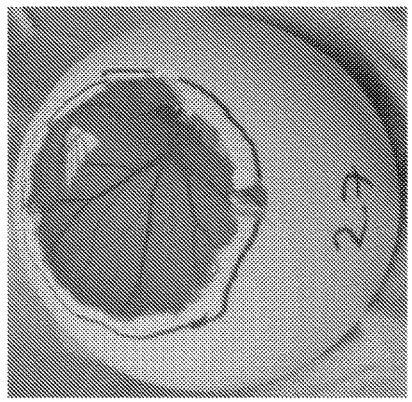
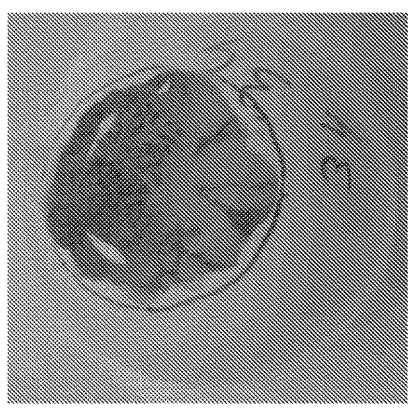
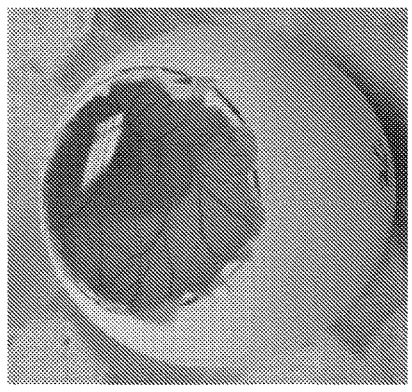
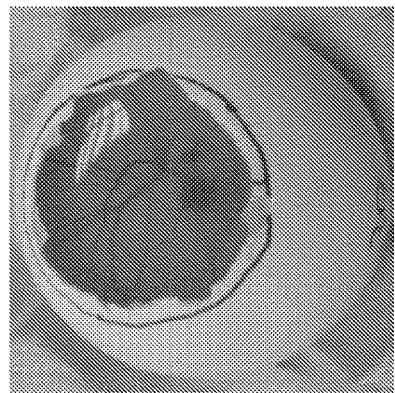
FIG. 29A
FIG. 29B
FIG. 29C
FIG. 29D

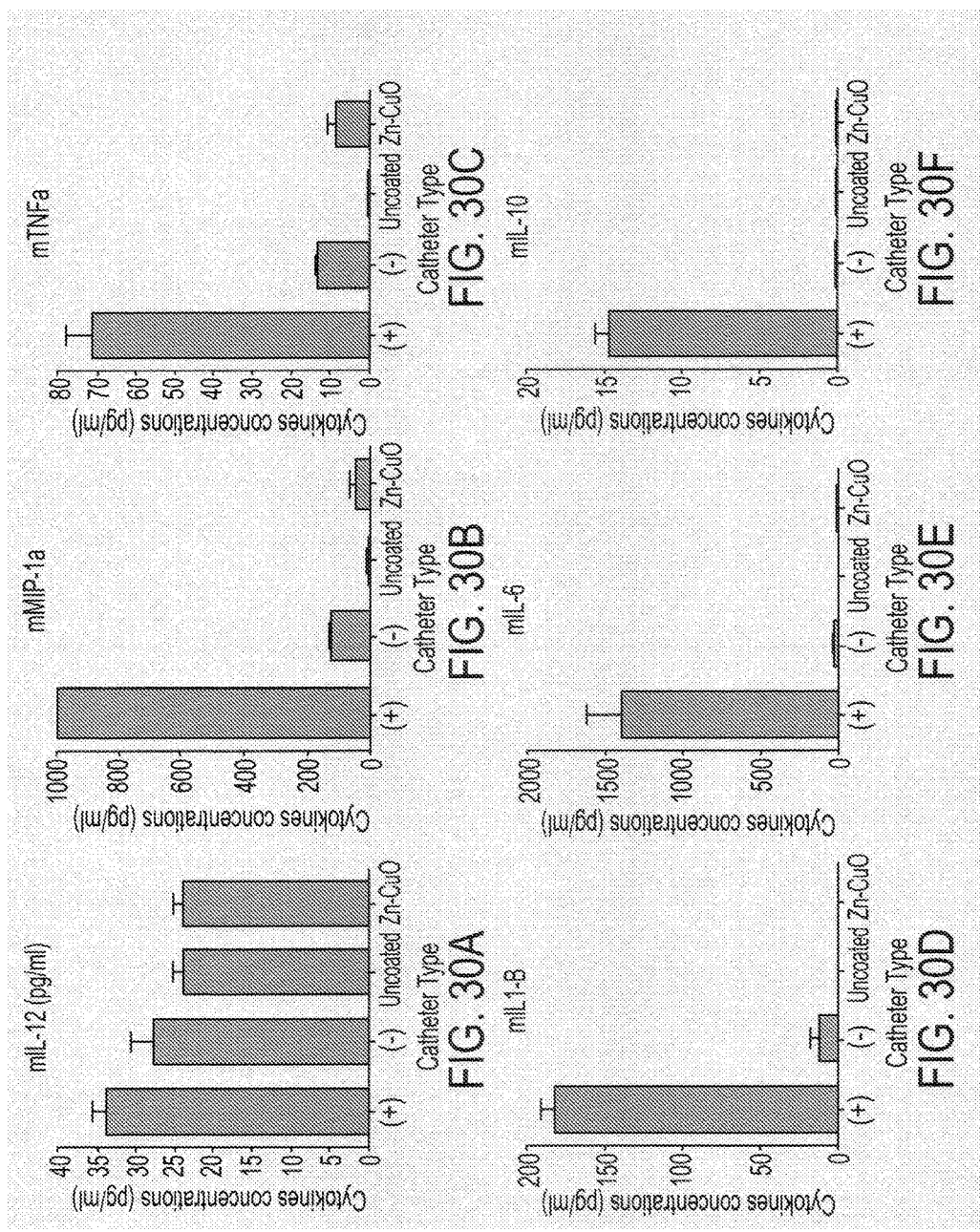

DOPED METAL OXIDE NANOPARTICLES OF AND USES THEREOF

FIELD AND BACKGROUND OF THE INVENTION

The present invention, in some embodiments thereof, relates to material science and, more particularly, but not exclusively, to doped metal oxide nanoparticles, processes of preparing same, surface coatings containing same and uses thereof in, for example, reducing or preventing growth of microorganisms.

Despite being successful in controlling or eliminating bacterial infections, widespread use of antibiotics both in human medicine and as a feed supplement in poultry and livestock production has led to drug resistance in many pathogenic bacteria (McCormick J. B., *Curr Opin Microbiol* 1:125-129, 1998). The evolution and spread of resistance genetic determinants, multidrug resistant (MDR) bacteria that cause life-threatening infections have been increasingly emerged (A. P. Magiorakos et al. *Clin. Microbiol. Infect.* 2012, 18, 268), and as such, the effectiveness of antibiotics has greatly diminished in the last decade. Furthermore, as resistance spreads among bacteria, there is great concern that antibiotics treatment will become increasingly less effective and, in some cases, completely ineffective.

Hospital-acquired (nosocomial) infections caused by antibiotic-resistant bacteria result in patient suffer and mortality and impose a substantial burden on the medical system due to extended periods of hospitalization. The economic impact of managing infections caused by nosocomial infections is substantial, and current costs are estimated to be more than $4 billion annually [Harrison and Lederberg (ed.), Antimicrobial resistance: issues and options. National Academy Press, Washington, D.C. pp. 1-7, 1998].

Bacterial attachment to surfaces leading to the formation of communities of bacterial cells is a major problem in many diverse settings. This sessile community of microorganisms, also termed a biofilm, is attached to an interface, or to each other, and embedded in an exopolymeric matrix. It manifests an altered growth rate and transcribes genes that free-living microorganisms do not transcribe. The most characteristic phenotype of the biofilm mode of growth is its inherent resistance to disinfection, antimicrobial treatment and immune response killing.

Medical implants and in-dwelling devices are especially prone to bacterial colonization and biofilm formation, and removal of the infected device is required in such cases due to the ineffectiveness of conventional antibiotic therapy against device-associated biofilm organisms. It has been estimated that the number of implant-associated infections approaches 1 million/year in the US alone, and their direct medical costs exceed $3 billion annually (R. O. Darouiche, Preventing infection in surgical implants, US Surgery, 2007, 40).

The inherent resistance of biofilms to killing and their pervasive involvement in implant-related infections has prompted research in the area of biocidal surfaces/coatings. Such anti-biofilm coatings may also be in use for various industrial applications such as drinking water distribution systems and food packaging.

Another class of difficult to eradicate microorganisms includes fungi. The number of antifungal agents is limited and most are non-specific as to the organism affected and can be detrimental to the environment, inducing toxicity to plant and animals. Inorganic metal oxides such as ZnO, MgO, and CuO are being increasingly used in antimicrobial applications. The key advantages of using inorganic oxides compared to organic antimicrobial agents are their stability, robustness, and long shelf-life.

Research in the area of nanometric metal oxides in general, and nanometric ZnO, MgO, and CuO in particular, has demonstrated a clear size dependence of various properties, such as, for example, electromagnetic, optical, and catalytic properties, as well as antibacterial activities (P. Madahi et al. *Phys. Scr.* 2011, 84; G. Applerot et al. *Adv. Funct. Mater.* 2009, 19, 842; G. Applerot et al. *Small* 2012, 8, 3326).

Oxygen is essential for most living organisms, but is also a precursor of reactive oxygen species (ROS), which can damage cellular components such as proteins, lipids and nucleic acids. ROS include oxygen-containing ions (e.g., superoxide; •$O^{2-}$), small molecules that contain peroxide (e.g., hydrogen peroxide; $H_2O_2$), free radicals (e.g., hydroxyls; •OH) and singlet oxygen (Droge et al. *Physiol. Rev.* 2002, 82:47-95; Lee et al. *Aust. J. Chem.* 2011, 64, 604).

During interaction with water, some metal oxides produce ROS that are known to kill bacteria (J. Sawai, et al. *J. Chem. Eng. Jpn.* 1996, 29, 627). The creation of ROS by metal oxides depends on the presence of defect sites in the structure of the metal oxide nanoparticles.

The rapid development of different methods for the fabrication and deposition of nanomaterials on polymer and glass surfaces significantly enhanced their application in electronic devices and biotechnology. Recently, some low temperature methods for the deposition nanoparticles on a glass substrate, such as, for example, electrode plating of spin-coated nanoparticles and deposition of nanoparticles on modified glass slides, were reported (K. H. Lee et al. *Langmuir*, 2007, 23, 1435).

Sonochemistry is concerned with the effect of ultrasonic irradiation on chemical systems. The chemical effects of ultrasonic irradiation arise from acoustic cavitation, namely, the formation, growth, and implosive collapse of bubbles in a liquid medium. The compression of the bubbles during cavitation is more rapid than the thermal transport, which generates short-lived, localized hotspot bubbles reaching temperatures as high as 5000 K, pressures of roughly 1000 Atm, and heating and cooling rates above $1 \times 10^{10}$ K/s (A. Gedanken, *Ultrason. Sonochem.*, 2004, 11 (2)).

Ultrasonic irradiation has been proven as an effective technique for the synthesis of nanomaterials (R. Gottesman, et al. *Langmuir* 2011, 27(2), 720). This technique further enables controlling the particle size of the product by varying the concentration of the precursors in the solution.

Ultrasonic irradiation has been proven as being effective for the deposition of nanoparticles on polymeric matrices since the high-velocity fluid agitation, shock waves and energetic jets that are created during the compression of the bubbles near a solid substrate, propel the newly-formed nanoparticles at the solid substrate at a very high speed (>100 m/s), which has been shown as being sufficient to embed the particles in the substrate (Y. Didenko and K. S. Suslick, *Nature*, 2002, 418, 394).

Utilizing sonochemistry as a coating route further enables combining the synthesis of various nanomaterials and their deposition on various substrates in a single operation without the aid of a binder. Previous works demonstrated the use of sonochemistry as a perspective method for coating various substrates such as paper (K. Ghule et al. *Green Chem.*, 2006, 8, 1034), glass surfaces (G. Applerot et al. *Appl. Surf. Sci.*, 2009, 256S, S3) and fabrics (I. Perelshtein et al. *ACS Appl. Mater. Interfaces*, 2009, 1 (2), 361) with ZnO nanoparticles.

U.S. patent application having Publication No. 2011/0097957 teaches a system for preparing antimicrobial fabrics, coated sonochemically with metal oxide nanoparticles to thereby form uniform deposition of the metal oxide.

P Madahi et al. [*Phys. Scr.* 2011, 84] teach that doping of ZnO with Mg or Sb leads to only a slight increase in the antibacterial activity of nanosized ZnO.

Prabhakaran et al. [*J. Cryst. Growth* 2003, 250, 77] teach the synthesis of a Zn-doped CuO composite and characterize it by chemo-physical properties such as its crystalline structure and magnetization as a function of temperature.

Huan-Ming et al. [*Angewandte Chemie International Edition* 2009, 48, 15, 2727] teach sonochemical synthesis of ZnO nanoparticles Doped with Mg. The Mg-doped ZnO nanoparticles exhibit bright, stable photoluminescence both in colloidal dispersions and in the solid state and are formed by doping Mg ions into ZnO nanoparticles by sonochemical synthesis. The preparation of Mg-doped ZnO is performed by applying sonication procedure on already synthesized ZnO nanoparticles in the presence of magnesium acetate.

Vidic et al. [J. Nanopart. Res. (2013) 15, 1595] teach the synthesis and physicochemical characterization of phase separated nanostructured of Zn-doped MgO, whose antibacterial activity was compared to its pure ZnO and MgO nanoparticles.

WO 2011/033040 teaches a method of preparing ZnO nanoparticles doped with Cu or Mg. WO 2011/033040 teaches that Cu-doped or Mg-doped ZnO nanoparticles have a higher antibacterial activity than ZnO nanoparticles.

SUMMARY OF THE INVENTION

The present inventors have surprisingly uncovered that doped metal oxide nanoparticles can be readily prepared, for example, by utilizing ultrasonic irradiation, both in solution and is and/or on a variety of substrates, and that such doped metal oxide nanoparticles exhibit exceptional, and even synergistic, antimicrobial and anti-biofouling activity, which exceeds that of non-doped metal oxide nanoparticles.

According to an aspect of some embodiments of the present invention there is provided a composition-of-matter comprising at least one nanoparticle composite, the at least one nanoparticle composite comprising a metal oxide and ions of a metallic element included in a crystal lattice of the metal oxide, wherein the metal oxide is selected from the group consisting of copper oxide and magnesium oxide and the metallic element is selected from the group consisting of zinc, copper and magnesium, and wherein the metallic element is different from the metal in the metal oxide.

According to some embodiments of the present invention, the metal oxide is copper oxide and the metallic element is zinc.

According to some embodiments of the present invention, the metal oxide is magnesium oxide and the metallic element is zinc.

According to some embodiments of the present invention, metal oxide is copper oxide and the metallic element is magnesium.

According to some embodiments of the present invention, an atomic ratio of the metal oxide and the ions of the metallic element in the at least one nanoparticle composite ranges from 10:1 to 4:1.

According to some embodiments of the present invention, the atomic ratio is about 8:1.

According to some of any of the embodiments of the present invention, the composition-of-matter is prepared by subjecting a mixture of a first and a second metal precursor to high intensity ultrasonic irradiation, wherein the first metal precursor forms the metal oxide and the second metal precursor comprises the metallic element.

According to some of any of the embodiments of the present invention, the composition-of-matter comprises a plurality of the nanoparticle composites.

According to some of any of the embodiments of the present invention, composition-of-matter is characterized by an X-Ray Powder Diffraction which is devoid of peaks at positions that correspond to a pristine metal oxide of the metallic element.

According to some of any of the embodiments of the present invention, the composition-of-matter is characterized by an X-Ray Powder Diffraction exhibiting at least one peak at a position and/or width that is different from a position and/or width of a corresponding peak in an X-Ray Powder Diffraction of the metal oxide.

According to some embodiments of the present invention, the position of the at least one peak is different from the position of the corresponding peak in the X-Ray Powder Diffraction of the metal oxide by at least 0.01°.

According to some of any of the embodiments of the present invention, the composition-of-matter is characterized by a crystal lattice exhibiting at least one cell parameter that is different from a corresponding cell parameter of a pristine crystal lattice of the metal oxide.

According to some embodiments of the present invention, the cell parameter is different from a corresponding cell parameter of a pristine crystal lattice of the metal oxide by at least 0.005.

According to an aspect of some embodiments of the present invention there is provided a composition-of-matter comprising at least one nanoparticle composite, the at least one nanoparticle composite comprising a metal oxide and ions of a metallic element included in a crystal lattice of the metal oxide, is the composition-of-matter being characterized by at least one of:

an X-Ray Powder Diffraction which is devoid of peaks at positions that correspond to a pristine metal oxide of the metallic element;

an X-Ray Powder Diffraction exhibiting at least one peak at a position and/or width that is different from a position and/or width of a corresponding peak in an X-Ray Powder Diffraction of the metal oxide; and a crystal lattice exhibiting at least one cell parameter that is different from a corresponding cell parameter of a pristine crystal lattice of the metal oxide.

According to some embodiments of the present invention, the position of the at least one peak is different from the position of the corresponding peak in the X-Ray Powder Diffraction of the metal oxide by at least 0.01°.

According to some embodiments of the present invention, the cell parameter is different from a corresponding cell parameter of the pristine crystal lattice of the metal oxide by at least 0.005.

According to some embodiments of the present invention, an atomic ratio of the metal oxide and the ions of the metallic element in the at least one nanoparticle composite ranges from 10:1 to 4:1.

According to some embodiments of the present invention, the atomic ratio is about 8:1.

According to some embodiments of the present invention, the metal oxide is selected from the group consisting of copper oxide, magnesium oxide, zinc oxide, calcium oxide, aluminum oxide, titanium oxide, gallium oxide and ferric oxide.

According to some embodiments of the present invention, the metallic element is selected from the group consisting of copper, zinc, magnesium, calcium, aluminum, titanium, ferrous, zirconium, hafnium, yttrium, and gallium.

According to some embodiments of the present invention, the composition-of-matter is prepared by subjecting a mixture of a first and a second metal precursor to high intensity ultrasonic irradiation, wherein the first metal precursor forms the metal oxide and the second metal precursor comprises the metallic element.

According to an aspect of some embodiments of the present invention there is provided a composition-of-matter comprising at least one nanoparticle composite, the at least one nanoparticle composite comprising a metal oxide and ions of a metallic element included in a crystal lattice of the metal oxide, as described in any of the embodiments herein, the composition-of-matter being prepared by subjecting a mixture of a first and a second metal precursor to high intensity ultrasonic irradiation, wherein the first metal precursor forms the metal oxide and the second metal precursor comprises the metallic element.

According to some of any of the embodiments of the present invention, the at least one nanocomposite structure is represented by the formula: $A_xB_yO$, wherein: A is the metallic element; B is a metal of the metal oxide; x and y are each independently a value of between 0.01 to 0.99, such that x+y=1.

According to some embodiments of the present invention, y is a value of from 0.8 to 0.9, X is a value from 0.1 to 0.2, wherein x and y are such that x+y=1, and the atomic ratio y/x ranges of from 20:1 to 4:1 or from 10:1 to 4:1.

According to some of any of the embodiments of the present invention, the composition-of-matter comprises a plurality of the nanoparticle composites, wherein an average diameter of the nanoparticle composites is less than about 300 nm.

According to some embodiments of the present invention, the average diameter is less than about 35 nm.

According to some of any of the embodiments of the present invention, the composition-of-matter further comprises a substrate, wherein a plurality of the nanoparticle composites is incorporated in and/or on at least a portion of the substrate.

According to some embodiments of the present invention, the substrate is or forms a part of an article.

According to some embodiments of the present invention, the article is selected from the group consisting of a medical device, a pharmaceutical, cosmetic or cosmeceutic product, a fabric, a bandage, a microelectronic device, a microelectromechanic device, a photovoltaic device, a microfluidic device, an article having a corrosivable surface, an agricultural device, a package, a sealing article, a fuel container and a construction element.

According to some embodiments of the present invention, the substrate comprises or is made of a polymer, a paper, a textile, wood, wool, leather, fur, a metal, carbon, a biopolymer and/or silicon, and the likes, as described herein.

According to some embodiments of the present invention, the substrate is a pharmaceutical, cosmetic or cosmeceutic product, and the nanoparticle composites are incorporated within the formulation.

According to an aspect of some embodiments of the present invention there is provided a process of preparing a composition-of-matter comprising at least one nanoparticle composite, the at least one nanoparticle composite comprising a metal oxide and ions of a metallic element included in a crystal lattice of the metal oxide, the process comprising subjecting a mixture of a first and a second metal precursor to high intensity ultrasonic irradiation, wherein the first metal precursor forms the metal oxide and the second metal precursor comprises the metallic element.

According to some embodiments of the present invention, the mixture further comprises an aqueous solution.

According to some embodiments of the present invention, the aqueous solution further comprises a water-miscible solvent.

According to some embodiments of the present invention, during the irradiation, the solution has a pH higher than 7.

According to some embodiments of the present invention, a molar ratio of the first and the second precursor ranges from 4:1 to 1:1.

According to some embodiments of the present invention, the molar ratio is about 3:1.

According to some embodiments of the present invention, a concentration of each of the first and second metal precursors in the aqueous solution independently ranges from 0.005M to 0.5M.

According to some embodiments of the present invention, each of the first and second metal precursors is independently a water-soluble salt of the metal of the metal oxide and the metallic element, respectively.

According to some embodiments of the present invention, the salt is independently selected from the group consisting of an acetate, a nitrate, and a chloride of the metal or the metallic element, respectively.

According to some embodiments of the present invention, the irradiation is carried out using ultrasonic waves at a frequency of at least 20 kHz.

According to some embodiments of the present invention, the irradiation is carried out using ultrasonic waves of at least 1 kW.

According to some embodiments of the present invention, the composition-of-matter further comprises a substrate and wherein a plurality of the nanoparticle composites is incorporated in and/or on at least a portion of the substrate, the process comprising contacting the substrate or a portion thereof with the mixture of the first and the metal precursors.

According to some embodiments of the present invention, the contacting is effected by immersing the substrate or a portion thereof in an aqueous solution which comprises the first and second metal precursors.

According to an aspect of some embodiments of the present invention there is provided a method of inhibiting or reducing the formation of load of a microorganism and/or the formation of a biofilm, in and/or on an article, the method comprising incorporating in and/or on the article with the composition-of-matter of any one of its respective embodiments.

According to some embodiments of the present invention, the article is selected from the group consisting of a medical device, a therapeutic, cosmetic or cosmeceutic product, a fabric, a bandage, a microelectronic device, a microelectromechanic device, a photovoltaic device, a microfluidic device, an article having a corrosivable surface, an agricultural device, a package, a sealing article, a fuel container and a construction element.

According to some embodiments of the present invention, the article is a medical device configured for topical application, and the microorganism is *P. Acne*.

According to an aspect of some embodiments of the present invention there is provided a pharmaceutical, cosmetic or cosmeceutic product, comprising any one of the compositions-of-matter described herein, incorporated in a pharmaceutical, cosmetic or cosmeceutical formulation forming the product.

According to some embodiments of the present invention, the formulation is in a form of a paste, a cream, a lotion, a foam, a gel, an emulsion, an ointment, a soap, a pladget, a swab, a suppository, a dressing, a solution, a mousse, a pad, a wipe, and a patch. According to some embodiments of the present invention, a plurality of the nanoparticle composites is dispersed in the formulations.

According to further embodiments of the present invention, the product is for use in treating medical, cosmetic or cosmeceutic conditions, optionally in combination with an active agent, as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-C present HR-SEM images of Zn-doped CuO nanoparticles' coating on a cotton fabric produced by the ultrasonic irradiation of copper acetate monohydrate and zinc acetate dehydrate precursors in concentrations of: 0.0075 M and 0.0025 M, respectively (referred to as "medium" or "med") (FIG. 7A); 0.015 M and 0.005 M, respectively (referred to as "high") (FIG. 7B); 0.00375 M and 0.00125 M, respectively (referred to as "low") (FIG. 7C).

FIG. 7D is a histogram showing the size distribution, as determined by "Scion image" software of the particles deposited on the coated fibers as obtained by the "medium" concentration.

FIGS. 8A-C present HR-SEM images demonstrating an artificial tooth having metal oxide nanoparticles coating, produced by the ultrasonic irradiation, applied thereon. FIG. 8A presents a reference image of a bare surface the artificial tooth. FIG. 8B presents an image of the tooth surface having a coating comprising Zn-doped CuO nanoparticles applied thereon. FIG. 8C presents an image of the tooth surface having a coating comprising CuO nanoparticles applied thereon.

FIGS. 8D-E present histograms showing the size distribution of the Zn-doped CuO (FIG. 8D) and non-doped CuO (FIG. 8E) nanoparticles applied on the coated artificial tooth.

FIGS. 9A-B present photographs showing an uncoated catheter (FIG. 9A) and a catheter coated with Zn-doped CuO nanoparticles by ultrasonic irradiation, according to some embodiments of the present invention (FIG. 9B).

FIGS. 10A-B present HR-SEM images showing a silicon urinary catheter having Zn-doped CuO nanoparticle coating deposited on the external surface of the catheter (FIG. 10A) and the internal surface of the catheter (FIG. 10B).

FIG. 11A shows the analysis of a bare tooth surface. FIG. 11B shows the analysis of tooth surface having Zn-doped CuO nanoparticles coating deposited thereon by the sonochemical method, with the arrow marking a peak indicative of the presence of elemental Cu. FIG. 11C shows the analysis of tooth surface having CuO nanoparticles coating deposited thereon by the sonochemical method, with the arrow marking a peak indicative of the presence of elemental Cu.

FIGS. 13A-C present FIB-SEM images of an uncoated tooth (control; FIG. 13A), a tooth coated with Zn-doped CuO nanoparticles by the sonochemical method (FIG. 13B), and a tooth coated with CuO nanoparticles by the sonochemical method, with the red markings indicating the thickness of the coating.

FIGS. 14A-B present a bar graph (b) showing the relative intensity correlated to the integrate area of ESR signals (a) originating from aqueous suspensions of Zn-doped CuO, CuO and ZnO as detected by DMPO spin adduct (FIG. 14A); and ESR spectra of Zn-doped CuO before (the spectrum showing stronger quartet signal) and after (the spectrum showing weaker quartet signal) a further addition of DMSO to a Zn-doped CuO- and DMPO containing suspension, with the arrows marking the features of the spectrum corresponding to the DMPO-CH$_3$ spin adduct.

FIGS. 16A-E present ESR spectra corresponding to the signal of the DMPO-OH spin adduct originating from an aqueous suspension of: Zn-doped CuO nanoparticles (FIG. 16A), Zn-doped CuO nanoparticles upon being heated at 300° C. under air (FIG. 16B), Zn-doped CuO nanoparticles upon being heated at 550° C. under air (FIG. 16C), Zn-doped CuO nanoparticles upon being heated at 550° C. under nitrogen (FIG. 16D). FIG. 16E shows the ESR signal of DMPO solution, for a reference.

FIGS. 25A-C are bar graphs showing the bacterial survival % upon contacting a silicon urinary catheter coated with Zn-doped CuO nanoparticles with *E. coli* (FIG. 25A), *S. aureus* (FIG. 25B), *P. mirabilliis* (FIG. 25C) (error bars represent standard deviation of uncertainty).

FIGS. 26A-B are bar graphs presenting the biofilm volume of *E. coli* (FIG. 26A) and *S. aureus* (FIG. 26B) formed on uncoated glass substrate (control) and on glass substrates coated with either ZnO nanoparticles, CuO nanoparticles or Zn-doped CuO nanoparticles (error bars represent standard deviation of uncertainty).

FIGS. 29A-D present photographs of the hen's egg test chorioalantoic membrane (HET-CAM) blood vessels following irritation tests with saline (FIG. 29A), or with NaOH (0.1M) (FIG. 29B), and of extracts of uncoated catheter (FIG. 29C), and of a catheter coated with Zn-doped CuO (FIG. 29D).

FIGS. 30A-F are bar graphs presenting the effect of saline (negative control) lipopolysaccharides (LPS) (positive control) and extracts of: uncoated catheter and Zn-doped CuO coated catheter on the inducement of the following cytokine in mouse: IL-12 (FIG. 30A), MIP-1-α (FIG. 30B) TNF-α (FIG. 30C), IL-1-β (FIG. 30D), IL-6 (FIG. 30E), IL-10 (FIG. 30F), as assessed in a supernatant of spleen cells following 22 hours of incubation.

DESCRIPTION OF SPECIFIC EMBODIMENTS OF THE INVENTION

Figure 1:
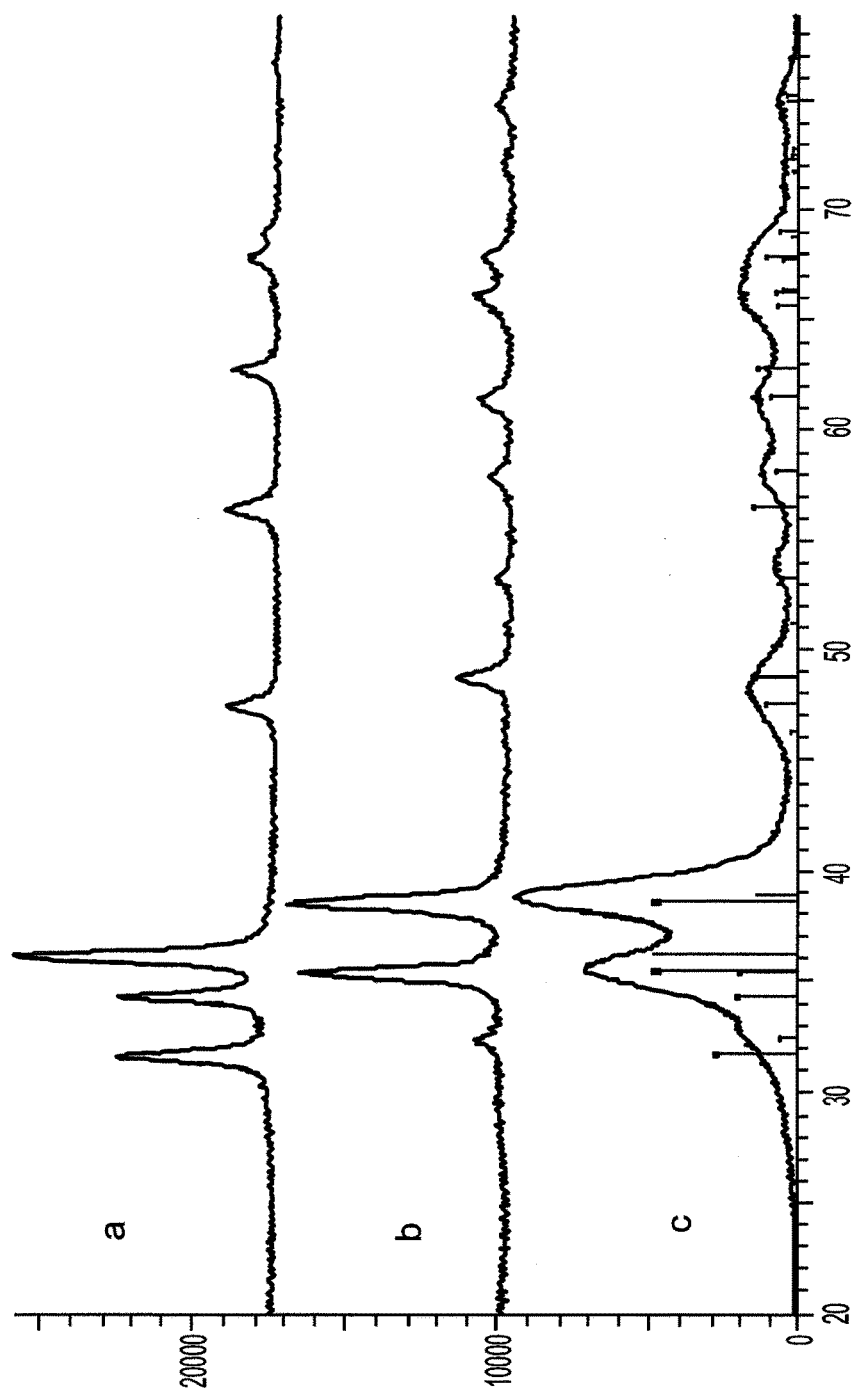
FIG. 1 presents comparative spectra of X-Ray diffraction pattern of sonochemically prepared ZnO nanoparticles (spectrum a), CuO nanoparticles (spectrum b) and Zn-doped CuO nanoparticles (3:1 Cu:Zn precursors molar ratio) according to some embodiments of the present invention (spectrum c).

The present invention, in some embodiments thereof, relates to material science and, more particularly, but not exclusively, to doped metal oxide nanoparticles, processes of preparing same, surface coatings containing same and uses thereof in, for example, reducing or preventing growth of microorganisms.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have contemplated that doping metal oxide nanoparticles with a metallic element would impart, modulate or enhance the anti-microbial activity of the metal oxide nanoparticles.

While reducing the present invention to practice, the present inventors have utilized an ultrasonic irradiation methodology both for the synthesis of the doped metal oxide nanoparticles and for incorporation of the doped metal oxide nanoparticles onto/into various substrates.

As demonstrated in the Examples section that follows, the present inventors have shown that metallic element was successfully doped in the crystal lattice of the metal oxide nanoparticles, when metal precursors of the metallic element and the metal oxide were used at certain molar ratios, and when a sonochemical (high intensity ultrasonic irradiation) methodology was used for their preparation. The present inventors have also shown that the doped metal oxide nanoparticles exhibited improved antimicrobial and/or anti-biofilm activities, compared to corresponding pristine (non-doped) metal oxide nanoparticles.

The present inventors have also shown that several substrates can be coated with the doped metal oxide nanoparticles, thereby imparting to the coated substrates the antimicrobial and/or antibiofilm activities.

Embodiments of the present invention therefore relate to nanoparticle composites comprising a metal oxide and ions of a metallic element included in a crystal lattice of the metal oxide, and to compositions-of-matter comprising said nanoparticle composites.

The Compositions-of-Matter:

According to an aspect of some embodiments of the present invention there is provided a composition-of-matter comprising at least one nanoparticle composite which comprises a metal oxide and ions of a metallic element included in a crystal lattice of said metal oxide.

Hereinthroughout, the terms "nanoparticle" or "nanoparticle composite", which are used herein interchangeably, describe a particle featuring a size of at least one dimension thereof (e.g., diameter, length) that ranges from about 1 nanometer to 1000 nanometers.

In some embodiments, the size of the particle described herein represents an average size of a plurality of nanoparticle composites or nanoparticles.

In some embodiments, the average size (e.g., diameter, length) ranges from about 1 nanometer to 500 nanometers. In some embodiments, the average size ranges from about 1 nanometer to about 300 nanometers. In some embodiments, the average size ranges from about 1 nanometer to about 200 nanometers. In some embodiments, the average size ranges from about 1 nanometer to about 100 nanometers. In some embodiments, the average size ranges from about 1 nanometer to 50 nanometers, and in some embodiments, it is lower than 35 nm.

In some embodiments, the average size is about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 40 nm, about 42 nm, about 44 nm, about 46 nm, about 48 nm, or 50 nm, including any value therebetween.

The particle can be generally shaped as a sphere, a rod, a cylinder, a ribbon, a sponge, and any other shape, or can be in a form of a cluster of any of these shapes, or can comprises a mixture of one or more shapes.

In some embodiments, the composition-of-matter comprises a plurality of nanoparticles, and at least 10%, 20%, 30%, 40%, 50%, 60%, 70%, 80%, 90%, 95%, 98%, 99%, 99.9%, or all of the nanoparticles are nanoparticle composites as described herein, e.g., in shape and average size.

In some embodiments, at least some, and in some embodiments, most of the nanoparticles or nanoparticle composites are generally shaped as spheres.

In some embodiments, the plurality of nanoparticle composites comprises nanoparticle composites which are the same or different, preferably at least 50%, 60%, 70%, 80%, 90%, 95%, 98%, 99%, 99.9%, or all of the nanoparticle composites are the same.

The term "composite", is used herein to denote that the nanoparticles are made of at least two components, namely, made of non-pristine substances. It is noted that nanoparticles as described herein, which are doped metal oxide nanoparticles, are also referred to herein simply as doped nanoparticles.

The Metal Oxide:

Hereinthroughout, the term "metal oxide" describes natural, isolated and/or synthetically prepared metal oxide substances.

A metal oxide comprises one or more metal atoms and one or more oxygen atoms, wherein one or more of the metal atom(s) is in association with one or more oxygen atoms as further defined and discussed hereinafter. In some embodiments, the metal atoms and the oxygen atoms are joined together via ionic bonds, such that cations of the metal atoms are associated with oxygen anions.

In some embodiments, the metal oxides include, without limitation, oxides of alkali metals, alkaline earth metals, lanthanides, actinides, transition metals, metalloids, or any other metals. The metal oxide can include an oxide:metal atomic ratio ranging from 4:1 to 1:1.

Exemplary metal oxides include, without limitation, oxides of magnesium, titanium, aluminum, zirconium, calcium, scandium, vanadium, chromium, manganese, ferrite, cobalt, nickel, copper and zinc, and more preferably metal oxides of copper, zinc, magnesium, titanium, zirconium, aluminum, and calcium.

In some embodiments, for any of the aspects described herein, the metal oxide is of a divalent metal, and can be represented as "BO", which B being a metal atom capable of forming a BO metal oxide.

In some embodiments, the metal oxide is CuO, MgO or ZnO.

In some embodiments, the metal oxide is CuO or MgO.

In some embodiments, the metal oxide is CuO.

Crystal Lattice:

As used herein and in the art a crystal lattice is unique periodic and systematic arrangement of atoms or ions found in a crystal in an ordered structure, and is represented by three-dimensional configuration of points connected by lines used to describe the orderly arrangement of the atoms or ions in a crystal. Each point represents one or more atoms in the actual crystal. The lattice is divided into a number of identical blocks, or unit cells, that are repeated in all directions to form a geometric pattern. Lattices are typically classified according to their dominant symmetries: isometric, trigonal, hexagonal, tetragonal, orthorhombic, monoclinic, and triclinic.

As used herein and in the art the unit cell is the smallest component of the crystal lattice and describes the 3D arrangement of atoms in a crystal.

The unit cell is represented in terms of its lattice parameters which are the lengths of the cell edges (a, b and c) and the angles between them (alpha, beta and gamma), while the positions of the atoms inside the unit cell are described by the set of atomic positions $(x_i, y_i, z_i)$ measured from a lattice point.

X-ray Powder Diffraction (XRPD) is typically used to determine the crystal arrangement of a crystal lattice.

For example, X-ray powder diffraction patterns can be measured with an X-ray diffractometer Cu $K_\alpha$ or Cr $K_\alpha$ radiation by standard methods described, for example, by B. D. Cullity and S. R. Stock (Elements of X-ray Diffraction, 3rd ed., New York: Prentice Hall, 2001). The unit cell parameters can be determined by Rietveld refinement of the powder diffraction data. The X-ray crystalline size also can be determined by analysis of peak shifting or peak broadening in a powder diffraction pattern of a sample containing an internal Si standard using the single-peak Scherrer method or the Warren-Averbach method as discussed in detail, for example, by H. P. Klug and L. E. Alexander (X-ray Diffraction Procedures for Polycrystalline and Amorphous Materials, New York: Wiley, 1974, 618-694).

As used herein the term "defect" or grammatical diversions thereof, when related to crystal lattice, relates to crystals featuring crystallographic irregularities compared to an ideal arrangement of the components forming the crystal. Defects as known in the art, include but not limited to: point defects, which include but are not limited to: vacancy defects, interstitial defects, Frenkel defect, substitutional defect, antisite defects, topological defects, line defects which include but are not limited to: dislocations, planar defects and bulk defects.

A "defect" in the crystal lattice can be induced by doping, as described herein.

The Metallic Element:

As discussed herein, a nanoparticle composite as described in any one of the embodiments herein, includes a metal oxide and a metallic element included in a crystal lattice of the metal oxide, wherein the metallic element is different from the metal in the metal oxide.

In some embodiments, atoms of the metallic element are introduced into the crystal lattice of the metal oxide, and, in some embodiments, atoms (e.g., as positive ions) of the metallic element replace some of the atoms of the metal oxide (e.g., ions of the metal in the metal oxide).

The inclusion of such metallic elements in the crystal lattice of the metal oxide is also referred to herein and in the art as "doping", with the metallic element referred to as "dopant". The nanoparticle composite formed upon inclusion of ions of a different metallic element is also referred to herein and in the art as "crystal lattice-doped metal oxide" or simply as "doped metal oxide".

Metal-doped, non-metal doped, and un-doped metal oxides can be characterized by measurement of their X-ray powder diffraction patterns, elemental compositions, and average particle sizes. In some embodiments, crystal lattice parameters of doped or un-doped (pristine) metal oxide nanoparticles can be determined from powder X-ray diffraction ("XRPD") patterns.

In some of any of the embodiments described herein, the metallic element, or dopant, in the nanoparticle composites as described herein, can be, for example, and without limitation, magnesium, copper, zinc, titanium, aluminum, scandium, vanadium, chromium, manganese, ferrous, cobalt, nickel, and any combination of the foregoing, and in some embodiments, can be, for example, copper, zinc, magnesium, titanium, zirconium, aluminum, hafnium, calcium and any combination thereof.

In some embodiments, the metallic element is copper, zinc, and/or magnesium.

The above described metallic elements can be used in any combination with any one of the exemplary metal oxides delineated hereinabove.

In some embodiments, the atomic ratio of the metal oxide and the metallic element in the crystal-lattice doped metal oxide ranges from 50:1 to 1:10, or from 10:1 to 1:10, or from 10:1 to 1:5, or from 10:1 to 1:1, or from 10:1 to 2:1, or from 10:1 to 3:1 or from 10:1 to 4:1, or from 10:1 to 5:1.

In some embodiments the atomic ratio is about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1, including any value therebetween.

In some embodiments, the atomic ratio of the metal oxide and the metallic element in the crystal-lattice doped metal oxide ranges from 10:1 to 4:1 or from 10:1 to 5:1, and can be, for example, 10:1, 9:1, 8:1, 7:1, 6:1, 5:1 or 4:1, including any value therebetween.

In some embodiments, the atomic ratio is about 8:1.

The terms "stoichiometric ratio", "atomic ratio", and "molar ratio" are used herein interchangeably in the context of a crystal lattice-doped metal oxide and refer to the ratio between the number of atoms of the dopant (metallic element) and the number of atoms of the metal of the metal oxide, in the crystal lattice, as defined herein.

In some embodiments, a doped metal oxide as described in any of the embodiments herein is represented by the Formula:

$$A_xB_yO$$

wherein A is a metallic element (dopant, as described in any one of the respective embodiments), B is the metal of the metal oxide, according to any one of the respective embodiments, x and y are independently a value of between 0.01 to 0.99, such that x+y=1.

In some embodiments, x and y in the Formula are such that y/x represents the atomic ratio of the metal oxide to metallic element, as described herein.

In some embodiments, the y/x ratio ranges from 100:1 to 1:1, or from 100:1 to 2:1, or from 100:1 to 3:1, or from 100:1 to 4:1, or from 50:1 to 4:1, or from 40:1 to 4:1, or from 30:1 to 4:1, or from 20:1 to 4:1, or from 15:1 to 4:1 or from 10:1 to 4:1.

In some embodiments, x ranges from 0.2 to 0.1 and y ranges from 0.8 to 0.9, and the y/x ratio ranges from 20:1 to 4:1 or from 10:1 to 4:1.

Thus, for example, in some embodiments, y is 0.9 and x is 0.1; or y is 0.89, or 0.88, or 0.87, or 0.86, or 0.85, or 0.84, or 0.83, or 0.82, or 0.81, or 0.80, and x is 0.11, 0.12, 0.13, 0.14, 0.15, 0.16, 0.17, 0.18 or 0.19 or 0.20, respectively.

In some embodiments, y is 0.88 and x is about 0.11.

In some embodiments, y/x is about 8:1.

In some of the of the embodiments described herein, the atomic (stoichiometric) ratio between the metal of the metal oxide lattice and the metallic element doped in the crystal lattice of the metal oxide is determined by inductively coupled plasma (ICP).

Crystallographic Characteristics:

XRPD measurements of crystal lattice-doped substances such as metal oxides typically show a shift in the position of refraction angle peaks compared to pristine, non-doped metal oxide. These measurements are also indicative of a formation of a biphasic mixture of different metal oxides, in cases where doping is not effected. A detailed discussion is presented in the Examples section that follows.

Figure 2A:
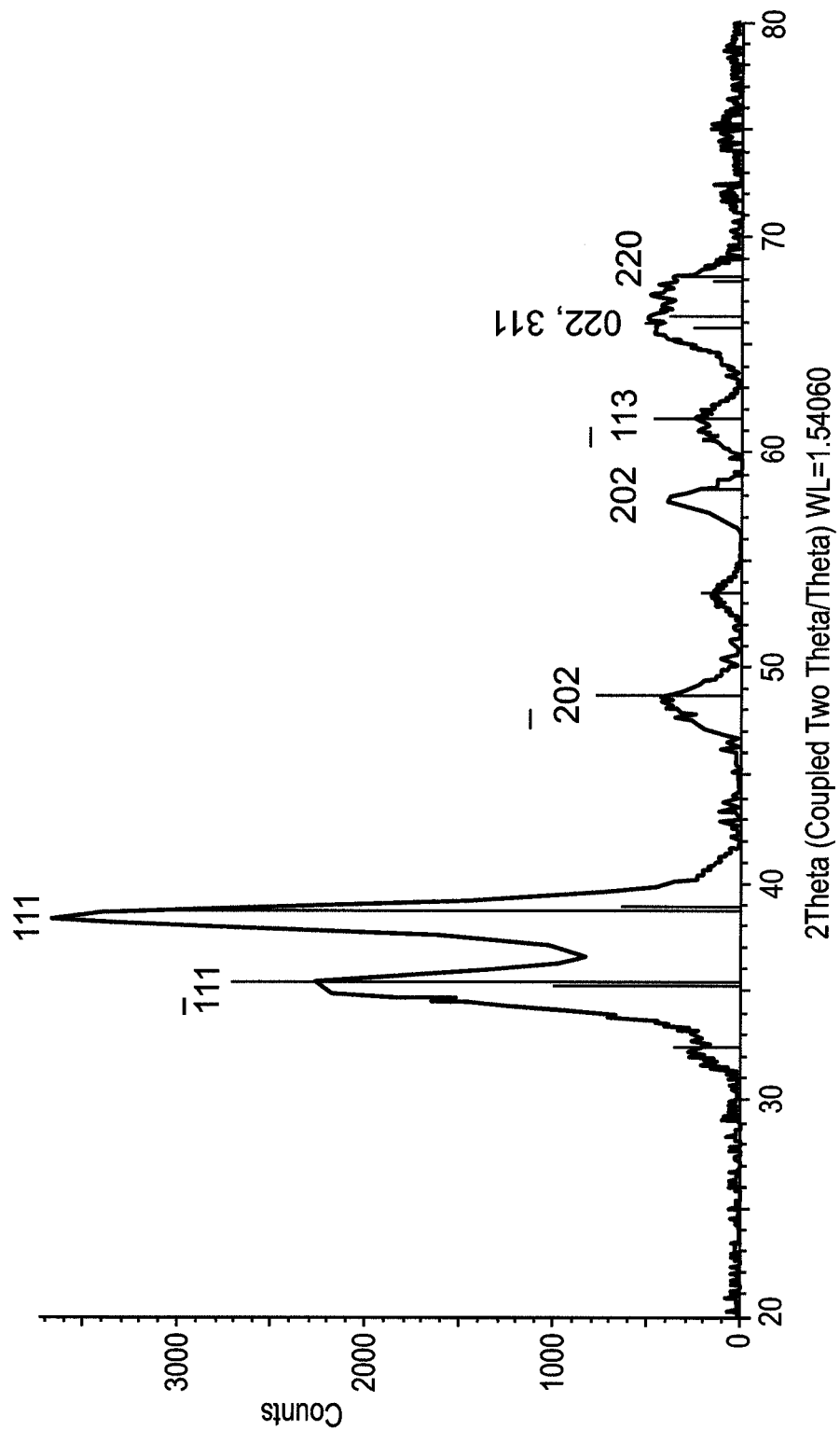
FIGS. 2A-D present X-Ray diffraction patterns of the product obtained from a mid-3:1 Cu:Zn precursors mixture by applying ultrasonic irradiation (FIG. 2A); of the product obtained from a 3:1 Cu:Zn precursors mixture upon application of microwave irradiation (FIG. 2B), application of thermal reaction (FIG. 2C); and of the product obtained from a 4:1 Cu:Zn precursors mixture by applying ultrasonic irradiation (FIG. 2D). The sharp lines present standard values of reflection lines of CuO in FIGS. 2A-C and of CuO and ZnO in FIG. 2D.

FIG. 2A, for example, presents representative XRD reflection lines of a product obtained from med-3:1Cu:Zn precursors mixture as designated hereinthroughout, subjected to ultrasonic irradiation, showing that the pattern of the product (spectrum) is shifted in comparison to the monoclinic CuO (lines, international powder diffraction file (PDF) (80-1916).

In some of any one of the embodiments described herein, a composition-of-matter as described herein, comprises at least one nanoparticle composite which is a crystal lattice-doped metal oxide, as described in any one of the respective embodiments herein, and the composition-of-matter and/or the nanoparticle composite (or a plurality of nanoparticle composites) is characterized by at least one of:

an X-Ray Powder Diffraction which is devoid of peaks at positions that correspond to a pristine metal oxide of the metallic element;

an X-Ray Powder Diffraction exhibiting at least one peak at a position and/or width that is different from a position and/or width of a corresponding peak in an X-Ray Powder Diffraction of a pristine crystal lattice of the metal oxide; and a crystal lattice exhibiting at least one cell parameter that is different from a corresponding cell parameter of a pristine crystal lattice of the metal oxide.

Hereinthroughout, "peak position" refers to the reflection peaks along the 2θ refractive angle axis in a XRPD spectrum, and refers to the peak position at any peak intensity. The peak position is denoted by the 2 theta angle.

By "devoid of peaks at positions that correspond to a pristine metal oxide of the metallic element" it is meant that an XRPD pattern of the composition-of-matter or of the nanoparticle composites comprised therein do not include peaks in intensity higher than 100 counts, or higher than 50 counts, which correspond to e.g., international standard values of XRPD pattern of a metal oxide of the metallic element. That is, the nanoparticle composite is characterized as devoid of a metal oxide of the metallic element. By "devoid of" in this regard it is meant no more than 1%, or no more than 0.1%, or no more than 0.01% of the metal oxide of the metallic element, by weight.

In some embodiments, XRPD measurements or XRD measurements of a composition-of-mater or of a plurality of nanoparticle composites as described herein exhibits a shift at a peak position of at least one peak with respect to the peak positions of a pristine (non-doped) metal oxide. In some embodiments, a shift is observed in at least one, at least 2, at least 3, at least 4, at least 5, etc. or in all of the peak positions, with respect to the peak positions of pristine metal oxide.

In some embodiments, a shift in the one or more peak positions is of at least 0.01°, and can be, for example, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5°, and even more. The shift can be the same or different in size and direction, for each peak position which is shifted.

In some embodiments, XRPD measurements or XRD measurements of a composition-of-mater or of a plurality of nanoparticle composites as described herein exhibits a different peak width of at least one peak with respect to the width of corresponding peaks at corresponding positions of a pristine (non-doped) metal oxide. In some embodiments, a different peak width is observed in at least one, at least 2, at least 3, at least 4, at least 5, etc. or in all of the peak positions, with respect to the peak positions of pristine metal oxide.

In some embodiments, a change is peak width is measured by a change in the full width at half maximum (FWHM) of the peak.

In some embodiments, the full width at half maximum (FWHM) of the peak in the one or more peak positions is broadened with respect to corresponding peaks of a pristine metal oxide by at least 5%, at least 10%, and can be for example, 11%, 12%, 13%, 14%, 15%, 16%, 17%, 18%, 19%, 20%, 25%, 30%.

In some embodiments, both shift in peak position and broadening of peak width is observed in one or all of the peaks, with respect to the peaks of a pristine metal oxide.

In some embodiments, a difference in the cell parameter can be a difference of any one or all of the parameters a, b and c of a cell unit, as measured by XRD measurements.

In some embodiments, one or all of the cell parameters is different from the corresponding cell parameter of the crystal lattice of a corresponding pristine metal oxide by at least 0.001, or by at least 0.005, 0.008, 0.009, 0.01, 0.02, 0.03, 0.04, 0.05, 0.06, 0.07, 0.08, 0.09, 0.1, 0.2, 0.3, 0.4, 0.5, or higher values.

In some embodiments, all of the above characteristics are exhibited by the composition-of-matter or by a nanoparticle composite or a plurality thereof, as described herein.

Exemplary Compositions-of-Matter:

In some of any of the embodiments described herein for a composition-of-matter or for a nanoparticle composite or for any characteristic thereof, the composition-of-matter is such that the metal oxide is copper oxide (CuO) or magnesium oxide (MgO), and the metallic element is magnesium (Mg), zinc (Zn) or copper (Cu), wherein said metallic element is different from said metal in said metal oxide.

In some embodiments the metal oxide is CuO and the metallic element is Zn, forming Zn-doped CuO nanoparticles (or nanoparticle composites). In some embodiments, the nanoparticle composites are represented by the Formula $Zn_xCu_yO$, with x and y as described hereinabove.

In some embodiments the atomic ratio y/x in $Zn_xCu_yO$ ranges of from 50:1 to 1:1. In some embodiments the atomic ratio y/x ranges is 50:1. In some embodiments the atomic ratio y/x ranges can be about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1, including any value therebetween.

In exemplary embodiments the atomic ratio y/x in $Zn_xCu_yO$ is about 8:1.

In some embodiments the metal oxide is CuO and the metallic element (dopant) is Mg, forming Mg-doped CuO nanoparticles (or nanoparticle composites). In some embodiments, the nanoparticle composites are represented by the Formula $Mg_xCu_yO$, with x and y as described hereinabove. In some embodiments the ratio y/x in $Mg_xCu_yO$ ranges of from 50:1 to 1:1. In some embodiments the ratio y/x ranges is 50:1. In some embodiments the ratio y/x ranges can be about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1, including any value therebetween.

In some embodiments the metal oxide is MgO and the metallic element (dopant) is Zn, forming Zn-doped MgO nanoparticles (or nanoparticle composites). In some embodiments, the nanoparticle composites are represented by the Formula $Zn_xMg_yO$, with x and y as described hereinabove.

In some embodiments the ratio y/x in $Zn_xMg_yO$ ranges of from 50:1 to 1:1. In some embodiments the ratio y/x ranges is 50:1. In some embodiments the ratio y/x ranges can be about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1 including any value therebetween.

In some embodiments the metal oxide is MgO and the metallic element (dopant is Cu), forming Cu-doped MgO nanoparticles (or nanoparticle composites). In some embodiments, the nanoparticle composites are represented by the Formula $Cu_xMg_yO$, with x and y as described hereinabove.

In some embodiments the ratio y/x in $Cu_xMg_yO$ ranges of from 50:1 to 1:1. In some embodiments the ratio y/x ranges is 50:1. In some embodiments the ratio y/x ranges can be about 49:1, about 48:1, about 47:1, about 46:1, about 45:1, about 44:1, about 43:1, about 42:1, about 41:1, about 40:1, about 39:1, about 38:1, about 37:1, about 36:1, about 35:1, about 34:1, about 33:1, about 32:1, about 31:1, about 30:1, about 29:1, about 28:1, about 27:1, about 26:1, about 25:1, about 24:1, about 23:1, about 22:1, about 21:1, about 20:1, about 19:1, about 18:1, about 17:1, about 16:1, about 15:1, about 14:1, about 13:1, about 12:1, about 11:1, about 10:1, about 9:1, about 8:1, about 7:1, about 6:1, about 5:1, about 4:1, about 3:1, about 2:1, or about 1:1 including any value therebetween.

Any other combinations of Mg, Cu, Zn and MgO, ZnO and MgO, at any atomic ratio, as described in any one of the respective embodiments described herein, is also contemplated.

In exemplary embodiments, the metal oxide is CuO and the metallic element is Zn.

In some of these embodiments, the atomic ratio of Cu to Zn is about 8:1.

In exemplary embodiments, the metal oxide is CuO and the metallic element is Mg.

In exemplary embodiments, the metal oxide is MgO and the metallic element is Cu or Zn.

Exemplary compositions-of-matter as described herein, in some embodiments thereof, are characterized by XRD patterns as described herein, namely, by an X-Ray Powder Diffraction which is devoid of peaks at positions that correspond to a pristine metal oxide of said metallic element, as described herein; and/or an X-Ray Powder Diffraction exhibiting at least one peak at a position and/or width that is different from a position and/or width of a corresponding peak in an X-Ray Powder Diffraction of said metal oxide, as described herein; and/or by a crystal lattice exhibiting at least one cell parameter that is different from a corresponding cell parameter of a pristine crystal lattice of said metal oxide.

Sonochemically-Prepared Compositions-of-Matter:

Any one of the compositions-of-matter described herein, and any embodiments thereof, including exemplary compositions-of-matter as described herein, can be prepared by any method known if the art for obtaining crystal-lattice doped metal oxides.

In some embodiments, a composition-of-matter as described herein, in any of the embodiments thereof, including exemplary compositions-of-matter as described herein, is prepared by subjecting a mixture of a first and a second metal precursor to high intensity ultrasonic irradiation. Such compositions-of-matter are also referred to herein as "sonochemically-prepared".

As used herein, the terms "sonochemical", "ultrasonic irradiation", "sonication" and grammatical diversions thereof, are used herein interchangeably, and refer to a method of exposure to sonic power, generally in the ultrasonic range of frequencies.

The term 'sonochemistry' refers to the study or use of sonochemical irradiation.

In some embodiments, ultrasonic irradiation is applied on a mixture (e.g., an aqueous solution) of metal precursors (e.g., metal ion salts) as described herein (e.g., copper acetate monohydrate or zinc acetate dihydrate).

In some embodiments the ultrasonic irradiation is applied by a Ti-horn apparatus.

In some embodiments the ultrasonic irradiation frequency applied during the sonication is of about at least 10 kHz, and can be about 10 kHz, about 20 kHz, about 30 kHz, about 40 kHz, about 50 kHz, about 60 kHz, about 70 kHz, about 80 kHz, about 90 kHz, or about 100 kHz including any value therebetween, or higher values.

In an exemplary embodiment the ultrasonic irradiation frequency applied during the sonication is 20 kHz.

In some of any of the embodiments described herein, the ultrasonic irradiation is applied at wave of at least 100 W, at least 200 W, at least 300 W, at least 400 W, at least 500 W, at least 600 W, at least 700 W, at least 800 W, at least 900 W, or at least 1 kW. In an exemplary embodiment the ultrasonic irradiation is applied at a wave of 750 W.

In some embodiments the ultrasonic irradiation is applied at a wave of 750 W, at at least 10% efficiency, at at least 20% efficiency, at at least 30% efficiency, at at least 40% efficiency, at at least 50% efficiency, at at least 60% efficiency, at at least 70% efficiency, at at least 80% efficiency, at at least 90% efficiency, or at 100% efficiency.

In some embodiments, sonication is performed at at least 10 W cm$^{-2}$ intensity, at at least 15 W cm$^{-2}$ intensity, at at least 20 W cm$^{-2}$ intensity, at at least 25 W cm$^{-2}$ intensity, at at least 30 W cm$^{-2}$ intensity, at at least 35 W cm$^{-2}$ intensity, at at least 40 W cm$^{-2}$ intensity, at at least 45 W cm$^{-2}$ intensity, at at least 50 W cm$^{-2}$ intensity, at at least 55 W cm$^{-2}$ intensity, at at least 60 W cm$^{-2}$ intensity, at at least 65 W cm$^{-2}$ intensity, at at least 70 W cm$^{-2}$ intensity, at at least 75 W cm$^{-2}$ intensity, at at least 80 W cm$^{-2}$ intensity, at at least 85 W cm$^{-2}$ intensity, or at at least 90 W cm$^{-2}$ intensity.

In an exemplary embodiment the ultrasonic irradiation is applied at 45 W cm$^{-2}$ intensity.

Further embodiments of this aspect of present embodiments are included hereinbelow, under "the process", and form an integral part of embodiments relating to sonochemically-prepared compositions-of-matter.

The Process:

According to an aspect of some embodiments of the present invention there is provided a process of preparing any of the compositions of matter described herein, which is effected by ultrasonic irradiation of a mixture of respective metal precursors, as described herein.

In some embodiments, the ultrasonic irradiation is effected as described hereinabove.

In some of any of the embodiments described herein, the sonication (high intensity ultrasonic irradiation) is effected on an aqueous solution comprising the mixture of metal precursors.

In some of any of the embodiments described herein, the process comprises, prior to the sonication, preparing a mixture comprising an aqueous solution of a first metal precursor and a second metal precursor, as described herein.

In some embodiments, the aqueous solution further comprises a water-miscible solvent. In some embodiments, the aqueous solution further comprises ethanol. In some embodiments the solution comprises ethanol at a ratio of 1:1 (v/v) ethanol:water, 2:1 (v/v) ethanol:water, 3:1 (v/v) ethanol:water, 4:1 (v/v) ethanol:water, 5:1 (v/v) ethanol:water, 6:1 (v/v) ethanol:water, 7:1 (v/v) ethanol:water, 8:1 (v/v) ethanol:water, 9:1 (v/v) ethanol:water, 10:1 (v/v) ethanol:water, 11:1 (v/v) ethanol:water, or 12:1 (v/v) ethanol:water, including any value therebetween.

In exemplary embodiments the solution comprises ethanol at a ratio of 9:1 (v/v) ethanol: water.

In some embodiments, the pH of the solution of the first and the second metal precursor is adjusted, optionally while subjecting the solution to ultrasonic irradiation, to a basic pH, higher than 7. In some embodiments the pH is adjusted to at least 8. In some embodiments the pH is adjusted to at least 9. In some embodiments the pH is adjusted to at least 10. In some embodiments the pH is adjusted to at least 11. In some embodiments the pH is adjusted to at least 12. In some embodiments the pH is adjusted to at least 13. In some embodiments the pH is adjusted to 14.

In exemplary embodiments the pH is adjusted to about 8.

In some embodiments the pH is adjusted by adding an alkaline aqueous solution to the sonicated mixture or solution.

In exemplary embodiments the pH is adjusted by adding an ammonia solution.

In some embodiments the ultrasonic irradiation is applied on the mixture or solution for at least 1 minute. In some embodiments the sonicated solution is applied for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 60 minutes, for at least 65 minutes, for at least 70 minutes, for at least 75 minutes, or for at least 80 minutes.

In exemplary embodiments the ultrasonic irradiation is applied on the mixture or solution for at least 30 minutes.

In some embodiments the sonicated mixture or solution is maintained at a temperature that ranges from 10° C. to 60° C., during the sonication procedure. In some embodiments the sonicated mixture or solution is maintained at temperature that ranges from 20° C. to 50° C., or from 25° C. to 45° C., or from 30° C. to 50° C.

In exemplary embodiments the sonicated mixture or solution is maintained at 30° C.

In some of any of the embodiments described herein for the sonication, the first metal precursor is such that forms the metal oxide.

In some of any of the embodiments described herein for the sonication, the first metal precursor is such that comprises the metallic dopant.

In some embodiments, the first metal precursor and the second metal precursors are each independently, a water soluble salt, which is capable of forming, preferably in the presence of air (oxygen) and/or water, a corresponding metal oxide.

By "water soluble" it is meant that the $K_{sp}$ of the salt in water is at least $10^{-10}$, at least $10^{-9}$, at least $10^{-8}$, at least $10^{-7}$, at least $10^{-6}$, at least $10^{-5}$, at least $10^{-4}$, at least $10^{-3}$, at least $10^{-2}$, or at least $10^{-1}$.

In some embodiments, each of the water soluble salts can independently be, for example, acetate salt, a nitrate salt a chloride salt, a bromide salt, an iodine salt, a sulfate salt, or a hydroxide salt. Any other water soluble salt is also contemplated.

Any of the water soluble salts as described herein can be utilized in a form of a hydrate thereof (e.g., monohydrate, dehydrate, trihydrate, tetsrahydrate, etc.).

Exemplary water soluble magnesium salts include, without limitation, magnesium acetate (e.g., tetrahydrate), magnesium nitrate, magnesium chloride, magnesium bromide, magnesium iodine, magnesium sulfate, magnesium chlorate, or magnesium hydroxide.

Exemplary water soluble copper salts include, without limitation, copper acetate, copper nitrate, copper chloride, copper bromide, copper sulfate, or copper chlorate.

Exemplary water soluble zinc salts include, without limitation, zinc acetate, zinc nitrate, zinc chloride, zinc bromide, zinc sulfate, zinc chlorate, zinc chlorate, or zinc hydroxide.

Exemplary water soluble calcium salts include, without limitation, calcium acetate, calcium nitrate, calcium chloride, calcium bromide, calcium iodide, calcium sulfate, calcium chlorate, calcium oxide, calcium hydroxide, or calcium sulfate.

Exemplary water soluble aluminum salts include, without limitation, aluminum acetate, aluminum nitrate, aluminum chloride, aluminum bromide, aluminum sulfate, aluminum chlorate, or aluminum sulfate.

In exemplary embodiments each of the water soluble salts are the corresponding acetate salts of the metals (namely, of the metal oxide and of the metallic element).

In some embodiments, the first metal precursor is a Cu precursor, namely a copper salt such as, for example, copper acetate monohydrate and the second metal precursor is a Zn precursor, namely a zinc salt, for example, zinc acetate dihydrate, and the nanoparticle composite is $Zn_xCu_yO$, as described herein in respective embodiments.

In some embodiments, the first metal precursor is a Cu precursor, namely a copper salt, for example copper acetate monohydrate and the second metal precursor is a Mg precursor, namely, a Mg salt, for example, magnesium acetate tetrahydrate, and the nanoparticle composite is $Mg_x$-$Cu_yO$, as described herein in respective embodiments.

In some embodiments, the first metal precursor is a Ng precursor, namely, a Mg salt, for example, magnesium acetate tetrahydrate and the second metal precursor is a Cu precursor, namely a copper salt, for example, copper acetate monohydrate, and the nanoparticle composite is $Cu_xMg_yO$, as described herein in respective embodiments.

In some embodiments, the first metal precursor is a Mg precursor, namely, a Mg salt, for example, the magnesium acetate tetrahydrate and the second metal precursor is a Zn precursor, namely a zinc salt, for example, zinc acetate dihydrate, and the nanoparticle composite is $Zn_xMg_yO$, as described herein in respective embodiments.

In some embodiments, the molar ratio of the first and the second metal precursor salts ranges from 50:1 to 1:50, or from 40:1 to 1:40, or from 30:1 to 1:30, or from 20:1 to 1:20, or from 12:1 to 1:12. In some embodiments, the molar ratio of first metal precursor and the second metal precursor is 12:1, 11:1, 10:1, 9:1, 8:1, 7:1, 6:1, 5:1, 4:1, 3:1, 2:1, 1:1, 1:12, 1:11, 1:10, 1:9, 1:8, 1:7, 1:6, 1:5, 1:4, 1:3, or 1:2, including any value therebetween.

In some embodiments, the molar ratio of copper acetate monohydrate and the zinc acetate dihydrate ranges from 12:1 to 1:12. In some embodiments, the molar ratio of copper acetate monohydrate and the zinc acetate dihydrate is 12:1, 11:1, 10:1, 9:1, 8:1, 7:1, 6:1, 5:1, 4:1, 3:1, 2:1, 1:1, 1:12, 1:11, 1:10, 1:9, 1:8, 1:7, 1:6, 1:5, 1:4, 1:3, or 1:2, including any value therebetween.

In some embodiments, the molar ratio of copper acetate monohydrate and the magnesium acetate tetrahydrate ranges from 12:1 to 1:12. In some embodiments, the molar ratio of copper acetate monohydrate and the zinc acetate dihydrate is 12:1, 11:1, 10:1, 9:1, 8:1, 7:1, 6:1, 5:1, 4:1, 3:1, 2:1, 1:1, 1:12, 1:11, 1:10, 1:9, 1:8, 1:7, 1:6, 1:5, 1:4, 1:3, or 1:2, including any value therebetween.

In some embodiments, the molar ratio of magnesium acetate tetrahydrate and the zinc acetate dihydrate ranges from 12:1 to 1:12. In some embodiments, the molar ratio of copper acetate monohydrate and the zinc acetate dihydrate is 12:1, 11:1, 10:1, 9:1, 8:1, 7:1, 6:1, 5:1, 4:1, 3:1, 2:1, 1:1, 1:12, 1:11, 1:10, 1:9, 1:8, 1:7, 1:6, 1:5, 1:4, 1:3, 1:2, including any value therebetween.

In some embodiments, the molar ratio of magnesium acetate tetrahydrate and the copper acetate monohydrate ranges from 12:1 to 1:12. In some embodiments, the molar ratio of copper acetate monohydrate and the zinc acetate dihydrate is 12:1, 11:1, 10:1, 9:1, 8:1, 7:1, 6:1, 5:1, 4:1, 3:1, 2:1, 1:1, 1:12, 1:11, 1:10, 1:9, 1:8, 1:7, 1:6, 1:5, 1:4, 1:3, 1:2, including any value therebetween.

In exemplary embodiments the molar ratio of the first metal precursor and the second metal precursor is 3:1.

In some of these embodiments, the first metal precursor is a Cu precursor as described herein and the second metal precursor is a Zn precursor as described herein.

In exemplary embodiments the molar ratio of copper acetate monohydrate and the zinc acetate dehydrate is 3:1.

In some embodiments, when an aqueous solution is used, the total molar concentration of the first and the second metal precursor salts ranges from about 0.0025M to about 5M.

In some embodiments, the total molar concentration of the first and the second metal precursor salts ranges from about 0.005M to about 1M.

In some embodiments, the total molar concentration of the first and the second metal precursor salts ranges from about 0.01M to about 0.1M.

In some embodiments, the total molar concentration of the first and the second metal precursor salts ranges from about 0.01M to about 0.1M.

In some embodiments, the total molar concentration of copper acetate monohydrate and the zinc acetate dihydrate ranges from about 0.0025M to about 5M.

In some embodiments, the total molar concentration of the copper acetate monohydrate and the zinc acetate dihydrate ranges from about 0.005M to about 1M.

In some embodiments, the total molar concentration of the copper acetate monohydrate and the zinc acetate dihydrate ranges from about 0.01M to about 0.1M.

In some embodiments, the total molar concentration of the copper acetate monohydrate and the zinc acetate dihydrate ranges from about 0.01M to about 0.1M.

In exemplary embodiments the total molar concentration of the copper acetate monohydrate and the zinc acetate dihydrate is 0.02M.

In exemplary embodiments the total molar concentration of the copper acetate monohydrate and the zinc acetate dihydrate is 0.01M.

In exemplary embodiments the total molar concentration of the copper acetate monohydrate and the zinc acetate dihydrate is 0.005M.

In some embodiments, the total molar concentration of copper acetate monohydrate and the magnesium acetate tetrahydrate ranges from about 0.0025M to about 5M.

In some embodiments, the total molar concentration of the copper acetate monohydrate and the magnesium acetate tetrahydrate ranges from about 0.005M to about 1M.

In some embodiments, the total molar concentration of the copper acetate monohydrate and the magnesium acetate tetrahydrate ranges from about 0.01M to about 0.1M.

In some embodiments, the total molar concentration of the copper acetate monohydrate and the magnesium acetate tetrahydrate ranges from about 0.01M to about 0.1M.

In some embodiments, the total molar concentration of zinc acetate dihydrate and the magnesium acetate tetrahydrate ranges from about 0.0025M to about 5M.

In some embodiments, the total molar concentration of the zinc acetate dihydrate and the magnesium acetate tetrahydrate ranges from about 0.005M to about 1M.

In some embodiments, the total molar concentration of the zinc acetate dihydrate and the magnesium acetate tetrahydrate ranges from about 0.01M to about 0.1M.

In some embodiments, the total molar concentration of the zinc acetate dihydrate and the magnesium acetate tetrahydrate ranges from about 0.01M to about 0.1M.

It is noted that the molar ratio of the first and the second metal precursors determined, at least in part, the atomic ratio between the metal of the metal oxide and the metallic element in the crystal-lattice doped metal oxide nanoparticles as described herein.

A Substrate or Article Incorporating the Nanoparticle Composite:

According to some of any of the embodiments described herein, a composition-according to any one of the respective embodiments, further comprises a substrate, and a plurality of nanoparticle composites as described in any of the respective embodiments, is incorporated in and/or on at least a portion of the substrate.

According to an aspect of some embodiments of the present invention, there is provided a substrate having incorporated in and/or on at least a portion thereof, metal-doped metal oxide nanoparticles (nanoparticle composites) as described herein.

According to an aspect of some embodiments of the present invention there is provided a substrate having incorporated in and/or on at least a portion thereof a sonochemically-prepared composition-of-matter as described herein in any of the respective embodiments.

By "a portion thereof" it is meant, for example, a surface or a portion thereof, and/or a body or a portion thereof, of solid or semi-solid substrates; or a volume or a part thereof, of liquid, gel, foams and other non-solid substrates.

As demonstrated in the Examples section that follows, substrates of widely different chemical nature can be successfully utilized for (e.g., sonochemically) incorporating (e.g., depositing on a surface thereof) metal-doped metal oxide nanoparticles thereon, as described herein. By "successfully utilized" it is meant that (i) the nanoparticle composites successfully form a uniform and homogenously coating on the substrate's surface upon ultrasonic irradiation thereof; and (ii) the resulting coating imparts long-lasting desired properties (e.g., antimicrobial properties) to the substrate's surface.

Compositions-of-matter further comprising a substrate as described herein, according to some embodiments of the present invention, can be prepared by contacting the substrate, or a portion thereof, with the first and second metal precursors as described herein, or a solution containing same, as described in any of the respective embodiments, and subjecting the substrate and the precursors mixture or solution to ultrasonic irradiation, as described in any of the respective embodiments.

In some embodiments, the contacting is effected by immersing the substrate or a portion thereof in a solution containing the first and second metal precursors.

Thus, an efficient one-step procedure for incorporating nanoparticle composites as described herein in and/or on various substrates is provided herein. As demonstrated in the Examples section that follows, such a procedure was successfully practiced foe variable substrates, including cotton and/or polyester fabrics, artificial tooth and silicon catheters.

Substrate usable according to some embodiments of the present invention can therefore be hard (rigid) or soft, solid, semi-solid, or liquid substrates, and may take a form of a foam, a solution, an emulsion, a lotion, a gel, a cream or any mixture thereof.

Substrate usable according to some embodiments of the present invention can have, for example, organic or inorganic surfaces, including, but not limited to, glass surfaces; porcelain surfaces; ceramic surfaces; silicon or organosilicon surfaces, metallic surfaces (e.g., stainless steel); MICA, polymeric surfaces such as, for example, plastic surfaces, rubbery surfaces, paper, wood, fabric in a woven, knitted or non-woven form, mineral (rock or glass), surfaces, wool, silk, cotton, hemp, leather, fur, feather, skin, hide, pelt or pelage) surfaces, plastic surfaces and surfaces comprising or made of polymers such as but not limited to polypropylene (PP), polycarbonate (PC), high-density polyethylene (HDPE), polyester (PE), unplasticized polyvinyl chloride (PVC), and fluoropolymers including but not limited to polytetrafluoroethylene (PTFE, Teflon®); or can comprise or be made of any of the foregoing substances, or any mixture thereof.

Alternatively, other portions, or the entire substrate are made of the abovementioned materials.

In exemplary embodiments the nanoparticles size in and/or on the substrate is about 80 nm. In further exemplary embodiments the doped metal oxide nanoparticles size is in a range of 10 to 80 nm. In yet further embodiments the nanoparticles size is about 25 nm. In some embodiments the nanoparticles size is about 10 nm. In some embodiments the nanoparticles size is less than 10 nm.

In exemplary embodiments the nanoparticle composites are in form of one or more layers of a continuous film. In yet further exemplary embodiments the thickness of the film is at least 30 nm. In still further exemplary embodiments the thickness of the film is at least 40 nm, at least 50 or at least 60 nm. In some of these embodiments, the film forms a part or is a coating on the substrate.

In some embodiments, the substrate incorporating nanoparticle composites as described herein is or forms a part of an article.

Hence according to an aspect of some embodiments of the present invention there is provided an article (e.g., an article-of-manufacturing) comprising a substrate incorporating tin and/or on at least a portion thereof a composition-of-matter or nanoparticle composites, as described in any one of the respective embodiments herein.

The articles can be prepared sonochemically, e.g., by contacting the article or a portion thereof, as described herein, with metal precursors as described herein, and subjecting the mixture to ultrasonic irradiation, as described herein. Alternatively, a substrate forming the article, and incorporating the nanoparticle composites is prepared as described herein, and is then used to construct the article.

The article can be any article which can benefit from the antimicrobial and/or anti-biofilm formation activities of the nanoparticle composites.

Exemplary articles include, but are not limited to, medical devices, pharmaceutical, cosmetic or cosmeceutic products, fabrics, bandages, microelectronic devices, microelectromechanic devices, photovoltaic devices, microfluidic devices, articles having a corrosivable surface, agricultural devices, packages, sealing articles, fuel containers and construction elements.

Non-limiting examples of medical devices which can incorporate nanoparticle composites beneficially, include catheters, tubing, endotracheal tubing, vaginal devices such as tampons, prosthetic devices, medical or cosmetic implants, artificial joints, artificial valves, needles, intravenous access devices, cannula, stents, biliary stents, cardiovascular stents, cardiac surgery devices, nephrostomy tubes, vascular grafts, infusion pumps, adhesive patches, sutures, fabrics, meshes, polymeric surgical tools or instruments, intubation devices, orthopedic surgery devices, pacemakers, endoscope components, dental surgery devices, veterinary surgery devices, bone scaffolds, hemodialysis tubing or equipment, blood exchanging and transfusion devices, implantable prostheses, bandages, ophthalmic devices, wound dressings, breast implants, pacemakers, heart valves, replacement joints, catheters, catheter access ports, dialysis tubing, gastric bands, shunts, screw plates, artificial spinal disc replacements, internal implantable defibrillators, cardiac resynchronization therapy devices, implantable cardiac monitors, mitral valve ring repair devices, left ventricular assist devices (LVADs), artificial hearts, implantable infusion pumps, implantable insulin pumps, stents, implantable neurostimulators, maxillofacial implants, dental implants, and the like.

According to some embodiments of the invention, the medical device is an implantable medical device, including medical devices that are implanted transiently or permanently. Examples include an indwelling catheter or an intubation device such as a tracheal tube. Non-limiting examples of indwelling catheters include urinary catheters, central venous catheters, biliary vascular catheters, pulmonary artery catheters, peripheral venous catheters, arterial lines, central venous catheters, peritoneal catheters, epidural catheters and central nervous system catheters.

In some embodiments, the medical device is such that is made of any of the suitable polymeric materials described hereinabove (e.g., at least a portion of the medical device comprises a polymeric material).

According to some embodiments of the invention, the medical device is a tampon or a vaginal medical device.

The term "tampon", as used herein, refers to a medical device in the form of a plug made from a mass of absorbent materials which is inserted into a wound or a body site to absorb exuded fluids, such as blood. One of the most common types of tampons in daily household use is designed to be inserted into the vagina during menstruation to absorb the flow of menstrual fluid. Such tampons are regarded officially as medical devices in many courtiers around the world, and according to the United States Food and Drug Administration, tampons are a Class II medical device.

In some embodiments, the term "tampon" describes tampons designed to be inserted into the vagina during menstruation to absorb the flow of menstrual fluid. The tampon can be a commercially available tampon of any type, composition, absorption rate, size and/or blend.

Tampons are typically made from cotton, rayon and blends thereof, and are available in different sizes for various conditions and absorbing rates. Tampons may include an applicator, which is a polymeric tube sheathing the absorbent plug for facilitating its insertion into the vagina.

Exemplary vaginal medical condition include, without limitation, bacterial vaginitis (BV), toxic shock syndrome (TSS), toxic shock-like syndrome (TSLS), streptococcal toxic shock syndrome (STSS), vulvovaginal candidiasis (VVC), chronic or persistent yeast infections (RVVC), a sexual dysfunction, a female reproductive system related disorder and a post-surgery vaginal related condition.

Exemplary packages or containers include, for example, food packages and containers, beverage packages and containers, medical device packages, agricultural packages and containers (of agrochemicals), blood sample or other biological sample packages and containers, and any other packages or containers of various articles.

Exemplary food packages include packages of dairy products and/or containers for storage or transportation of dairy products.

Other exemplary articles of manufacturing include milk storage and processing devices such as, but not limited to, containers, storage tanks, raw milk holding equipments, dairy processing operations conveyer belts, tube walls, gaskets, rubber seals, stainless steel coupons, piping systems, filling machine, silo tanks, heat exchangers, postpasteurization equipments, pumps, valves, separators, and spray devices.

In some embodiments, the article is an energy harvesting device, for example, a microelectronic device, a microelectromechanic device, a photovoltaic device and the like.

In some embodiments, the article is a microfluidic device, for example, micropumps or micro valves and the like.

In some embodiments, the article includes a sealing part, for example, O rings, and the like.

In some embodiments, the article is, for example, article having a corrosivable surface.

In some embodiments, the article is an agricultural device.

In some embodiments, the article is made of textile, for example, cotton, polyester, lycra, wool, silk, and the like, as described herein.

In some embodiments, the article is fuel transportation device.

In some embodiments, the article of manufacture is a construction element, such as, but not limited to, paints, walls, windows, door handles, and the like.

In some embodiments, the article is an element used in water treatment systems (such as for containing and/or transporting and/or treating aqueous media or water), devices, containers, filters, tubes, solutions and gases and the likes.

In some embodiments, the article is an element in organic waste treatment systems (such as for containing and/or disposing and/or transporting and/or treating organic waste), devices, containers, filters, tubes, solutions and gases and the likes.

In some embodiments, the article is a pharmaceutical, cosmetic or cosmeceutical product. Such products, in some embodiments, comprise a pharmaceutical, cosmetic or cosmeceutical formulation incorporating the nanoparticle composites as described herein.

In some embodiments, the product comprises a cosmetic, cosmeceutical or pharmaceutical formulation such as skincare formulations, makeup or dermatological or other topical pharmaceutical formulations, comprising the nanoparticle composites as described herein. The formulation can optionally and preferably further comprise a carrier, and optionally additional active agents and/or additives.

As used herein a "formulation" refers to a vehicle in the form of emulsion, lotion, cream, gel etc., that comprises physiologically acceptable carriers and/or excipients and optionally other chemical components such as cosmetically, cosmeceutically or pharmaceutically active agents (e.g., drugs).

As used herein, the term "physiologically acceptable" means approved by a regulatory agency of the Federal or a state government or listed in the U.S. Pharmacopeia or other generally recognized pharmacopeia for use in animals, and more particularly in humans.

Herein, the phrase "physiologically suitable carrier" refers to an approved carrier or a diluent that does not cause significant irritation to an organism and does not abrogate the biological activity and properties of a possible active agent.

Herein the term "excipient" refers to an inert substance added to a formulation as described herein to further facilitate processes and administration of the active ingredients.

In some embodiment of the present invention, the pharmaceutical, cosmetic or cosmeceutical formulation is formulated in a form suitable for topical application on the applied area.

By selecting the appropriate carrier and optionally other ingredients that can be included in the formulation, as is detailed hereinbelow, it may be formulated into any form typically employed for topical application.

The formulations can be water based, oil based or silicon based.

In some embodiments, the formulations are colloidal formulations, in which the nanoparticle composites are dispersed, suspended or otherwise distributed in the carrier.

The formulations as described herein can be, for example, skin care products, make-up products (including eye shadows, make-up, lipstick, lacquer, etc., or any other product as described herein).

In some embodiments, a formulation as described is in a form of a cream, an ointment, a paste, a gel, a lotion, a milk, an oil, a suspension, a solution, an aerosol, a spray, a foam, or a mousse.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emolliency). As with other carriers or vehicles, an ointment base should be inert, stable, nonirritating and nonsensitizing. As explained in *Remington: The Science and Practice of Pharmacy,* 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the sunscreens-containing microcapsules, are present in a water or alcohol base. Lotions are typically preferred for covering/protecting large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to *Remington: The Science and Practice of Pharmacy*, supra, for further information.

Pastes are semisolid dosage forms in which the bioactive agent is suspended in a suitable base. Depending on the nature of the base, pastes are divided between fatty pastes or those made from a single-phase aqueous gels. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or hydroalcoholic, but are typically formulated with high alcohol content which, upon application to the skin of a user, quickly evaporates, driving the active ingredient through the upper skin layers to the site of treatment.

The preparation of the formulation can be carried out by mixing and homogenizing all the ingredients. A product comprising such formulations, as described herein, can be prepared, for example, by contacting the formulation with already prepared nanoparticle composites as described herein, or by contacting the formulation with a first and a second metal precursor as described herein and subjecting the obtained mixture to ultrasonic irradiation as described herein in any of the respective embodiments.

In any of the formulations described herein, additional agents and/or additives can be included.

Some non-limiting representative examples of additives and/or agents include humectants, deodorants, antiperspirants, sunless tanning agents, hair conditioning agents, pH adjusting agents, chelating agents, preservatives, emulsifiers, occlusive agents, emollients, thickeners, solubilizing agents, penetration enhancers, anti-irritants, colorants, propellants and surfactants.

In some embodiments, the article is a dye formulation, including any of the formulations described hereinabove, or any other carriers, solvents, etc. incorporating a dye substance.

The phrase "topical application" and grammatical diversions thereof, is meant to encompass, without limitation, dermal applications, ophthalmic application, vaginal application, rectal application and intranasal application.

According to some embodiments of the present invention, formulation containing the metal-doped metal oxide nanoparticles presented herein can be concocted into any pharmaceutical form normally employed for topical application, such as creams, lotions, ointments, suppositories, powder or oily bases, dressings, solutions, gels, mousses, pastes, soaps, pads, wipes, patches, swabs and pledgets.

In some embodiments, a substrate's surfaces as described herein can further be modified by various chemical and mechanical processes, including, for example, SAMs, PVD, lithography and plasma etching.

In exemplary embodiments the substrate is made of cotton fabrics from either woven or non-woven cotton bandage. In exemplary embodiments the substrate is made of artificial acryl tooth. In exemplary embodiments the substrate is made of a glass. In still further exemplary embodiments the substrate is urinary catheters catheter made of silicon.

Antimicrobial and Anti-Biofilm Formation Applications:

According to an aspect of some embodiments of the present invention, there is provided a pharmaceutical, cosmetic or cosmeceutical product comprising the compositions-of-matter or the nanoparticle composites as described in any of their respective embodiments herein, for use in treating a medical, cosmetic or cosmeceutic condition, as described herein.

According to a further aspect of some embodiments of the present invention, there is provided a use of compositions-of-matter as described herein in the manufacture of a pharmaceutical, cosmetic or cosmeceutical product, which can be used in treating a medical, cosmetic or cosmeceutic condition, as described herein.

In some embodiments there is provided a use of the formulation containing metal-doped metal oxide nanoparticles as described herein, in the manufacture of a medicament for the treatment of a medical, cosmeceutical or cosmetic condition.

In some embodiments there is provided a method of treating a medical, cosmeceutical or cosmetic condition treatable by topical or transdermal administration, the method comprising topically applying a formulation as described herein (e.g., in the context of a pharmaceutical, cosmetic or cosmeceutic product), containing nanoparticle composites as described herein to a skin or mucosal tissue of a subject afflicted by the condition.

Medical, cosmetic or cosmeceutical conditions that can benefit from containing nanoparticle composites as described herein when applied topically, with or without an additional active ingredient, include, but are not limited to, infections caused by pathogenic microorganisms, as discussed in further detail hereinbelow, wounds, particularly when associated with an infection, acne, skin infections, viral blisters such as one caused by herpes, sexual dysfunction such as erectile dysfunction.

Hence, according to some embodiments of the present invention, the pharmaceutical, cosmetic or cosmeceutical formulation or product further comprises an antimicrobial agent, as an additional pharmaceutically active agent.

Microbial infections include any infection caused by a pathogenic microorganism, including, bacterial infection, fungal infection, protozoal infection, viral infection and the like, including molluscum contagiosum (a viral infection of the skin or occasionally of the mucous membranes), fungal nail infections, and cutaneous leishmaniasis.

Topical bodily sites include skin, mucosal tissue, eye, ear, nose, mouth, rectum and vagina.

In some embodiments, there is provided an article (e.g., a medical device such as a bandage or adhesive patch), or a formulation, or a product, as described herein, configured for topical application, whereby a condition treatable by such as article or product or formulation is an infection caused by is *P. Acne*.

According to an aspect of some embodiments of the present invention there is provided a method of inhibiting or reducing or retarding the formation of load of a microorganism and/or the formation of a biofilm, in and/or on an article. The method comprises incorporating in and/or on the article any one of the compositions-of-matter as described herein, including any of the respective embodiments thereof.

The article can be any one of the articles described herein.

Such articles take advantage of the improved antimicrobial activity exhibited by the nanoparticle composites as described herein.

Herein "antimicrobial activity" is referred to as an ability to inhibit (prevent), reduce or retard bacterial growth, fungal growth, biofilm formation or eradicate living bacterial cells, or their spores, or fungal cells or viruses in a suspension or in a moist environment.

Herein, inhibiting or reducing or retarding the formation of load of a microorganism refers to inhibiting reducing or retarding growth of microorganisms and/or eradicating a portion or all of an existing population of microorganisms.

Thus, nanoparticle composites as described herein can be used both in reducing the formation of microorganisms on or in an article, and in killing microorganisms in or on an article or a living tissue.

The microorganism can be, for example, a unicellular microorganism (prokaryotes, archaea, bacteria, eukaryotes, protists, fungi, algae, euglena, protozoan, dinoflagellates, apicomplexa, trypanosomes, amoebae and the likes), or a multicellular microorganism.

An article, according to these embodiments, can be also a living tissue, for example, a skin or mucosal tissue, as described herein.

In the context of the present embodiments, the compositions, articles and methods described herein may be used to produce cell inhibiting surface, or a microbial cell killing surface, that remains active for extended periods. Such an antimicrobial surface may not need additional treatment with antimicrobial compositions, clean-up treatments to effect decontamination and cosmetic painting, thereby simplifying upkeep of the physical condition and appearance of microbial infestation prone surfaces. It is contemplated that in some embodiments the compositions of the present invention may be easily applied to susceptible surfaces in advance of and/or during exposure to a microbial organism.

In some embodiments, the microorganism comprises bacterial cells of bacteria such as, for example, Gram-positive and Gram-negative bacteria.

The term "biofilm", as used herein, refers to an aggregate of living cells which are stuck to each other and/or immobilized onto a surface as colonies. The cells are frequently embedded within a self-secreted matrix of extracellular polymeric substance (EPS), also referred to as "slime", which is a polymeric sticky mixture of nucleic acids, proteins and polysaccharides.

In the context of the present embodiments, the living cells forming a biofilm can be cells of a unicellular microorganism (prokaryotes, archaea, bacteria, eukaryotes, protists, fungi, algae, euglena, protozoan, dinoflagellates, apicomplexa, trypanosomes, amoebae and the likes), or cells of multicellular organisms in which case the biofilm can be regarded as a colony of cells (like in the case of the unicellular organisms) or as a lower form of a tissue.

In the context of the present embodiments, the cells are of microorganism origins, and the biofilm is a biofilm of microorganisms, such as bacteria and fungi. The cells of a microorganism growing in a biofilm are physiologically distinct from cells in the "planktonic form" of the same organism, which by contrast, are single-cells that may float or swim in a liquid medium. Biofilms can go through several life-cycle steps which include initial attachment, irreversible attachment, one or more maturation stages, and dispersion.

The phrases "anti-biofilm formation activity" refers to the capacity of a substance to effect the prevention of formation of a biofilm of bacterial, fungal and/or other cells, and/or to effect a reduction in the rate of buildup of a biofilm of bacterial, fungal and/or other cells, on a surface of a substrate. This activity is also referred to herein as anti-biofouling activity, or antifouling activity.

In some embodiments, the biofilm is formed of bacterial cells (or from a bacterium).

In some embodiments, a biofilm is formed of bacterial cells of Gram-positive and/or Gram-negative bacteria.

As demonstrated herein, a composition of matter as described herein was shown to exhibit anti-biofilm formation (ABF) activity and can thus prevent, retard or reduce the formation of a mass of a biofilm.

In some embodiments of the present invention, the activity of preventing or reducing the formation of a biofilm, may be achieved by a substrate or an article incorporating nanoparticle composites, as described herein.

The inhibition or reduction or retardation of formation of a biofilm assumes that the biofilm has not yet been formed, and hence the presence of the doped metal-oxide nanoparticles is required also in cases where no biofilm is present or detected.

As used herein, the term "preventing" in the context of the formation of a biofilm, indicates that the formation of a biofilm is essentially nullified or is reduced by at least 20%, at least 30%, at least 40%, at least 50%, at least 60%, at least 70%, at least 80%, at least 90%, including any value therebetween, of the appearance of the biofilm in a comparable situation lacking the presence of the metal-oxide nanoparticles or a composition of matter containing same. Alternatively, preventing means a reduction to at least 15%, 10% or 5% of the appearance of the biofilm in a comparable situation lacking the presence of the metal-doped metal oxide nanoparticles or a composition of matter containing same. Methods for determining a level of appearance of a biofilm are known in the art.

As used herein, the term "preventing" in the context of antimicrobial, indicates that the growth rate of the microorganism cells is essentially nullified or is reduced by at least 20%, at least 30%, at least 40%, at least 50%, at least 60%, at least 70%, at least 80%, at least 90%, including any value therebetween, of the appearance of the microorganism in a comparable situation lacking the presence of the metal-doped metal oxide nanoparticles or a composition of matter containing same. Alternatively, preventing means a reduction to at least 15%, 10% or 5% of the appearance of the microorganism cells in a comparable situation lacking the presence of the metal-doped metal oxide nanoparticles or a composition of matter containing same. Methods for determining a level of appearance of a microorganism cells are known in the art.

In some embodiments, inhibiting, reducing and/or retarding a formation of a biofilm as described herein is reflected by reducing biofilm formation on e.g., a substrate's surface by at least 20%, at least 30%, at least 40%, at least 50%, at least 60%, at least 70%, at least 80%, at least 90%, including any value therebetween, compared to the same substrate which does not have said metal-doped metal oxide nanoparticles applied on a surface thereof.

In some embodiments there is provided an article which comprises the composition of matter incorporated in and/or on a substrate.

Further according to an aspect of some embodiments of the present invention there is provided a method of inhibiting, reducing and/or retarding a formation of a biofilm in or on a substrate or an article containing the substrate or an article containing the substrate, which is effected by sonochmically incorporating in and/or on the substrate an antifouling effective amount of a composition-of-matter as described herein, in any one of the respective embodiments.

Substrates usable in the context of these embodiments of the present invention include any of the substrates described hereinabove. Compositions of matter usable in the context of these embodiments include any of the compositions of matter described hereinabove.

Articles usable in the context of these embodiments include any of the articles of manufacturing described hereinabove.

Preferably, articles of manufacturing in which prevention of biofilm formation are of high importance are usable in the context of these embodiments of the present invention.

Compositions of matter as described herein can be incorporated within any of the articles of manufacturing, during manufacture of any of the article described herein.

The substrates presented herein can be used to modify any industrial or clinical surface to prevent bacterial colonization and biofilm formation.

General:

It is expected that during the life of a patent maturing from this application many relevant hydrocarbons will be developed and the scope of the term hydrocarbon is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

Materials:

All reagents were purchased from Sigma-Aldrich and used without further purification, unless otherwise indicated.

*Escherichia coli* (*E. coli*) 1313 and *Staphylococcus aureus* (*S. aureus*) 195, each of which was from clinical isolated strains, were obtained from the Bacteriological Laboratory of the Meir Hospital, Kfar Sava, Israel.

Two Multi-Drug Resistant (MDR) Bacteria stains were isolated and obtained from Tel-Aviv medical center "Ichilov": *E. coli*—clinical (blood) isolate belonging to sequence type ST131 lineage, producing CTX-M-15 extended-spectrum b-lactamase, and methicillin resistant *S. aureus* (MRSA)—belonging to USA300 lineage.

*Propionobacterium acnes* (*P. acnes*; strain ATCC 6919) strains were obtained from the ATCC strain collection.

*S. mutans* 700610 (clinical isolate) was obtained from the Hebrew University Dental School.

*Candida albicans* (a clinical isolated) was obtained from the bacteriological laboratory of the Meir Hospital, Kfar-Sava, Israel.

Growth media: Nutrient Broth (NB), Brain Heart (BH) were purchased from Difco, Detroit, Mich. Luria Bertani (LB) medium was purchased from Hy-labs, Rehovot, Israel.

Brain-heart medium supplemented with 0.5% sucrose (denoted BH) and Muller-Hinton (MH) were obtained from BD Biosciences. Glass slides were purchased from Marienfeeld (Germany).

Artificial acryl tooth was obtained from the School of Dental Medicine at the Tel Aviv University, Tel-Aviv, Israel.

French pediatric silicon urinary catheters were obtained from Degania—Silicon, Israel.

Cotton fabric was obtained from either woven or non-woven cotton bandage provided by Kopman, Italy.

The coating was done also on polyester polyester/cotton and cotton bandage.

Microwave irradiation was performed using a domestic microwave oven modified with reflection system, (Sharp, 1200W, 100% intensity).

The Cu and Zn concentrations in the cotton fabric were determined by ICP analysis (ULTIMA 2).

The particle morphology and size distribution was studied by SEM and HRSEM—FEI INSPECT.

ESR spectra were recorded on a Bruker ER 100d x band spectrometer.

XRD Measurements:

Structural and microstructural characterization of the products was performed by means of X-ray diffraction (XRD) on the powder collected at the end of the reactions. The XRD measurements patterns of the products were registered with a Bruker D8 diffractometer having Cu K$\alpha$ radiation ($\lambda$=1.5418 Å). Peak fitting and lattice parameter refinement were computed using the Topas and Metric programs (Bruker Analytical X-Ray Systems). Calculations of the cell parameters were performed by the Rietveld method.

DSC Analysis:

Differential scanning calorimetric (DSC) thermograms were obtained on the Mettler Toledo DSC Star$^e$ System, for elevated temperatures at a heating rate of 10° C./minute, under both inert (i.e. flowing, pure nitrogen; 50 ml/minute) and oxidizing conditions (i.e. under air).

Zeta Potential measurements:

The zeta-potential of the nanoparticles (e.g., Zn—CuO, CuO) in BH medium was determined at room temperature (about 25° C.) using a Malvern zetasizer (Malvern Instruments). The procedure was carried out at least three times for each of the individual nanoparticle suspension.

Leaching Experiments:

Leaching studies were carried out on the coated catheter following 72 hours incubation with either saline, artificial urine (consist of: 25 gram/liter urea, 9 gram/liter Sodium chloride, 2.5 gram/liter potassium phosphate monobasic, 2.5 gram/liter sodium phosphate dibasic, 3 gram/liter ammonium chloride, 2 gram/liter creatinine and 3 gram/liter sodium sulfite all purchased from Sigma-Aldrich) and 1% MH medium (BD Biosciences). 0.4 gram of a coated catheter was incubated in 2 ml of the tested solution for 72 hours with shaking 50 rpm at 37° C. Following incubation 1 ml of the solution was taken for probing the presence of leached ions using ICP analysis.

SEM Measurements:

Surface imaging of substrates (e.g., cotton fabric, artificial tooth, catheter) having metal oxide nanoparticles deposited thereon was studied by scanning electron microscopy (SEM) and high-resolution SEM (HRSEM; FEI INSPECT, accelerating voltage 15 kV). Statistical analysis of the particle size distribution was determined from the measurement of images captured with HRSEM (n=100) using the Scion image software (Scion 2.0, Scion Corporation) for image processing and the Microcal Origin program for data analysis (Origin 7.0, OriginLab).

Focused Ion Beam (FIB)-SEM Measurements:

The cross-section morphology of the coated substrate (e.g., artificial tooth) was studied in regards to the thickness of the coating and the nanoparticles penetration depth profile into the bulk of the substrate was employed by a focused ion beam (FIB) using dual beam system (FEI Helios 600)

system with several electron and ion beams up to 30 kV at different angles (52 degrees) that image the substrate sample simultaneously.

RBS Measurements:

The existence of nanoparticles on the coated substrate and their penetration depth profile of the nanoparticles into the bulk of the substrate was examined by Rutherford Backscattering Spectroscopy (RBS) microbeam analysis using a 1.7 MV Pelletron accelerator from NEC. For each sample, an RBS spectrum was acquired with a fixed detector (ULTRA Silicon-Charged Particle Detector, ORTEC). For each sample, a spectrum of 5-μC fluence was collected with a 2.022 MeV±1 KeV He beam; the nominal diameter of the beam is 2 mm. An electron suppressor was used between the beam entrance and the sample holder, which was biased at −100 V vs. ground. The scattering angle of the fixed detector was 169°, and solid angle was 2.7 millisteradians (msr). A normal incident beam was used in all measurements. Every sample was mounted in the holder using double-sided, self-adhesive carbon tape. To fit the data NDF version 9.4e software was used. SRIM 2003 was used as stopping powers. The double-scattering calculation in NDF was employed to fit of the low-energy signal. The pulse pileup calculation in NDF uses the algorithm of Wielopolsky & Gardner.

Enhanced backscattering spectroscopy (EBS) was used to make small corrections for 0 and C in the cross-sections. The EBS (non-Rutherford) scattering cross-sections were obtained from IBANDL. SigmaCalc was used for evaluating cross-sections (e.g., C, N, O, Si). Depth profiles can be extracted automatically from RBS, EBS, ERD, and NRA spectra using the Surrey IBA DataFurnace software. The accuracy of this code was validated against a certified standard sample.

Additional materials and methods information is included in the Examples the follows.

Example 1

Preparation of Metal Oxide Nanoparticles

Preparation of Metal-Oxide Nanoparticles by Applying Ultrasonic Irradiation (Sonochemically-Prepared Metal Oxide Nanoparticles)—General Procedure:

A metal precursor or a mixture of a first and a second metal precursors is dissolved in water (e.g., double distilled water), ethanol is added so as to obtain a solution of e.g., 9:1 (v/v) ethanol:water, and the solution is subjected to ultrasonic irradiation using high intensity sonication (e.g., using an immersed Ti-horn, 20 kHz, 750 W at 40% efficiency, Sonics & Materials VCX600 Sonofier). After 1 to 10 minutes, an alkaline aqueous solution (e.g., 28-30% ammonia solution) is added to the sonicated reaction mixture, and the reaction vessel is maintained at 30° C. (e.g., by means of a water bath) for additional 30-60 minutes. The obtained solution is thereafter centrifuged, and the obtained nanoparticles are dried under vacuum.

In some embodiments, sonication is performed at 45 W cm$^{-2}$ intensity.

Doped metal oxide nanoparticles are similarly prepared while using a mixture of two metal precursors, at varying molar ratios.

The following describes exemplary procedures:

Preparation of CuO Nanoparticles Via Ultrasonic Irradiation:

15 grams of copper acetate monohydrate (an exemplary Cu precursor) were dissolved in double distilled water (ddH$_2$O; 10 ml) while stirring. Ethanol (90 ml) was thereafter added and the solution was subjected to high intensity ultrasonic irradiation with an immersed Ti-horn (20 kHz, 750 W at 40% efficiency, 45 W cm$^{-2}$ intensity, Sonics & Materials VCX600 Sonofier).

After 5 minutes of sonication, 0.8 ml of an aqueous solution of ammonia (28-30%) was added to the reaction mixture so as to adjust the pH to about 8. Once ammonia was added, the color of the reaction mixture turned from pale blue to dark blue and then became a dark brown. The reaction mixture was kept cooled in a water bath during the sonication so as to maintain a temperature of 30° C. After 30 minutes of high-intensity unitrasonic irradiation as above, the obtained CuO nanoparticles were cleaned of impurities and traces of ammonia by centrifugation (1000 rpm), washed twice with double-distilled water and once with ethanol, and then dried under vacuum.

Preparation of Zn-Doped CuO Nanoparticles Via Ultrasonic Irradiation:

Copper acetate monohydrate (an exemplary Cu precursor) and zinc acetate dihydrate (an exemplary Zn precursor) were used as metal precursors, at the following molar ratios: 4:1, 3:1, 2:1, 1:1, 1:2, 1:3 and 1:4, and the procedure described above for preparation of CuO nanoparticles via ultrasonic irradiation was applied.

In exemplary procedures, for the 3:1 molar ratio of the corresponding Cu and Zn precursors the total concentrations of $Cu^{2+}$ and $Zn^{2+}$ ions in an aqueous solution were examined, and are marked as "high" (total: 0.02 M; [$Cu^{2+}$]=0.015 M, [$Zn^{2+}$]=0.005), "medium" (total: 0.01 M; [$Cu^{2+}$]=0.0075 M, [$Zn^{2+}$]=0.0025), designated hereinbelow as: "med-3:1Cu:Zn" and "low" (total: 0.005 M; [$Cu^{2+}$]=0.00375 M, [$Zn^{2+}$]=0.00125), all of which are in 100 ml of 9:1 (v/v) ethanol:water.

In exemplary procedures the concentration and molar ratio as designated hereinabove as med-3:1 Cu:Zn were achieved by dissolving 0.15 grams of copper acetate monohydrate and 0.055 grams of zinc acetate dihydrate in double distilled water (ddH$_2$O; 10 ml) while stirring and thereafter adding of ethanol (90 ml) to the solution so as to obtain a solution of 100 ml of 9:1 (v/v) ethanol:water.

In exemplary procedures, for the 4:1 molar ratio of the corresponding Cu:Zn precursors the total concentrations of $Cu^{2+}$ and $Zn^{2+}$ ions in an aqueous solution were of the "medium" concentration (i.e. total 0.01 M; [$Cu^{2+}$]=0.008 M, [$Zn^{2+}$]=0.002M), designated herein below as: "med-4:1Cu:Zn" in 100 ml of 9:1 (v/v) ethanol:water.

In exemplary procedures, for the 2:1 molar ratio of the corresponding Cu:Zn precursors the total concentrations of $Cu^{2+}$ and $Zn^{2+}$ ions in an aqueous solution were of the "medium" concentration (i.e. total 0.01 M; [$Cu^{2+}$]=0.0067 M, [$Zn^{2+}$]=0.0033M), designated herein below as: "med-2:1 Cu:Zn" in 100 ml of 9:1 (v/v) ethanol:water.

In exemplary procedures, for the 1:1 molar ratio of the corresponding Cu:Zn precursors the total concentrations of $Cu^{2+}$ and $Zn^{2+}$ ions in an aqueous solution were of the "medium" concentration (i.e. total 0.01 M; [$Cu^{2+}$]=0.0050 M, [$Zn^{2+}$]=0.0050M) designated herein below as: "med-1:1 Cu:Zn" in 100 ml of 9:1 (v/v) ethanol:water.

In exemplary procedures, the Cu precursor was dissolved in 10 ml water, the Zn precursor was added, and ethanol (90 ml) was added to a final volume of 100 ml. The obtained solution was subjected to sonication as described hereinabove for CuO nanoparticles. The obtained nanoparticles were similarly isolated, washed and dried.

Hereinthroughout, nanoparticles and/or the precursors mixture used for preparing same can be identified by the molar ratio of the metal precursors used, namely, by indicating 1:1 or 2:1, or 3:1, etc. before "Cu:Zn" or before Zn-doped CuO, with the left digit in the molar ratio indicating the relative concentration of a Cu precursor. Nanoparticles can also be identified by the concentration of the precursors as being medium (med), high or low.

Deposition of Metal Oxide Nanoparticles on Substrates Via Ultrasonic Irradiation:

In a general procedure, a metal precursor or a mixture of metal precursors is dissolved in water, ethanol is added to obtain e.g., a 9:1 ethanol:water solution, the substrate is immersed in the solution and the obtained mixture is subjected to ultrasonic irradiation as described hereinabove. The substrate was kept at a constant distance of 2 cm from the sonicator tip during the entire reaction process.

The obtained coated substrate was thereafter washed twice with double-distilled water and once with ethanol, and then dried under vacuum.

In exemplary procedures, CuO nanoparticles, ZnO nanoparticles and Zn-doped CuO nanoparticles were deposited on substrates using the exemplary metal precursors indicated hereinabove. For Zn-doped CuO nanoparticles, a mixture of metal precursors at a concentration and molar ratio as designated hereinabove as med-3:1 Cu:Zn was used, unless otherwise indicated.

Nanoparticles coatings on artificial tooth were obtained by placing an artificial acryl tooth directly into the sonochemical reaction medium according to the methodology described above. The tooth was held by a wire to keep it at a constant distance of 2 cm from the sonicator tip during the entire reaction process.

Nanoparticles coatings on cotton fabric were obtained by placing a cotton fabric (sized e.g., 2×3 $cm^2$) in the sonochemical reaction medium according to the methodology described above.

Nanoparticles coatings on cotton fabric were obtained by placing a glass slide (sized e.g., 2×3 $cm^2$) in the sonochemical reaction medium according to the methodology described above.

Nanoparticles coatings on a catheter were obtained by placing catheter segments (sized e.g., 5 cm) in the sonochemical reaction medium according to the methodology described above.

Subjecting Cu Precursor and Zn Precursor to Microwave Irradiation (Reference Example 1)

A mixture of metal precursors in a concentration and molar ratio as designated hereinabove as med-3:1 Cu:Zn was obtained by dissolving 0.15 grams of Copper acetate monohydrate and 0.055 grams of Zinc acetate dihydrate in double distilled water ($ddH_2O$; e.g., 10 ml) while stirring and thereafter adding ethanol (90 ml) to the solution so as to obtain a solution of 100 ml of 9:1 (v/v) ethanol:water. The obtained solution was subjected to microwave irradiation oven using a domestic microwave oven. After 1 minute from the beginning of the irradiation, 0.8 ml of an aqueous solution of ammonia (28-30%) was added to the reaction mixture so as to adjust the pH to about 8. Once ammonia was added, the color of the reaction mixture turned from pale blue to dark blue and then became a dark brown. After a time period of about 15 minutes, the obtained nanoparticles were cleaned of impurities and traces of ammonia by centrifugation (1000 rpm) following washing twice with double-distilled water and once with ethanol, and then dried under vacuum.

Subjecting Cu Precursor and Zn Precursor to Thermal Reaction (Reference Example 2)

A mixture of metal precursors in a concentration and molar ratio as designated hereinabove as med-3:1 Cu:Zn was obtained by dissolving 0.15 grams of Copper acetate monohydrate and 0.055 grams of Zinc acetate dihydrate in double distilled water ($ddH_2O$; 10 ml) while stirring and thereafter adding Ethanol (90 ml) to the solution so as to obtain a solution of 100 ml of 9:1 (v/v) ethanol:water. The obtained solution was heated at a heating plate to 60° C. while stirring and 0.8 ml of an aqueous solution of ammonia (28-30%) was added to the reaction mixture so as to adjust the pH to about 8. Once ammonia was added, the color of the reaction mixture turned from pale blue to dark blue and then became a dark brown. The reaction was carried out for 5 hours. The obtained particles were cleaned by centrifugation (1000 rpm), washed and dried, as described hereinabove.

Preparation of Zn-Doped MgO Nanoparticles Via Ultrasonic Irradiation:

Zinc acetate dihydrate (an exemplary Zn precursor) and magnesium acetate tetrahydrate (an exemplary Mg precursor) are used at the following molar ratios: 1:1, 1:2, 1:3 and 1:4, respectively.

In exemplary procedures, the Mg precursor is dissolved in water (e.g., 10 ml), and the Zn precursor is then added. Ethanol (e.g., 90 ml) is thereafter added to a final volume of 100 ml. After a time period ranging from 1 to 10 minutes, an alkaline aqueous solution (e.g., 28-30% ammonia solution) is added to the sonicated reaction mixture, and the reaction vessel is maintained at 30° C. (e.g., by means of a water bath) for additional 30-60 minutes. The obtained solution is thereafter centrifuged, and the obtained nanoparticles are dried under vacuum.

In exemplary procedures, for the all abovementioned molar ratio of the corresponding Zn and Mg precursors the total concentrations of $Zn^{2+}$ and $Mg^{2+}$ ions in the aqueous solution are in the range of from 0.05 to 0.005M.

Preparation of Cu-Doped MgO Nanoparticles Via Ultrasonic Irradiation:

The above procedure is performed using copper acetate monohydrate instead of the zinc precursor. Copper acetate monohydrate (an exemplary Cu precursor) and magnesium acetate (an exemplary Mg precursor) were used at the following molar ratios: 1:1, 1:2, 1:3 and 1:4, respectively.

Preparation of Mg-Doped CuO Nanoparticles Via Ultrasonic Irradiation:

Copper acetate monohydrate (an exemplary Cu precursor) and magnesium acetate (an exemplary Mg precursor) were used at the following molar ratios: 4:1, 3:1, 2:1, 1:1, respectively and the procedure described above for preparation of Zn-doped CuO nanoparticles via ultrasonic irradiation was applied.

In exemplary procedures, the Cu precursor was dissolved in water (e.g., 10 ml), and the Mg precursor was then added. Ethanol (e.g., 90 ml) was thereafter added to a final volume of 100 ml. After a time period ranging from 1 to 10 minutes, an alkaline aqueous solution (e.g., 28-30% ammonia solution) was added to the sonicated reaction mixture, and the reaction vessel was maintained at 30° C. (e.g., by means of a water bath) for additional 30-60 minutes. The obtained solution was thereafter centrifuged, and the obtained nanoparticles were dried under vacuum.

In exemplary procedures, for the all abovementioned molar ratio of the corresponding Mg and Cu precursors the total concentrations of $Mg^{2+}$ and $Cu^{2+}$ ions in the aqueous solution were in the range of from 0.05 to 0.005M.

Preparation of Mg-Doped or Cu-Doped ZnO Nanoparticles Via Ultrasonic Irradiation:

Zinc acetate dihydrate (an exemplary Zn precursor) and magnesium acetate (an exemplary Mg precursor) or copper acetate monohydrate (an exemplary Cu precursor) are used at the following molar ratios: 4:1, 3:1, 2:1, 1:1, respectively.

In exemplary procedures, the Zn precursor is dissolved in water (e.g., 10 ml), and the Mg or Cu precursor is then added. Ethanol (e.g., 90 ml) is thereafter added to a final volume of 100 ml. After a time period ranging from 1 to 10 minutes, an alkaline aqueous solution (e.g., 28-30% ammonia solution) is added to the sonicated reaction mixture, and the reaction vessel is maintained at 30° C. (e.g., by means of a water bath) for additional 30-60 minutes. The obtained solution is thereafter centrifuged, and the obtained nanoparticles are dried under vacuum.

Example 2

Sample Characterization

XRD Measurements:

FIG. 1 presents XRD patterns of sonochemically-prepared CuO nanoparticles (graph b), ZnO nanoparticles (graph a), and of Zn-doped CuO nanoparticles as obtained from the med-3:1Cu:Zn (graph c), all prepared using the procedures described in Example 1 hereinabove.

FIG. 1 presents in graph the XRD of sonochemically-synthesized ZnO. The peaks at 2θ angles=32.8, 35.621, 38.851, 48.246, 58.077, 66.506, 67.850, 75.104 are assigned to the (111), (−111), (202), (204), (120), (313), (221), (315) reflection lines of the ZnO hexagonal wurtzite structure, corresponding to the international crystallographic powder diffraction file (PDF) indexed 89-7102.

FIG. 1 further presents, in graph b therein, a representative XRD pattern showing CuO reflection lines, without any shifting and broadening of the peaks, as obtained following the sonochemical reaction using pristine copper acetate precursor. The peaks at 2θ=32.47, 35.49, 38.68, 48.65, 58.25, and 61.45 are assigned to the (110), (−111), (111), (−202), (202), and (−113) reflection lines of monoclinic CuO (PDF 80-1916).

FIG. 1 presents, in graph c therein, a comparative view of the XRD patterns of Zn-doped CuO nanoparticles powder collected following the sonochemical reaction of solution of med-3:1 Cu:Zn, as described hereinabove. As shown therein, all the peaks in the XRD spectra can be assigned to monoclinic crystal lattice of CuO. No peaks related to ZnO or any impurities were observed. It can be further observed that the peaks assigned to CuO have been shifted and broadened. As further calculated from the spectrum, the cell parameters of the CuO lattice were changed from: a=4.6890; b=3.4200; c=5.1300 for CuO to a=4.6829; b=3.4201; c=5.1429 for the Zn—CuO nanoparticles.

Without being bound by any particular theory, it is assumed that these differences in the CuO lattice parameters resulting from the reaction of the mixed precursor solution are indicative of the changes in the atomic composition of the lattice, more specifically, of the doping of $Zn^{2+}$ ions into the unit cell of the CuO crystal lattice, which replace some of the $Cu^{2+}$ ions. This leads to preferred arrangement of the Zn-doped CuO composite.

Without being bound by any particular theory it is assumed that the increased width of the diffraction patterns of Zn-doped CuO as compared to those of ZnO or CuO, indicates the formation of smaller particle grains, and is further indicative of defects in the crystal lattice, such as dislocations therein, which are assumed to account for the enhanced antimicrobial activity of the nanoparticles.

FIG. 2A presents representative XRD reflection lines of a product obtained by med-3:1 Cu:Zn precursors mixture as designated hereinabove, subjected to ultrasonic irradiation.

The obtained data clearly show the pattern of the product (spectrum) is shifted in comparison to the monoclinic CuO (lines, international powder diffraction file (PDF) (80-1916). The cell parameters of the CuO lattice were changed from: a=4.6890; b=3.4200; c=5.1300 for CuO to a=4.6829; b=3.4201; c=5.1429 for the synthesized material. Calculations of the cell parameters were performed by the Rietveld method.

Without being bound by any particular theory the observed differences in the CuO lattice parameters can be explained as a result of the changes in the atomic composition of the lattice.

Without being bound by any particular theory one of the possible explanations for this phenomenon is that during the sonochemical reaction the $Zn^{+2}$ ions are doped in the unit cell of the monoclinic CuO lattice replacing the $Cu^{+2}$ ions. Without being bound by any particular theory it is assumed that the copper-ammonia complex generation is more kinetically preferred than the zinc-ammonia complex, and this leads to formation of doped particles, as the XRD indicated that no phase of ZnO formed.

It is noted that a small shift in the XRD refractions and/or cell parameters, indicates that the main crystal lattice is substantially maintained, with only dopant amounts of Zn ions replacing Cu atoms in the lattice. These small shifts and changes, along with the absence of XRD refractions of ZnO are altogether indicative of a formation of crystal lattice Zn-doped CuO particles.

Figure 2B:
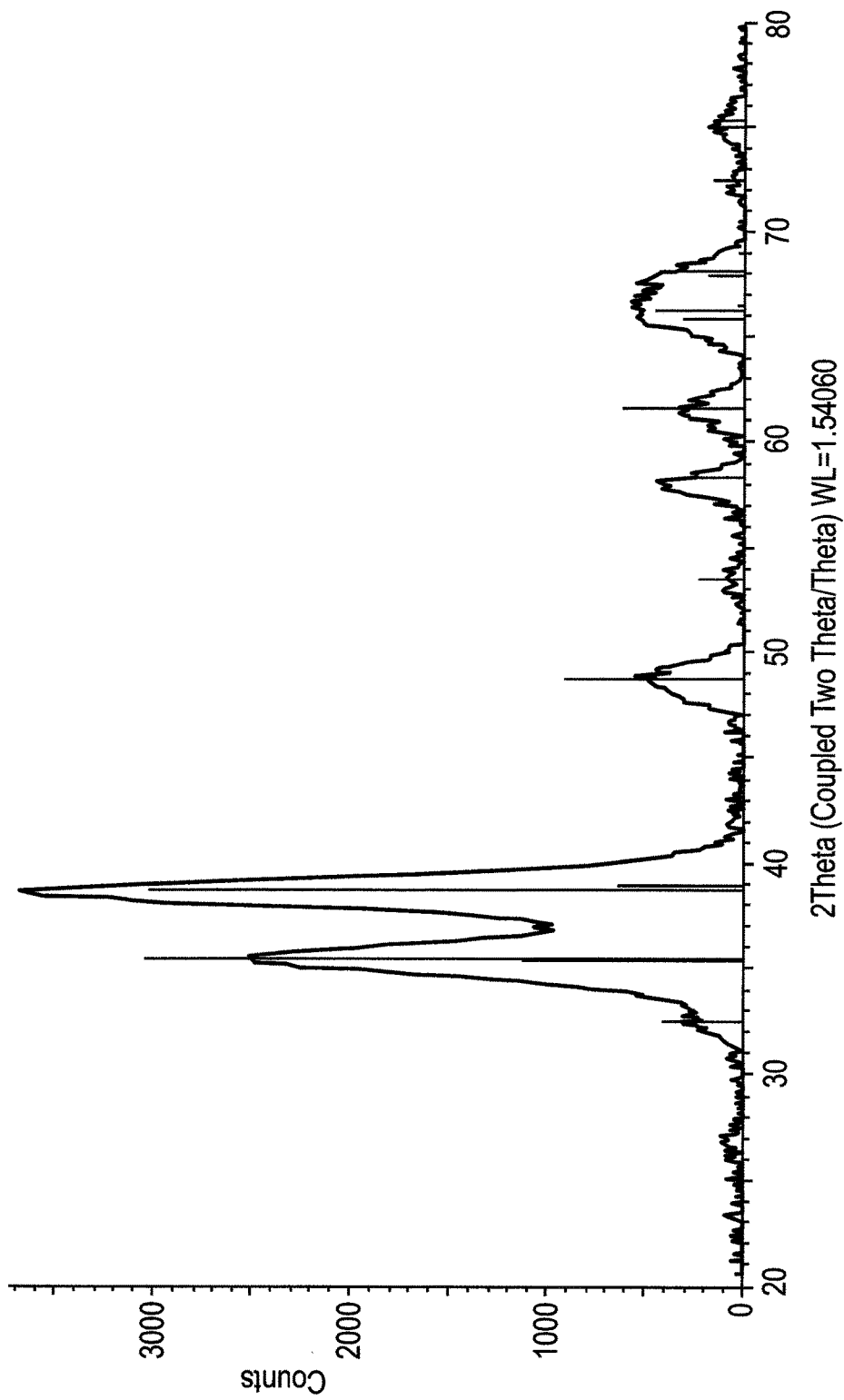

FIG. 2B presents XRD reflection lines of the product obtained upon subjecting med-3:1 Cu:Zn precursors mixture as designated hereinbelow to microwave irradiation, and show no shifts in the peaks position.

Figure 2C:
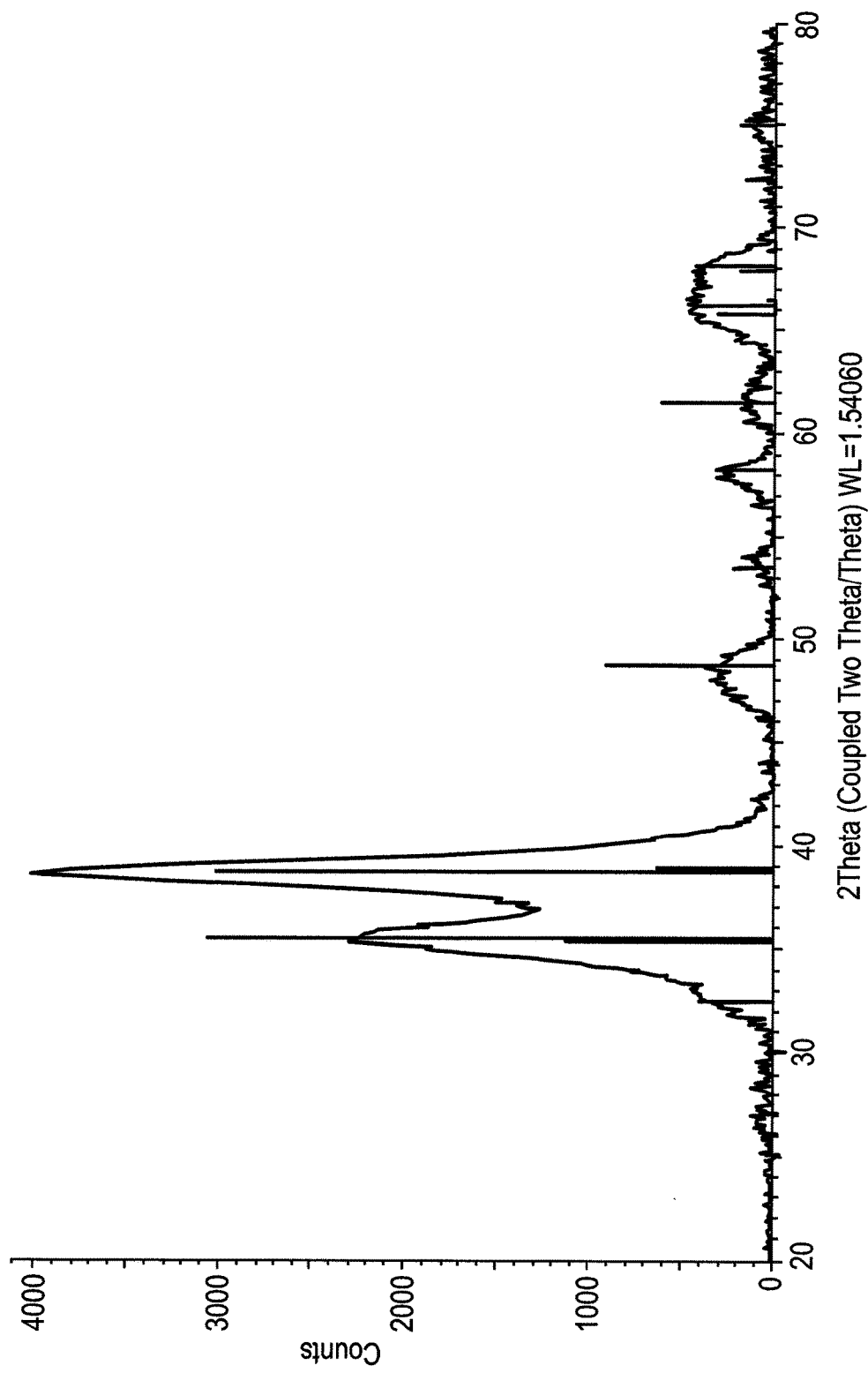

FIG. 2C presents XRD reflection lines of the product obtained upon subjecting med-3:1 Cu:Zn precursors mixture as designated hereinabove to thermal reaction, and show no shifts in the peaks position.

The obtained data presented in FIGS. 2B and 2C clearly show a monoclinic structure of CuO, with no doping of Zn ions, indicating that doping is effected by subjecting a precursor mixture to ultrasonic irradiation.

It is noted that the spectra presented in FIGS. 2B and 2C show also no peaks for ZnO nanoparticles. Without being bound by any particular theory, it is assumed that ZnO nanoparticles were not formed in these reactions due to kinetic considerations which favor formation of CuO nanoparticles, as is further discussed hereinunder.

Figure 2D:
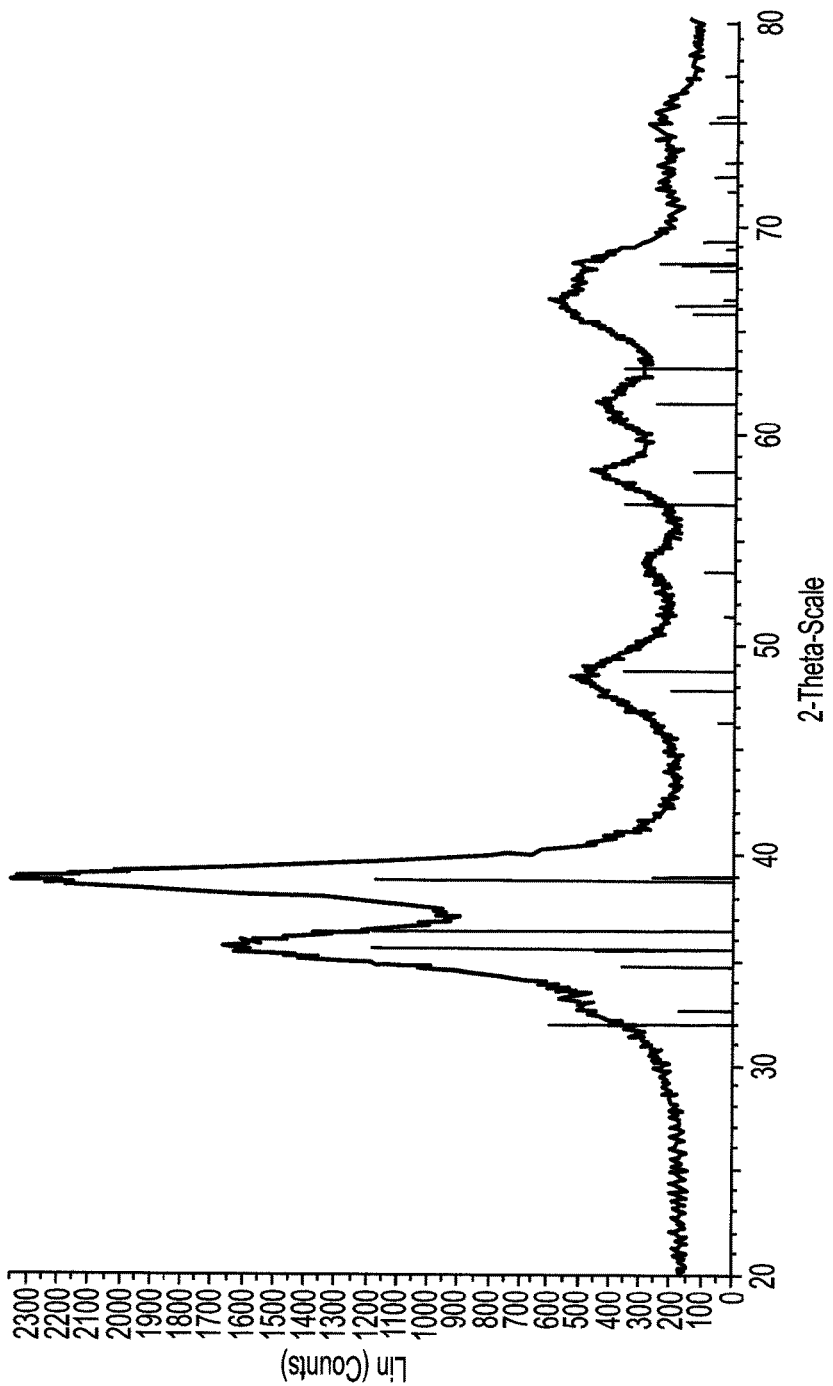

FIG. 2D presents XRD reflection lines of the product obtained upon subjecting med-4:1 Cu:Zn precursors mixture as designated hereinbelow to ultrasonic irradiation. As shown therein, all the peaks in the XRD spectra can be assigned to monoclinic crystal lattice of CuO without any shifting and broadening of the peaks, as obtained following the sonochemical reaction using pristine copper acetate precursor. The peaks at 2θ=32.47, 35.49, 38.68, 48.65, 58.25, and 61.45 are assigned to the (110), (−111), (111), (−202), (202), and (−113) reflection lines of monoclinic CuO (PDF 80-1916). No peaks under the spectrum assigned to the reflection lines of ZnO (PDF 89-7102), which are also provided for reference in FIG. 2D.

Hereinafter, Zn-doped nanoparticles describe nanoparticles prepared from a med-3:1 Cu:Zn precursors mixture, as described herein, unless otherwise indicated.

ICP Analysis:

Determination of the concentration of Cu and Zn ions in nanoparticles' coating on e.g., a cotton fabric, prepared as described in Example 1 hereinabove, was performed using ICP analysis.

Table 1 below presents the percentages of the copper and zinc ions in Zn-doped CuO nanoparticles dissolved from the fabric's coating by adding 0.5M $HNO_3$. The results regarding to deposition % in Table 1 were obtained from the reactions starting from various concentrations (i.e., "high", "medium", and "low", as indicated hereinabove) of the precursors in the solution in the presence of a fabric piece immersed therein. In all three concentrations the molar ratio of the precursors are Cu:Zn is 3:1 prior to the reaction.

The ICP results indicate that the ratio of Cu:Zn in the dissolved nanoparticles is about 8:1, that is, originating from a composite with the corresponding molar ratio of $Cu_{0.88}Zn_{0.12}O$.

TABLE 1

| Sample name | Concentration in solution (M) | | Deposition (wt %) | |
|---|---|---|---|---|
| | [$Cu^{2+}$] | [$Zn^{2+}$] | $Cu^{2+}$ | $Zn^{2+}$ |
| 3—high | 0.015 | 0.005 | 2.15 | 0.27 |
| 2—medium | 0.0075 | 0.0025 | 0.95 | 0.12 |
| 1—low | 0.00375 | 0.00125 | 0.41 | 0.05 |

Without being bound by any particular theory, it is assumed that the above results may be explained on the basis of the following reactions:

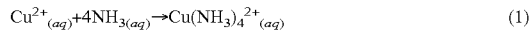

$$Cu^{2+}_{(aq)} + 4NH_{3(aq)} \rightarrow Cu(NH_3)_4^{2+}{}_{(aq)} \quad (1)$$

$$Cu(NH_3)_4^{2+}{}_{(aq)} + H_2O \rightarrow CuO_{(s)} + 2NH_4^+{}_{(aq)} + 2NH_{3(aq)} \quad (2)$$

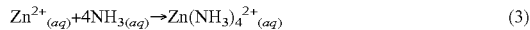

$$Zn^{2+}_{(aq)} + 4NH_{3(aq)} \rightarrow Zn(NH_3)_4^{2+}{}_{(aq)} \quad (3)$$

$$Zn(NH_3)_4^{2+}{}_{(aq)} + H_2O \rightarrow ZnO_{(s)} + 2NH_4^+{}_{(aq)} + 2NH_{3(aq)} \quad (4)$$

Without being bound by any particular theory, it is assumed that the higher deposition percentage of the copper on the coated substrate is explained by faster kinetics of $Cu(NH_3)_4^{2+}$ complex formation as compared to the rate of the $Zn(NH_3)_4^{2+}$ complex. It is therefore assumed, without being bound by any particular theory, that the difference in the kinetics of the complexes' formation drives the first step in the above mechanism more intensively.

Dissolution of Ions from the Nanoparticles:

Zn-doped CuO nanoparticles were studied with respect to their tendency to release ions into a medium.

$Cu^{2+}$ and $Zn^{2+}$ ion concentrations released from CuO and Zn:CuO nanoparticles after immersion in BH medium for 24 hours were determined (by inductively coupled plasma (ICP)), and the results are presented in Table 2 below.

TABLE 2

| | [$Cu^{2+}$] mg/L | [$Zn^{2+}$] mg/L |
|---|---|---|
| Zn—CuO nanoparticles | 99.46 | 0.58 |
| CuO nanoparticles | 99.76 | — |

Figure 3:
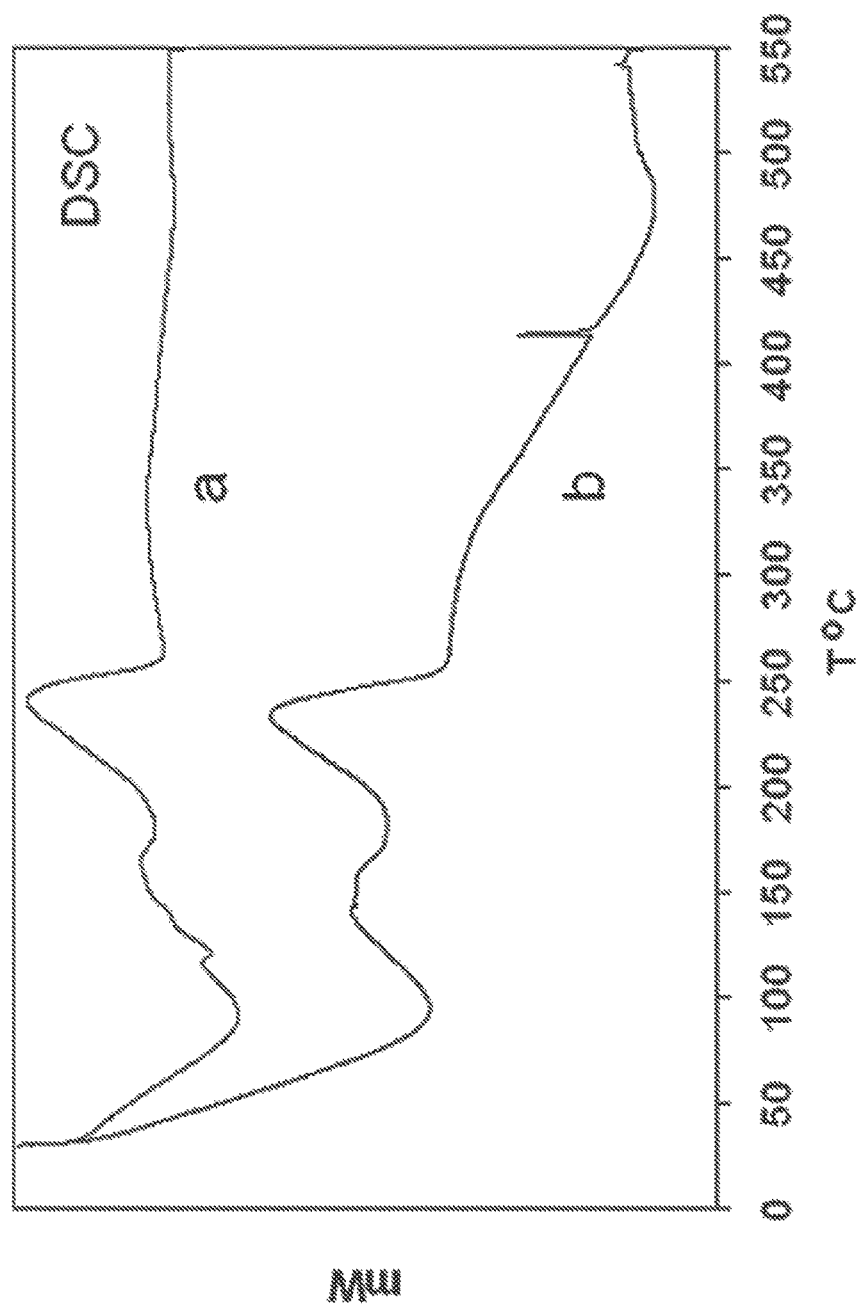
FIG. 3 presents comparative spectra obtained from DSC analysis of (3:1) Zn-doped CuO nanoparticles according to some embodiments of the present invention, upon annealing at 550° C. under both inert (spectrum a) and oxidizing conditions (spectrum b).

DSC Analysis:

FIG. 3 presents plots obtained from DSC analysis of Zn-doped CuO nanoparticles, under both inert (plot a) and oxidizing conditions (plot b), demonstrating, for both conditions, one endothermic peak at 100° C. assigned to water evaporation and two exothermic peaks, a broad peak at a temperature range of 130-165° C. and a strong sharper exothermic peak at 240° C. A sharp exothermic peak appears at 420° C. only in plot b. The exothermic peaks at 130-165° C. and 240° C. are irreversible and do not appear in a second heating cycle.

Without being bound by any particular theory, it is assumed that the two exothermic peaks indicate the re-ordering of the crystals and the rearrangements of the vacancies formed due to the doping of Zn into the CuO crystal. It may further be assumed that in addition to crystalline Zn-doped CuO, an amorphous product is also obtained.

The peak at 240° C. may be regarded as indicative of the crystallization of the product.

Without being bound by any particular theory, it is assumed that the appearance of the irreversible, very sharp peak at 420° C. under oxidizing conditions indicates filling of the defects in the crystal lattice by oxygen.

Figure 4A:
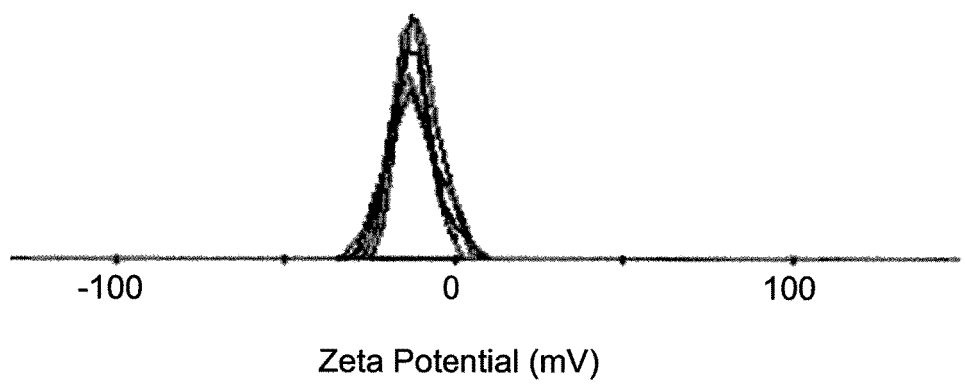
FIGS. 4A-B present a superposition of spectra obtained from several measurements of Zeta potential of Zn-doped CuO nanoparticles according to some embodiments of the present invention (FIG. 4A) and (non-doped) CuO nanoparticles (FIG. 4B) in Brain-Heart medium.
Figure 4B:
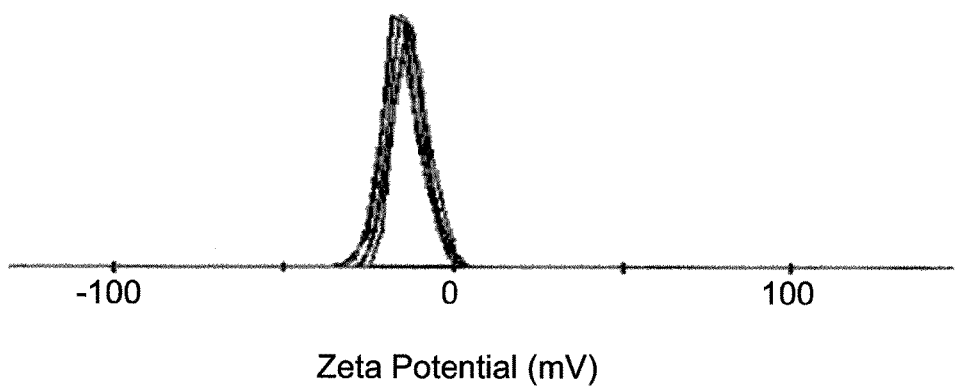

Zeta Potential Measurements:

FIG. 4 shows zeta potential measurements revealing that the average charges of the Zn-doped CuO nanoparticles and CuO nanoparticles were −12 mV and −13.9 mV, respectively.

Figure 5:
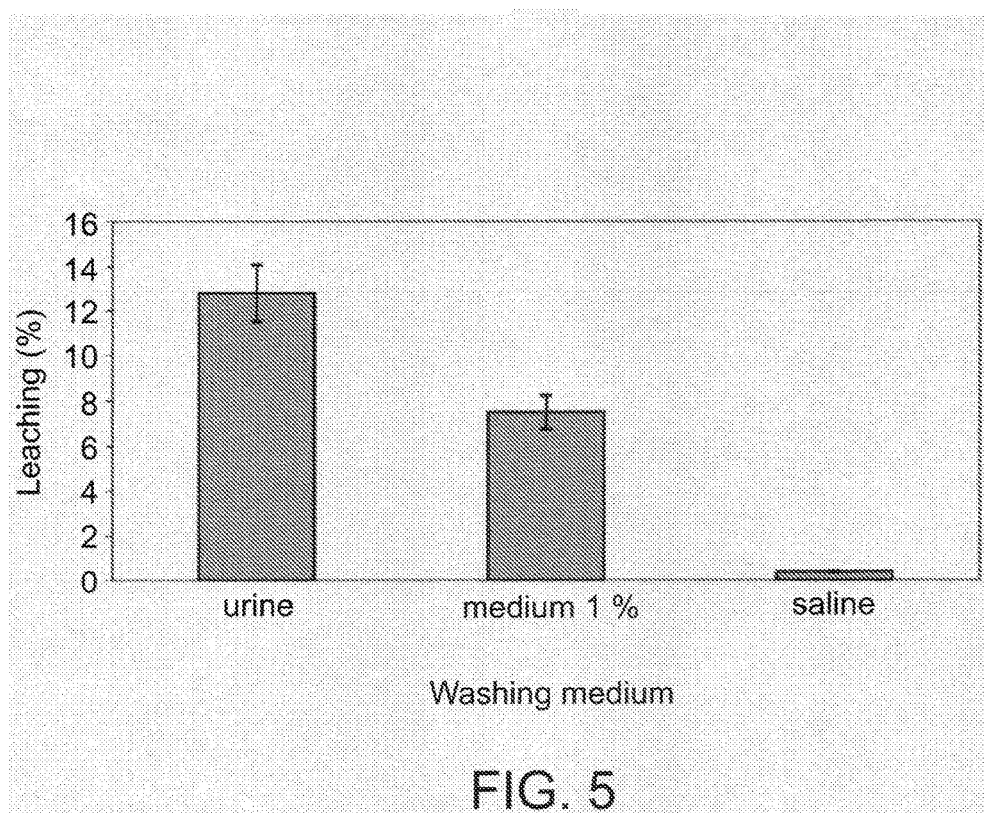
FIG. 5 is a bar graph showing the weight loss percentage of catheters coated with Zn-doped CuO nanoparticles according to some embodiments of the present invention immersed in saline, 1% growth medium and artificial urine.

FIG. 5 presents a bar graph bar showing the leaching properties of catheters coated with Zn-doped CuO nanoparticles immersed in different media (i.e. saline, 1% growth medium and artificial urine) with the highest loss of the coating in urine i.e., about 12% and the most minimal loss in saline medium, i.e., less than 1%. No nanoparticles were detected in the solution by electron microscope or dynamic light scattering (data not shown).

FIG. 6 shows the SEM measurements of cotton fabric coated with Zn-doped CuO nanoparticles carried out in order to study the morphology of the cotton fibers before and after the deposition reaction.

Figures 6A, 6B:
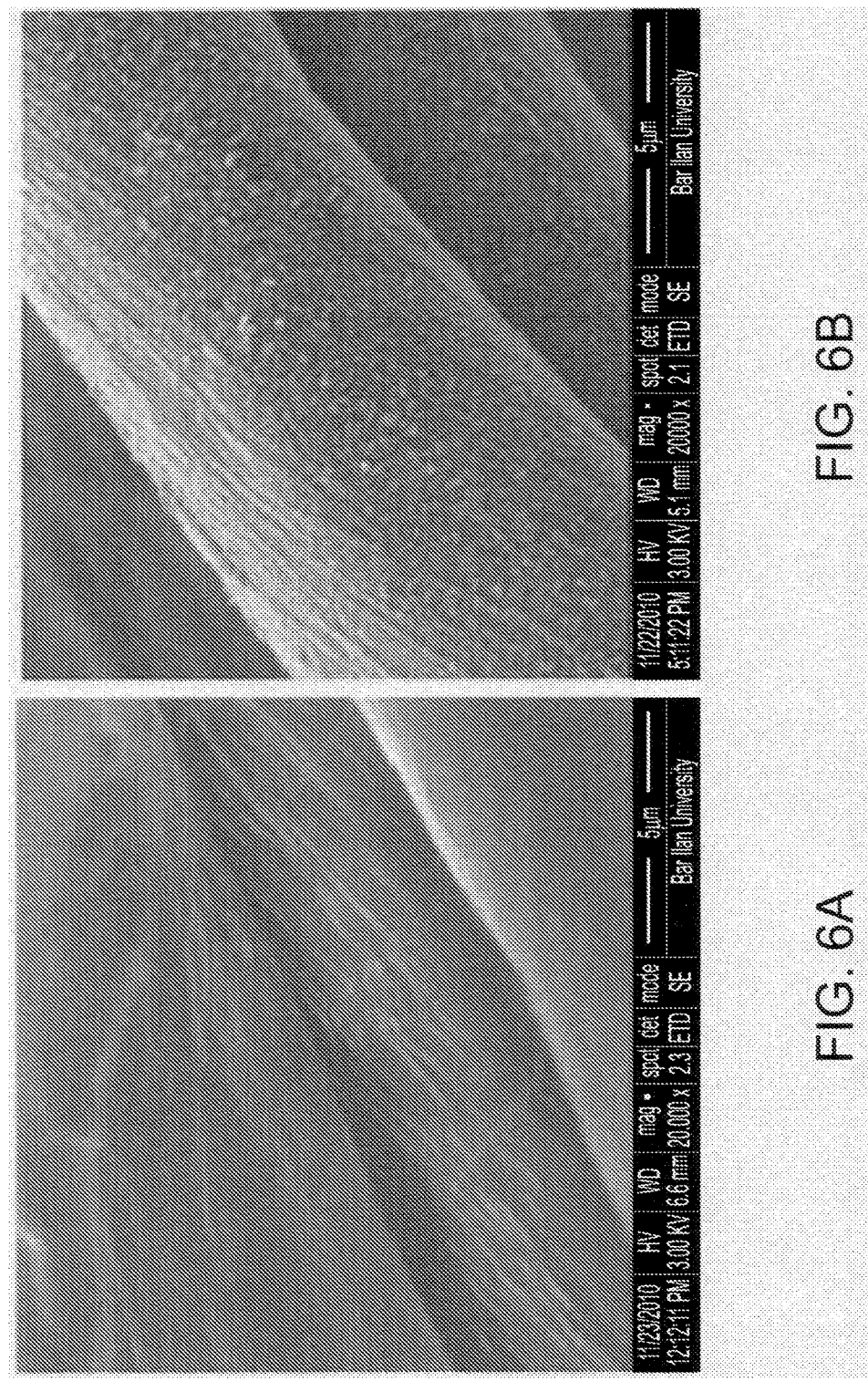
FIGS. 6A-B present SEM images of bare cotton fabric (FIG. 6A) demonstrating a smooth texture of the fabric, and cotton fabric coated with Zn-doped CuO nanoparticles according to some embodiments of the present invention (FIG. 6B) using the ultrasonic irradiation, demonstrating the homogeneously coating thereon.

FIG. 6A demonstrates the smooth texture of the pristine cotton fabric.

As shown in FIG. 6B, the fibers are homogeneously coated with Zn-doped CuO nanoparticles, having a uniform and very high coating density.

FIGS. 7A-C show HR-SEM measurements performed for determining the particles size of the Zn-doped CuO nanoparticle coating on the cotton fabric obtained from different concentrations of the corresponding metal acetate precursors.

As shown in FIG. 7A for the "medium" (as defined hereinabove) concentration of the precursors, nanoparticle coating on the cotton fabric of 30 nm were observed.

As shown in FIG. 7B for the "high" (as defined hereinabove) concentration of the precursors, nanoparticle coating on the cotton fabric of 80 nm were observed.

As shown in FIG. 7C for the "low" (as defined hereinabove) concentration of the precursors, nanoparticle coating on the cotton fabric of 30 nm were observed.

FIG. 7D presents a histogram presenting the size distribution of the particles deposited on the coated fibers for the "medium" concentration of the precursors as obtained by the "Scion image" Software, demonstrating that the diameter of about 70% of the primary nanoparticles was in the range of 25-35 nm.

FIG. 8B present HR-SEM images showing a uniformly coated tooth surface with Zn-doped CuO nanoparticles compared to a bare tooth.

FIG. 8C present HR-SEM images showing a uniformly coated tooth surface with CuO nanoparticles compared to a bare tooth.

For a reference, FIG. 8A presents HR-SEM image of an uncoated tooth.

FIG. 8D presents a histogram showing the size distribution of the Zn-doped CuO nanoparticles deposited on the coated tooth as obtained by the "Scion image" software, demonstrating that the average diameter of the Zn-doped CuO nanoparticles is about 30 nm.

FIG. 8E presents a histogram showing the size distribution of the CuO nanoparticles deposited on the coated tooth as obtained by the "Scion image" software, demonstrating that the average diameter of the CuO nanoparticles is about 70 nm.

FIGS. 9A-B presents a photograph showing an uncoated catheter (FIG. 9A) and a catheter coated with Zn-doped CuO nanoparticles (FIG. 9B).

FIG. 10A presents an HR-SEM image showing Zn-doped CuO nanoparticles (sized 80-120 nm) coating the external surface of the catheter.

FIG. 10B presents an HR-SEM image showing Zn-doped CuO nanoparticles (sized 80-120 nm) coating the internal surface of the catheter.

Figures 11A, 11B, 11C:
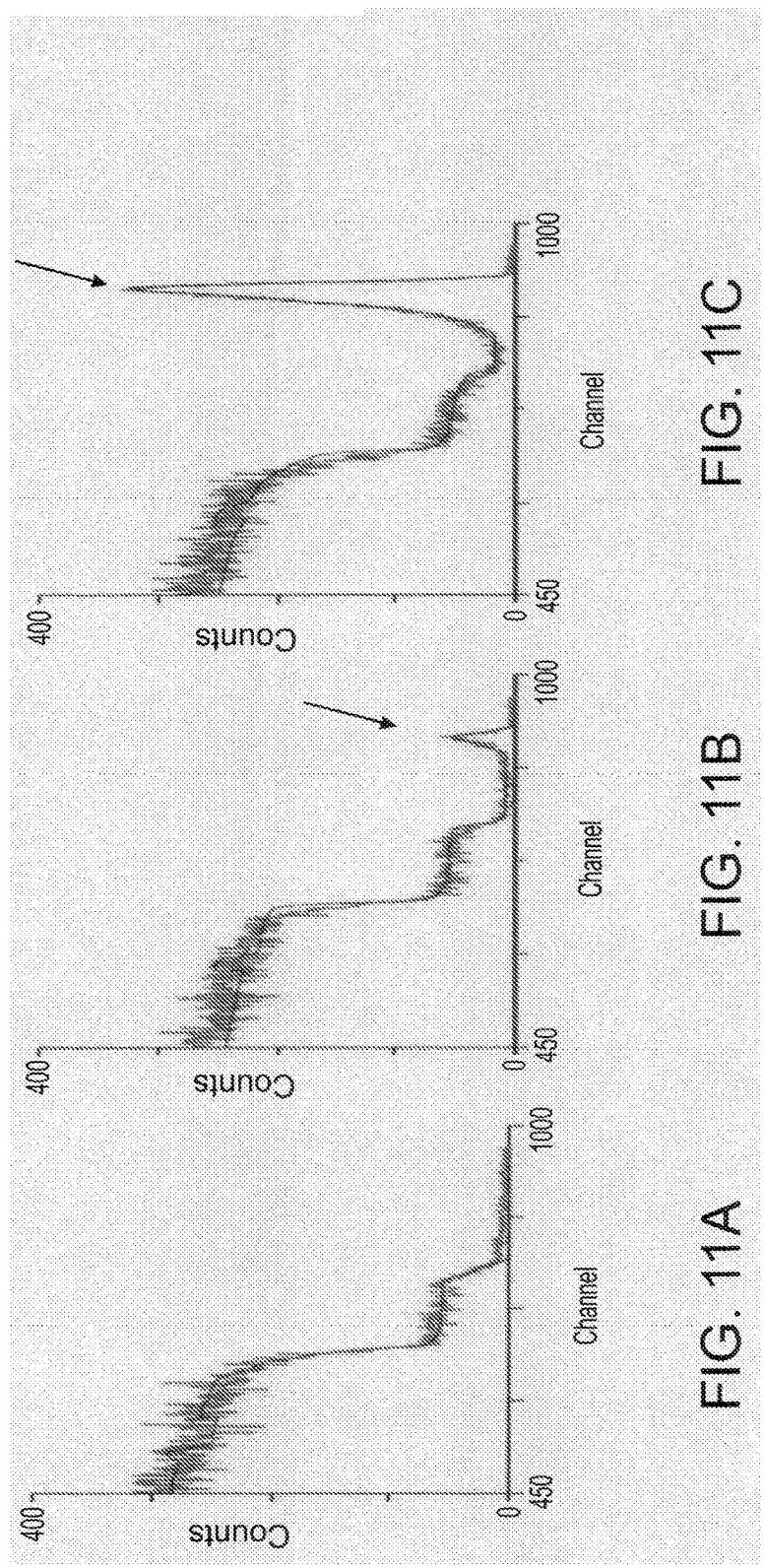
FIGS. 11A-C present spectra showing superposition of measured and simulated RBS analysis.

FIG. 11A shows measured and simulated RBS spectra of uncoated teeth surface, for a reference.

FIG. 11B shows measured and simulated RBS spectra demonstrating the coatings of Zn-doped CuO nanoparticles on artificial teeth, and further indicating with an arrow the presence of Cu, as being the only metal element on the coated teeth.

FIG. 11C shows measured and simulated RBS spectra demonstrating the coatings of CuO nanoparticles on teeth, and further indicating with an arrow the presence of Cu as being the only metal element on the coated teeth.

Figure 12B:
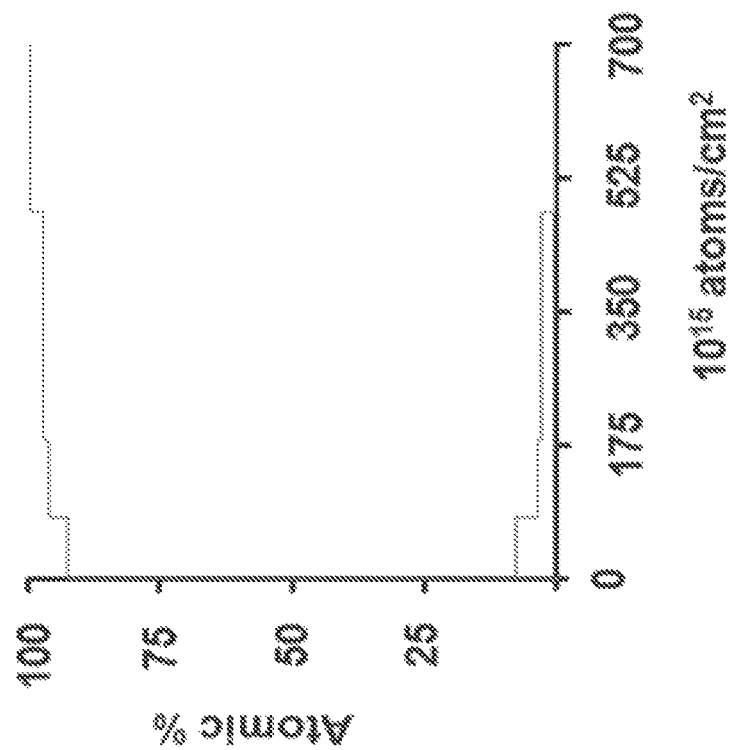
FIGS. 12A-B present RBS analysis spectra of tooth surfaces coated, by the ultrasonic irradiation, with Zn-doped CuO (FIG. 12A) and CuO nanoparticles (FIG. 12B), showing depth compositional of the tooth substrate (upper graphs) and depth compositional the nanoparticle coating (lower graphs).
Figure 12A:
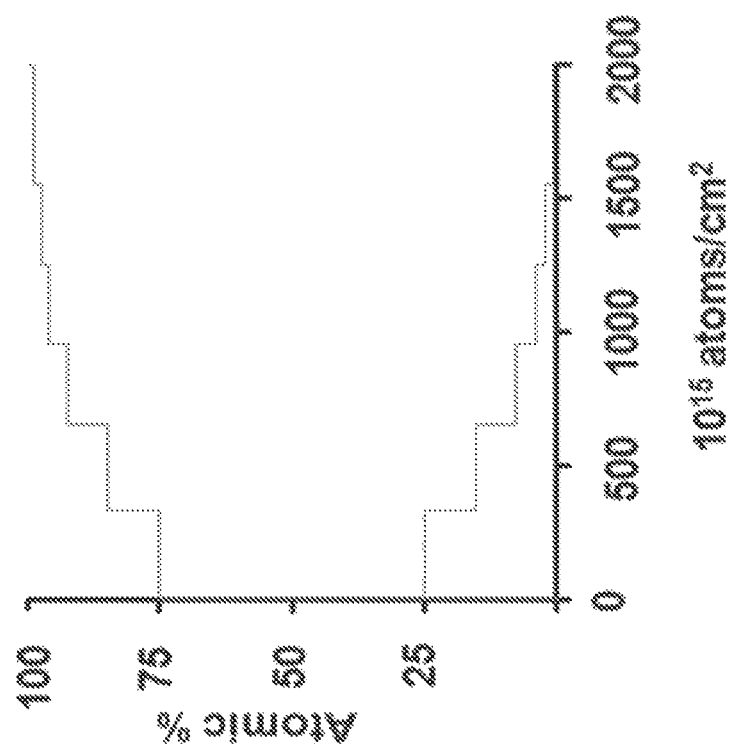

FIGS. 12A-B present RBS spectra showing compositional penetration depths of the tooth surfaces coated with Zn-doped CuO (FIG. 12A) and CuO nanoparticles (FIG. 12B) indicating: (i) the formation of coating layers formed by Zn-doped CuO nanoparticles and CuO nanoparticles, with variations in the NP coating thickness; (ii) a deeper penetration of Zn-doped CuO nanoparticles coating (over 1500×$10^{15}$ atoms/cm$^2$) compared to coating with CuO nanoparticles (about 500×$10^{15}$ atoms/cm$^2$); (iii) higher amount of the Cu in the Zn-doped CuO coating compared to the CuO nanoparticle coatings; (iv) absence of $Zn^{2+}$ ions on both coating.

FIG. 13A presents a FIB-SEM image of uncoated tooth, for reference.

FIG. 13B presents a FIB-SEM image showing the layers of the Zn-doped CuO nanoparticles covering the tooth surface. The image shows a continuous coating of the Zn-doped CuO nanoparticles, with a 53.9 nm layer thick along the grooves on the tooth surfaces.

FIG. 13C presents a FIB-SEM image showing the layers of the CuO nanoparticles covering the tooth surface. The image shows a continuous coating of the CuO nanoparticles, with a 44.6 nm layer thick along the grooves on the tooth surfaces.

Example 3

ESR Measurements

ROS production of aqueous suspensions of ZnO, CuO, and Zn-doped CuO nanoparticles (e.g., 1 mg/ml) obtained from the med-3:1 Cu:Zn precursors mixture described herein were detected using the electron spin resonance (ESR) spin trapping technique coupled with the spin traps: 5,5-dimethyl-1-pyrroline-N-oxide (DMPO) (0.02 M; Sigma, St. Louis, Mo.)—for the hydroxyl radicals and the superoxide anions and 2,2,6,6-tetramethylpiperidine (TEMP) (0.02 M; Sigma, St. Louis, Mo.)—for the singlet oxygen.

The DMPO reacts with hydroxyl radicals and superoxide anion radicals, to produce DMPO-OH, a relative stable and paramagnetic species, detectable in the ESR technique by producing a typical signal of 1:2:2:1 quartet (Makino, K. et al. *Int. J. Rad. Appl. Instrum* [C] 1991, 37, 657-665).

The aqueous suspensions of nanoparticles were added to the spin trap (e.g., DMPO) and drawn by a syringe into a gas permeable Teflon capillary (Zeus Industries, Raritan, N.J.) and then inserted into a narrow quartz tube that is kept open at both ends. The tube was then placed in the ESR cavity and the spectra were recorded on a Bruker ESR 100d X-band spectrometer. The ESR measurement conditions were as follows: frequency, 9.74 GHz; microwave power, 20 mW; scan width, 65 Gauss; resolution, 1024; receiver gain, $2\times10^5$; conversion time, 82 millisecond; time constant, 655 millisecond; sweep time, 84 seconds; scans, 2; modulation frequency, 100 kHz. After acquisition, the spectrum is processed using Bruker WIN-ESR software version 2.11 for baseline correction. The peak intensity was calculated by double integration of the peak signals, and the intensity is expressed in arbitrary units.

In order to better distinguish between the hydroxyl radicals and the superoxide radicals produced in the NP suspensions, competition experiments using a scavenger of a specific ROS can be performed.

Dimethyl sulfoxide (DMSO; Sigma-Aldrich) was added (5% v/v) to the nanoparticle suspensions, serving as a hydroxyl radical scavenger.

TEMP reacts with singlet oxygen leading to the formation of the stable species 2,2,6,6-tetramethyl-4-piperidone-N-oxyl (TEMPO), with a characteristic ESR spectrum comprised of equally intensity triplet. Since the hydroxyl radicals and superoxide anions react with the nitroxyl groups of TEMPO, thereby reversing it to TEMP, further addition of DMPO to the suspensions was needed, so as to remove hydroxyl radicals and superoxide anions from the suspensions. Heated NP samples at various temperatures in air or nitrogen, as indicated hereinabove for the DSC analysis, were further used for subsequent ESR analysis of ROS formation.

All the data presented hereinbelow are expressed as an average of at least three identical experiments.

The ESR technique revealed the ROS produced by the different nanoparticles.

FIG. 14A presents ESR spectra as detected following the addition of DMPO to the suspensions of ZnO, CuO and Zn-doped CuO nanoparticles, correlated to the signal of the DMPO-OH spin adducts originating from the same suspensions. It is shown that the signal of the DMPO-OH spin adducts originating from the suspension of Zn-doped CuO. is substantially higher than those of ZnO or CuO nanoparticles.

As can be seen in FIG. 14B the addition of DMSO reduced the quartet signal, but did not eliminate it completely, thus suggesting that Zn-doped CuO nanoparticles generated both the superoxide anion and hydroxyl radicals.

FIG. 14B further presents features (marked by arrows) corresponding to the DMPO-CH$_3$ adduct formed from by trapping the methyl radicals, being formed from the initiation of DMSO by the hydroxyl radical, by the DMPO.

Figure 15:
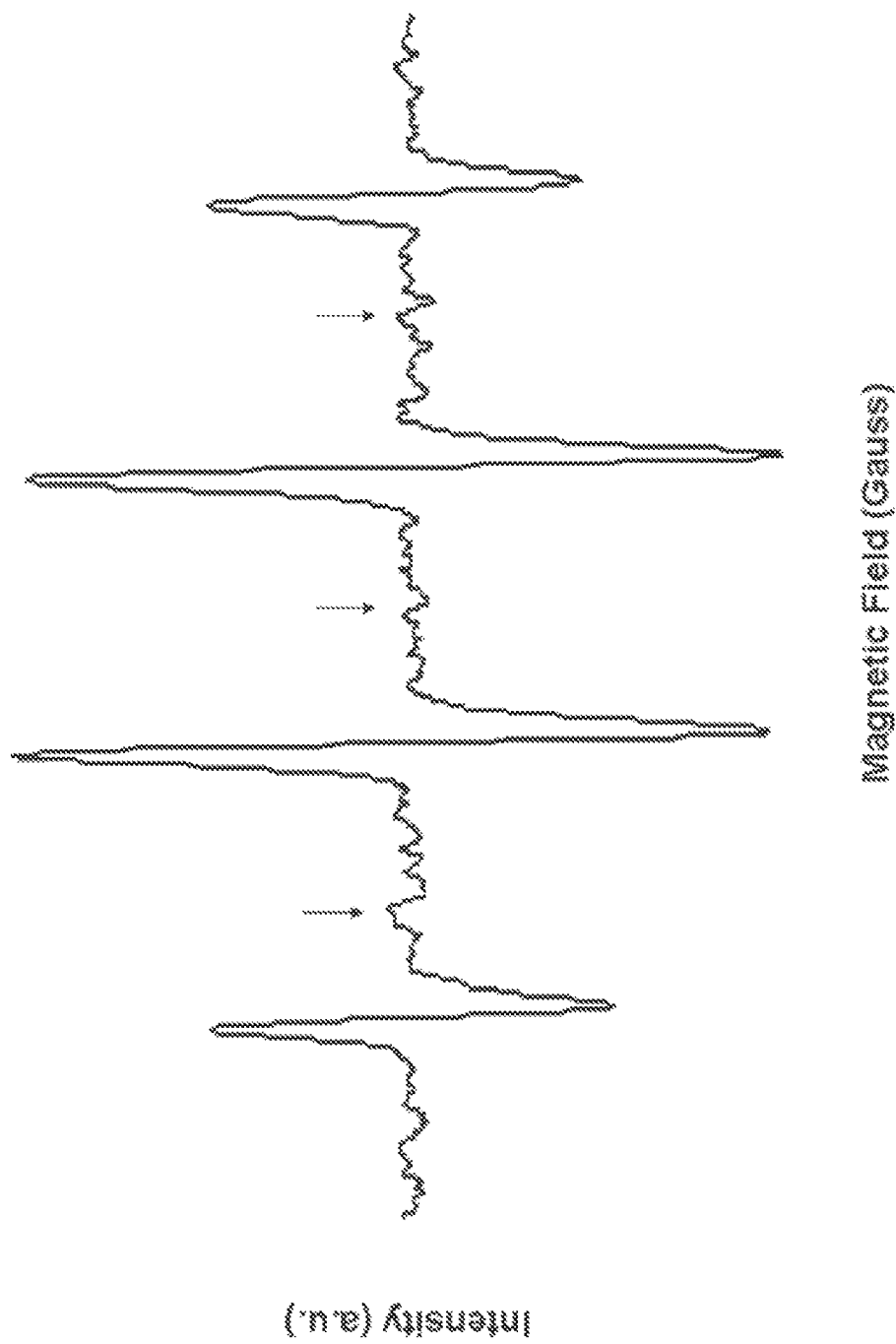
FIG. 15 presents an ESR spectrum detected following addition of TEMP and DMPO to Zn-doped CuO nanoparticle-containing suspension, with the arrows marking signal features corresponding to singlet oxygen.

FIG. 15 presents ESR signals as detected following the addition of TEMP and DMPO to the Zn-doped CuO nanoparticle suspensions.

As marked with arrows in FIG. 15 a weak triplet signal monitoring singlet oxygen was detected in a Zn-doped CuO suspension, indicating the presence of singlet oxygen in the suspension.

ROS production by the coated bandages was stable for at least 6 months after their preparation (data not shown).

ESR measurements were also performed on samples heated at various temperatures in air or nitrogen (see, DSC measurements).

FIG. 16A shows the ESR signal intensity as observed for the Zn-doped CuO nanoparticles for a reference.

As shown in FIG. 16B no substantial reduction in the ESR signal intensity was observed for the Zn-doped CuO samples being formerly heated to 300° C. under air.

FIG. 16C shows an ESR signal with reduced intensity for the suspension of the Zn-doped CuO sample being formerly heated to 550° C. under air.

FIG. 16D shows a complete diminishing of the ESR signal for the suspension of the Zn-doped CuO sample being formerly heated to 550° C. under nitrogen.

FIG. 16E shows the ESR signal of DMPO solution without the presence of the Zn-doped CuO nanoparticles, for a reference.

Without being bound by any particular theory, it is assumed that the results presented herein indicate that heating the Zn-doped CuO to elevated temperatures results in annealing and re-organization of the crystal lattice and thereby the loss of the defects, mainly dislocations, that are responsible for ROS formation in the Zn-doped CuO nanoparticles-containing samples.

Example 4

Antimicrobial Activity

Antimicrobial Viable Count Tests:

The antibacterial activity of the metal oxide nanoparticles-coated substrates was tested against various bacterial stains.

Cultures of a bacterial strain are grown overnight in a medium growth (e.g., NB, LB) at 37° C. with aeration and are next transferred into a fresh medium at an initial optical density (OD) at the suitable wavelength (e.g., 595 or 660 nm, Synergy 2, BioTek Instruments) of 0.1. When the OD reaches 0.3 nm, i.e. the log phase (about $10^8$ CFU/ml; CFU: colony-forming unit), the cells are harvested by centrifugation and washed twice with a saline solution (0.85% NaCl) at pH 6.5. The tested agent, (e.g., 1 mg/ml of: $Zn^{+2}$ ions, $Cu^{+2}$ ions ZnO nanoparticles, CuO nanoparticles, Zn-doped CuO nanoparticles, coated substrate sized e.g., 2×3 cm², with any one of the indicated nanoparticles) is next placed in a vial (e.g., with diameter of 2.5 cm) containing bacteria in saline (e.g., of 4 ml). The microbial suspensions are incubated for up to 3 hours at 37° C. with agitation (e.g., about 170 rpm), and an aliquot (e.g., 100 µl) is then taken at different time intervals (e.g., 0, 10 and 30 minutes; 1, 2, and 3 hours) and plated after serial 10-fold dilutions in saline on a solid medium-agar (e.g., MH-agar, NB-agar) poured in flat-bottomed petri plates. The plates are next incubated for up to 24 hours at 37° C. The viable microbial cell number at the specified times is recorded by counting and averaging the number of bacterial colonies grown on the plate, obtained from the triplicates of three independent experiments, multiplied by the dilution factor and expressed as colony forming units (CFU). Reduction in viability of the bacteria is determined by $\log(N/N_0)$, where $N_0$ and N denote the number of CFUs at the initial ($N_0$) and following treatment (N). Non-coated substrate is used as control.

In exemplary procedures, the antimicrobial viable count tests were examined on the following bacterial strains: *E. coli* 1313, *S. aureus* 195, MDR *E. coli*, and MRSA, as indicated hereinabove.

In exemplary procedures, the antimicrobial viable count tests were examined for probing the antifungal activity against a clinical isolated *Candida albicans*

In exemplary procedures, the antibacterial agent was a substrate (e.g, cotton fabric, artificial tooth, pediatric silicon urinary catheter) coated with Zn-doped CuO nanoparticles thereon.

Antibacterial Growth Tests:

*S. mutans* 700610 was grown aerobically at 37° C. in BH overnight and were then diluted (1:100) in fresh media, grown for 8 hours at 37° C. (with shaking (250 rpm). Zn-doped CuO or CuO nanoparticles (1 mg/ml) were added to sterile polypropylene tubes (Greiner Bio-One), to which the appropriate volume of the bacterial solution (about $10^7$ CFU/ml, OD of 0.01 at 595 nm) of *S. mutans* culture was added. Next, an aliquant of 100 µl of each tested cell suspension was added to a well in a 96-well plate that was incubated for 24 hours at 37° C. The bacterial growth was determined spectrophotometrically by measuring the absorbance ($OD_{595}$, Synergy 2, BioTek Instruments) at specified intervals during the incubation period.

In some assays, the $Zn^{2+}$ and $Cu^{2+}$ ions in their concentrations as released from the corresponding nanoparticles in BH growth medium, were tested.

In some assays, artificial teeth coated with Zn-doped CuO or CuO nanoparticles was tested.

In some assays a mixture of $Zn^{2+}$ ions in their concentration as released from Zn-doped CuO nanoparticles suspended in a growth medium (BH) with CuO nanoparticles (1 mg/ml) was tested.

Transmission Electron Microscopy (TEM) of Treated Bacteria:

In exemplary procedures, for examining the morphological changes of the bacterial cells following antibacterial treatment, samples of *S. mutans* 700610 cultures were centrifuged and washed immediately after a treatment without (control) and with either CuO or Zn-doped CuO nanoparticles (0.1 mg/ml). The samples were then fixed in 25% glutaraldehyde/paraformaldehyde (Sigma-Aldrich)] in a cacodilate buffer (Sigma-Aldrich) at room temperature (about 25° C.) for 1 hour. The samples were then washed with a cacodilate buffer and fixed in 1% osmium tetraoxide (Sigma-Aldrich). Sample embedding was carried out using a standard protocol as previously described by S. Croft [*Methods Molec. Biol. Elec. Microsc. Methods Prot.* 1999, 117]. 60 nm thick slices were cut with a diamond knife (LBR ultratome III). The slices were deposited on bare 200 mesh grids, and stained with 2 wt % uranyl acetate (Sigma-Aldrich) for 5 minutes. Finally, the grids were dried in a desiccator and next examined using a JEOL 1200Ex TEM.

Penetration of Nanoparticles into the Bacterial Cells:

In exemplary procedures, for examining the penetration of nanoparticles into the bacterial cells, (e.g., *S. mutans*) at a final concentration of $OD_{595}$=0.15 (approximately $1.5 \times 10^8$ CFU/ml) in BH medium was suspended with 1 mg/ml of either CuO or Zn-doped CuO nanoparticles. After 24 hours of incubation at 37° C., the suspensions were placed on glass slides and treated with polylysine (Sigma-Aldrich) for 1 hour. Next, the slides were washed five times with $ddH_2O$, and the bacterial cells that were attached to the surface were treated with ice-cold trichloroacetic acid (TCA, Sigma- Aldrich) to cause lysis. The internal content of the bacteria was probed with ICP measurements to diagnose whether the nanoparticles had penetrated the bacteria.

Intracellular ROS Assays:

In exemplary procedures, for the detection of ROS production upon exposure to either Zn-doped CuO or CuO nanoparticles, the bacterial cells (e.g., *S. mutans* 700610) were pre-incubated with 10 µM of the dye 5- (and 6-)chloromethyl-2,7-dichlorodihydrofluorescein diacetate, acetyl ester (CM-DCFH-DA; Invitrogen, Molecular Probes) in PBS for 30 minutes thereby allowing the dye to enter the cells.

DCFH-DA can cross the cell membrane into the cell and is hydrolyzed by intracellular esterases to nonfluorescent DCFH. In the presence of ROS, DCFH is oxidized to highly fluorescent dichlorofluorescein (DCF). Therefore, the ROS concentration in the cell is directly proportional to the fluorescent intensity of DCF.

The samples were analyzed by fluorescence spectrophotometer (BioTek Synergy) II for emission at 530 nm using an excitation source at 485 nm. Untreated cells and DCFH-DA cells pre-incubated with $H_2O_2$ (100 µM) for 30 minutes were used as the negative and positive controls, respectively.

Lipid Peroxidation Assays:

Lipid peroxidation is a signature of ROS damage, which often occurs in response to oxidative stress and leads to lipid hydroperoxide formation and can be detected by assaying malondialdehyde-bis-(dimethylacetal)1,1,3,3-tetramethoxypropan (MDA), an oxidation product of polyunsaturated fatty acids and a metabolic marker for lipid peroxidation and metabolic cell damage.

In exemplary procedures, a homogenate was obtained by lysing $5.0 \times 10^6$ bacterial cells (e.g., *S. mutans* 700610) cultured overnight with or without 1 mg/ml of Zn-doped CuO or CuO nanoparticles with 10% ice-cold TCA. Untreated samples of *S. mutans* and $H_2O_2$ (1 mM) served as controls. The lysis mixture was centrifuged for 15 seconds at 14,000 rpm (centrifuge model 5418, Eppendorf). Aliquots (1 ml) of supernatant were added to 1 ml of 0.6% 2-Thiobarbituric acid (TBA, Sigma-Aldrich) and heated in a boiling water bath for 10 minutes. The samples were cooled, and the chromogenic complex formed by TBA and MDA (Sigma-Aldrich) binding was determined by absorbance at 535 nm (Ultrospec 2100 pro, Amersham Biosciences).

Results:

Table 3 summarizes the antibacterial properties of cotton fabrics coated with ZnO, CuO, and the Zn-doped CuO nanoparticles tested against *E. coli* 1313, and *S. aureus* 195.

TABLE 3

| Treatment | Duration of treatment [min] | | |
|---|---|---|---|
| | 0 | 10 | 30 |
| *S. aureus* | | | |
| Uncoated fabric | $1.4 \times 10^8$ | $2.6 \times 10^8$ | $1.1 \times 10^8$ |
| Zn—CuO | $2.5 \times 10^8$ | $1.6 \times 10^2$ | 1 |
| CuO | $1.7 \times 10^8$ | $1.4 \times 10^6$ | 1 |
| ZnO | $2.3 \times 10^8$ | $2.2 \times 10^7$ | $1.7 \times 10^5$ |
| *E. coli* | | | |
| Uncoated fabric | $2.5 \times 10^8$ | $2.4 \times 10^8$ | $2.4 \times 10^8$ |
| Zn—CuO | $2.6 \times 10^8$ | $1 \times 10^3$ | $1.7 \times 10^2$ |
| CuO | $2.5 \times 10^8$ | $2.6 \times 10^8$ | $2 \times 10^8$ |
| ZnO | $2.5 \times 10^8$ | $2.3 \times 10^8$ | $2.1 \times 10^8$ |

As depicted in Table 3, an inhibition of 6.1 and 5.37 orders of magnitude (logs) is observed for *S. aureus* and *E. coli*, respectively for both bacterial strains, after only 10 minutes of treatment with Zn-doped CuO nanoparticles (obtained from the "medium" concentration as defined hereinabove in the Sample Preparation).

Fabrics coated with pristine CuO or ZnO induced much weaker antibacterial effect with almost no antibacterial activity on the *E. coli* strains. The antibacterial activity of the fabric coated with Zn-doped CuO nanoparticles on the *S. aureus* was about 10,000 to 100,000 times higher than that of pristine ZnO or CuO nanoparticles coating.

Figure 17A:
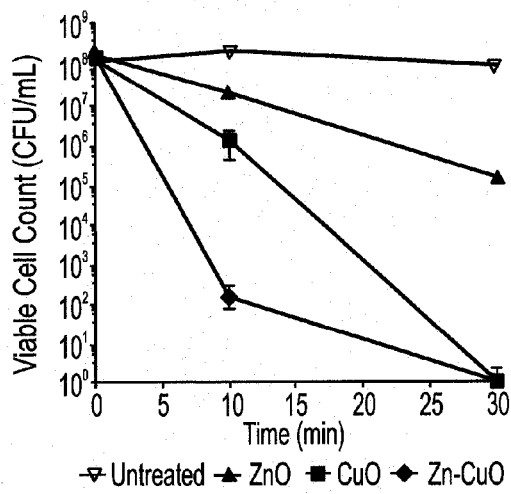
FIGS. 17A-D present comparative plots showing the effect of coating a fabric with Zn-doped CuO, CuO, and ZnO nanoparticles, compared with uncoated fabric (control), on the viable count of *Staphylococcus aureus* (FIG. 17A), *Escherichia coli* (FIG. 17B), resistant MRSA (FIG. 17C), and MDR *E. coli* (FIG. 17D), after 30 minutes of treatment in nutrient broth (NB) media.
Figure 17B:
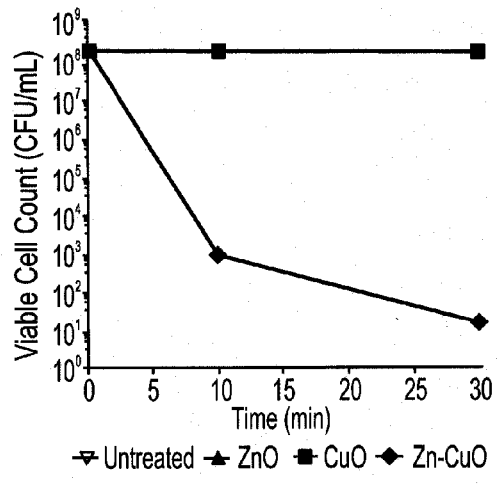

The antibacterial results, as depicted in Table 3, are further visualized in FIG. 17A (for *S. aureus*) and in FIG. 17B (for *E. coli*).

Table 4 summarizes the antimicrobial activity of cotton fabrics coated with Zn-doped CuO nanoparticles against Methicillin resistant *S. aureus* (MRSA) and multi-drug resistant (MDR) *E. coli*, selected for being highly resistant to many of the commercially available antibiotics and extremely difficult to eradicate.

TABLE 4

| Treatment | Duration of treatment [min] | | | |
|---|---|---|---|---|
| | 0 | 5 | 10 | 30 |
| Methicillin resistant *S. aureus* | | | | |
| Clean fabric | $5.5 \times 10^8$ | $3.4 \times 10^8$ | $2.1 \times 10^8$ | $2.2 \times 10^8$ |
| Zn—CuO | $5.5 \times 10^8$ | $2.5 \times 10^7$ | 1 | 1 |
| CuO | $5.5 \times 10^8$ | $2.4 \times 10^8$ | $2 \times 10^5$ | 1 |
| ZnO | $5.5 \times 10^8$ | $2.1 \times 10^8$ | $0.9 \times 10^8$ | $1.7 \times 10^8$ |
| MDR *E. coli* | | | | |
| Clean fabric | $1.2 \times 10^8$ | $1.4 \times 10^8$ | $1.2 \times 10^8$ | $1.1 \times 10^8$ |
| Zn—CuO | $1.2 \times 10^8$ | $5.3 \times 10^7$ | $2 \times 10^3$ | 1 |
| CuO | $1.2 \times 10^8$ | $1 \times 10^8$ | $3.8 \times 10^7$ | 1 |
| ZnO | $1.2 \times 10^8$ | $1.4 \times 10^8$ | $1.4 \times 10^8$ | $1 \times 10^8$ |

Figure 17C:
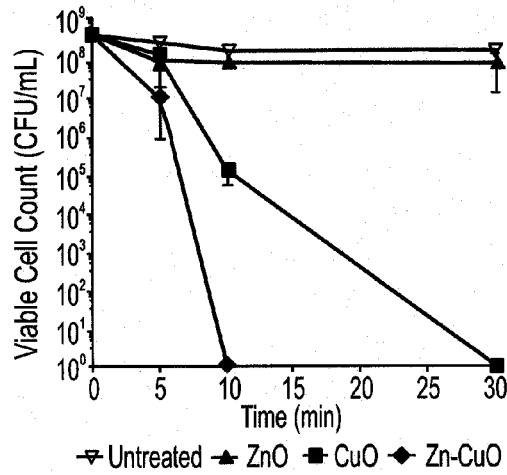
Figure 17D:
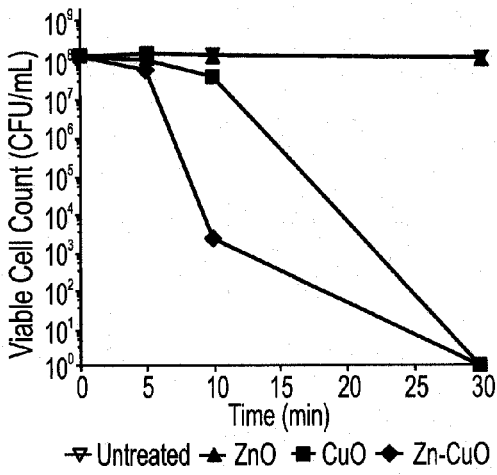

As shown in Table 4, and is further illustrated in the viability curves in FIG. 17C for MRSA, and in FIG. 17D for MDR *E. coli*, the Zn-doped CuO nanoparticles exhibited more pronounce antibacterial effect than that of the CuO and ZnO nanoparticles: For MRSA, complete killing was already evident in the Zn-doped CuO nanoparticles coating after 10 minutes, whereas the CuO nanoparticles coating exhibited only 3 logs of CFUs reduction, and the ZnO nanoparticles coating exhibited only one log reduction in CFUs after 10 minutes.

Table 4 and the viability curves in FIG. 17D for MDR *E. coli*, further show that while a complete killing of MDR *E. coli* was achieved after 30 minutes by both Zn-doped CuO nanoparticles and CuO nanoparticles coatings, with the Zn-doped CuO nanoparticles coating the CFUs were reduced by 5 logs after a short treatment of 10 minutes, while the CuO nanoparticles coating exerted only a tiny antibacterial effect in this time duration.

Table 5 shows antibacterial activity of fabrics coated with Zn-doped CuO nanoparticles as examined against the *P. acne*.

TABLE 5

| Treatment time (hours) | CFU/ml |
|---|---|
| 0 | $1.2 \times 10^6$ |
| 3 | $1 \times 10^4$ |

The results showed that a 3 hours incubation with Zn-doped CuO coated fabrics resulted in elimination of more than 99% of acne bacteria.

P. acnes is another example of MDR bacteria, since 40% of P. acnes that cause skin wounds are resistant to commonly used topical and oral administrated antibiotics. It is therefore clear that data presented herein, are of highest important introducing a new source for producing new principles, new techniques and new methods which can be utilized against multidrug resistant bacteria.

Figure 18:
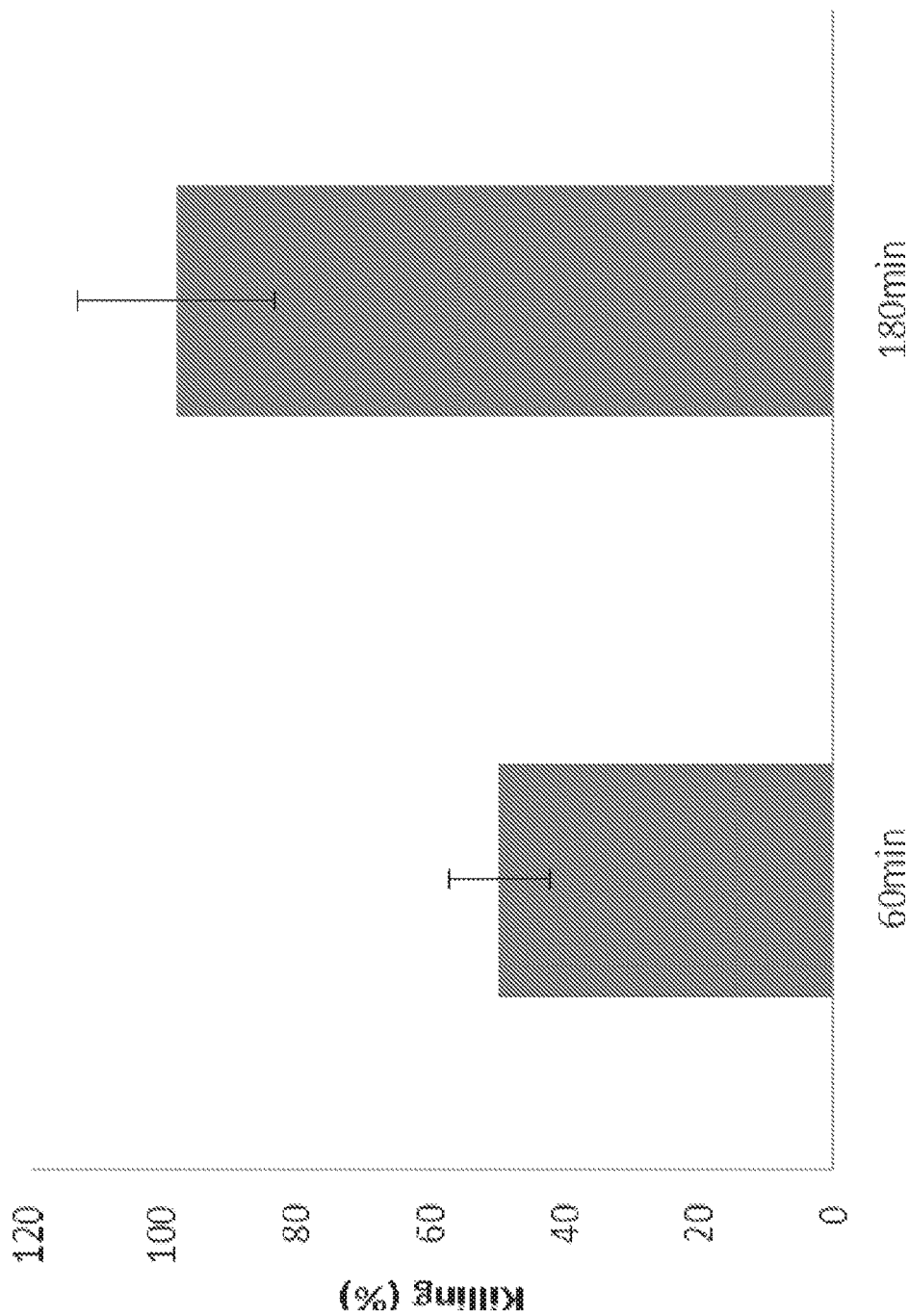
FIG. 18 is a bar graph showing the percentage of killed *Candida albicans* upon contacting a fabric coated with Zn-doped CuO for 60 minutes and 180 minutes in nutrient broth (NB) medium (error bars represent standard deviation of uncertainty).

FIG. 18 shows a bar graph presenting antifungal killing rate upon treatment of fabric coated with Zn-doped CuO nanoparticles, showing about 50% reduction in Candida albicans cells after 60 minutes and almost 100% reduction after 180 minutes of treatment.

Figure 19A:
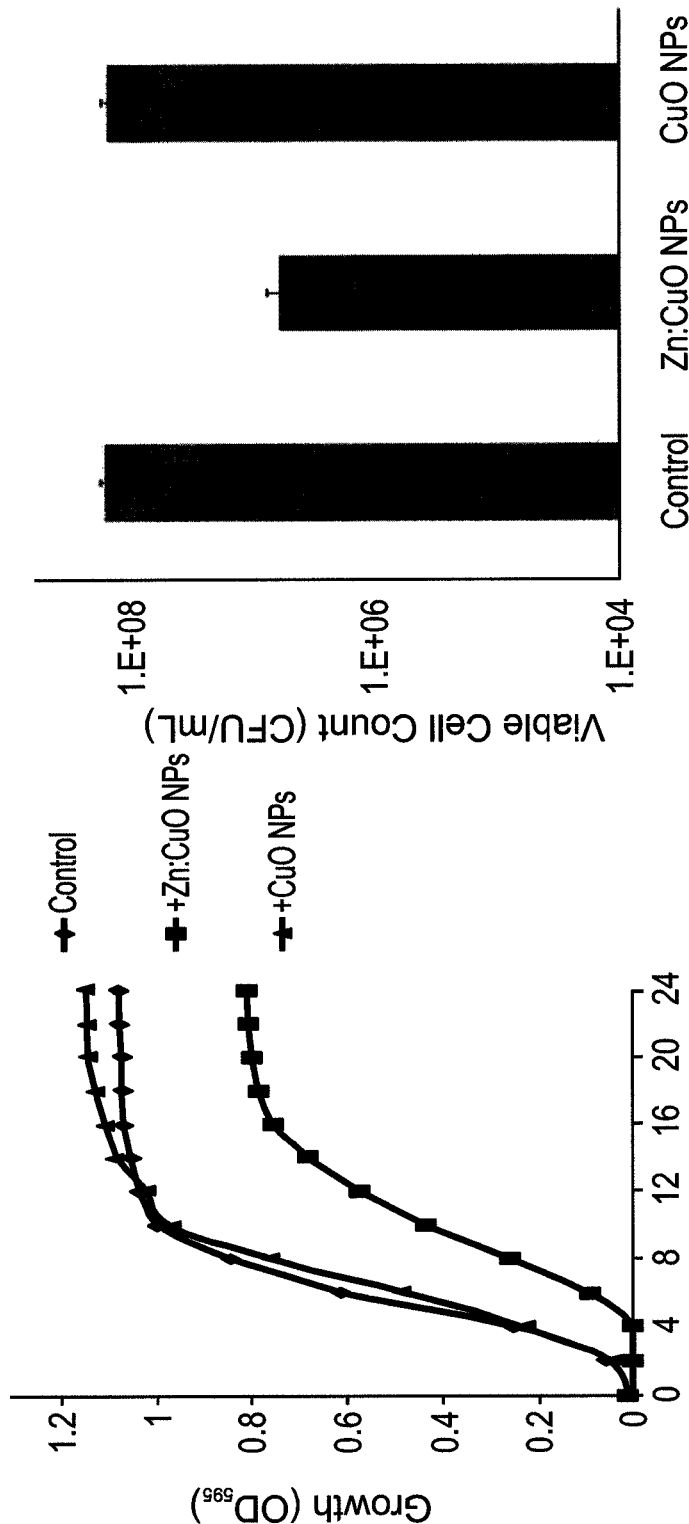
FIGS. 19A-B present comparative plots showing bacterial growth (FIG. 19A) and a bar graph (FIG. 19B), showing viability of *Streptococcus mutans* in the presence of suspensions Zn-doped CuO nanoparticles, and CuO nanoparticles compared with untreated bacteria-containing saline medium (control) (FIG. 19A), (error bars represent standard deviation of uncertainty).

FIG. 19A present growth curves showing that free CuO nanoparticles did not affect the growth of S. mutans and further showing that Zn-doped CuO nanoparticles delayed the bacterial growth.

Figure 19B:

As shown in FIG. 19B, in the Zn-doped CuO nanoparticles suspension, the viability of the S. mutans after 24 hours fits to $1.7 \times 10^8$ CFU/ml compared to $6.3 \times 10^6$ CFU/ml for the untreated bacteria control, whereas CuO nanoparticles treatment did not result in a significant decrease in the bacterial viability. The ANOVA test confirmed the significance of the differences ($F_{(2,6)}=171.56$, $p<0.001$).

Figure 20:
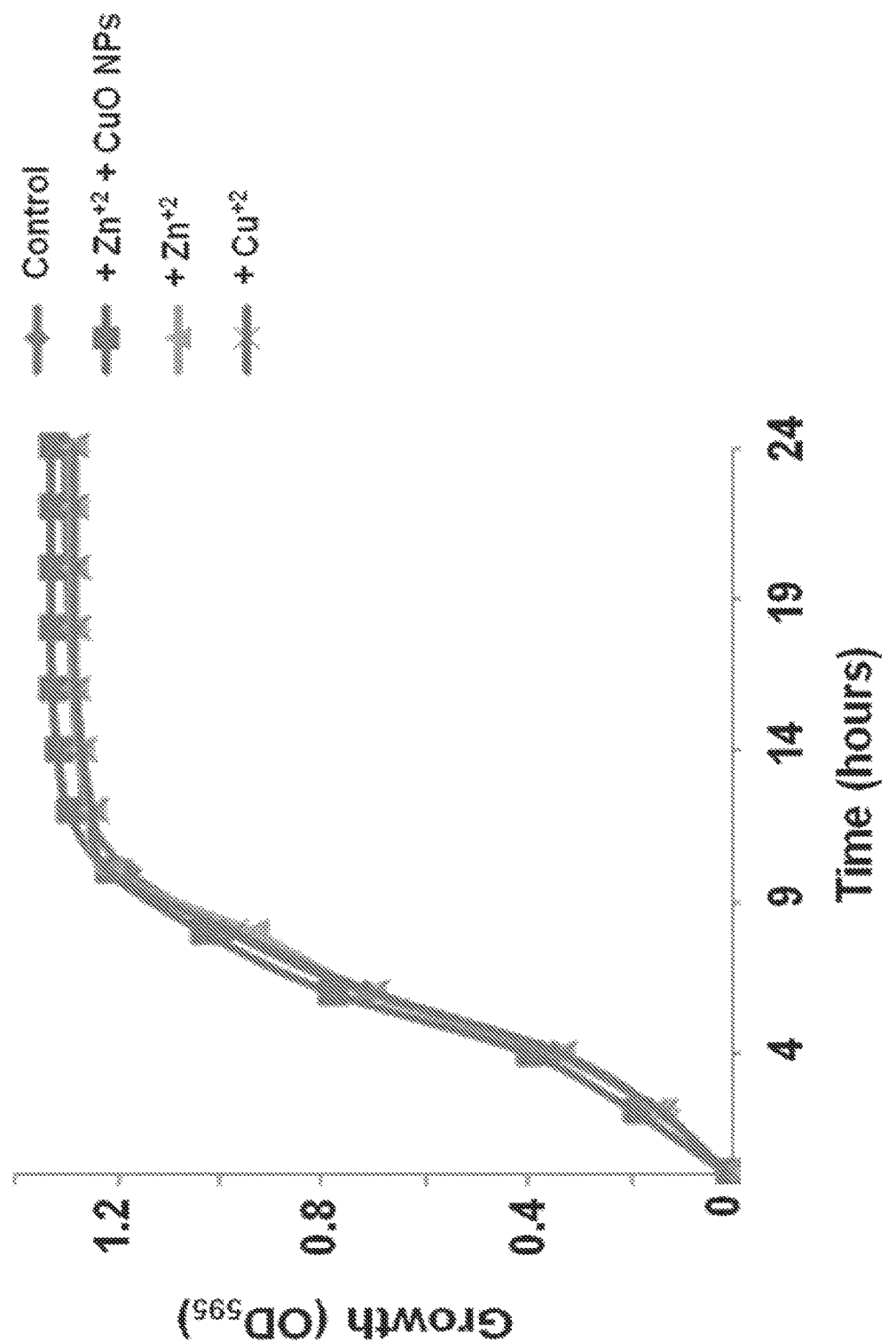
FIG. 20 presents comparative plots showing the growth of *S. mutans* in Brain-Heart (BH) media for 24 hours in the presence of CuO nanoparticles and Zn$^{2+}$, Cu$^{2+}$ ions or Zn$^{2+}$ ions, wherein the ions are at their saturated concentrations in BH (error bars represent standard deviation of uncertainty).

FIG. 20 presents the growth curves of S. mutans in media inoculated with either $Cu^{2+}$ or $Zn^{2+}$ ions at their corresponding concentrations as presented in Table 2 hereinabove over a period of 24 hours, showing no antibacterial effect.

As further shown in FIG. 20 the absence of the antibacterial effect was further demonstrated in the CuO nanoparticle suspension (1 mg/ml) inoculated with $Zn^{2+}$ ions at their corresponding concentration as presented in Table 2 for ZnO.

Figure 21:
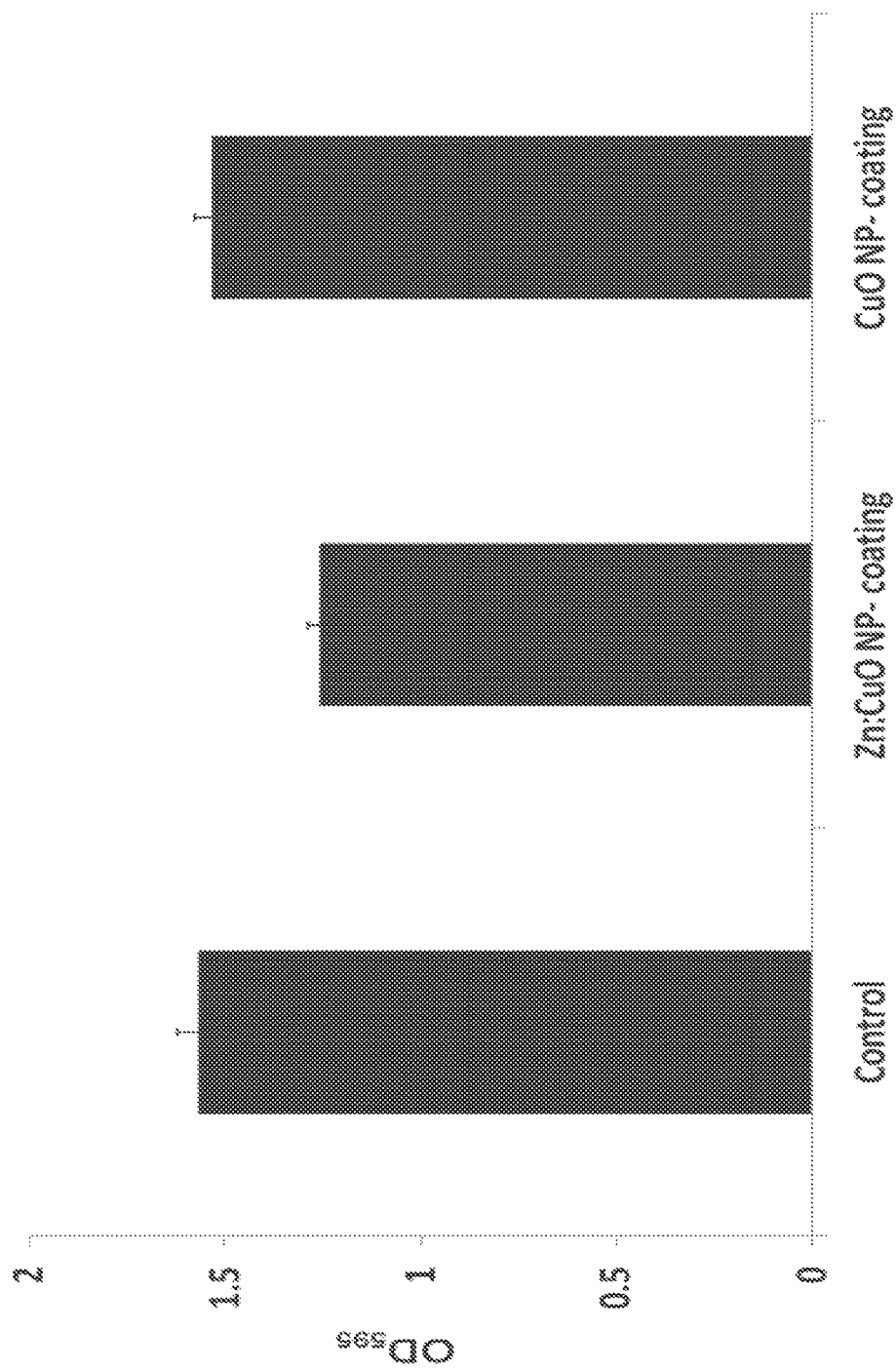
FIG. 21 is a bar graph showing the effect of coating an artificial tooth with Zn-doped CuO nanoparticles, and CuO nanoparticles, compared with uncoated teeth (control), on *S. mutans* growth in Brain-Heart (BH) media.

As shown in FIG. 21 an artificial tooth coated with CuO nanoparticles did not affect the S. mutans growth, whereby the Zn-doped CuO nanoparticles coating reduced the growth of S. mutans compared to the control of untreated bacteria. The ANOVA tests confirmed the significance of the differences in the bacterial growth behavior ($F_{(2,6)}=47.66$, $p<0.001$). A post-hoc Scheffe test on data for the bacterial growth further indicated that there was no significant difference between the control (M=1.56, SD=0.06) and CuO (M=1.55, SD=0.04), whereas the Zn-doped CuO nanoparticles (M=1.26, SD=0.32) was significantly lower than the control.

Figure 22:
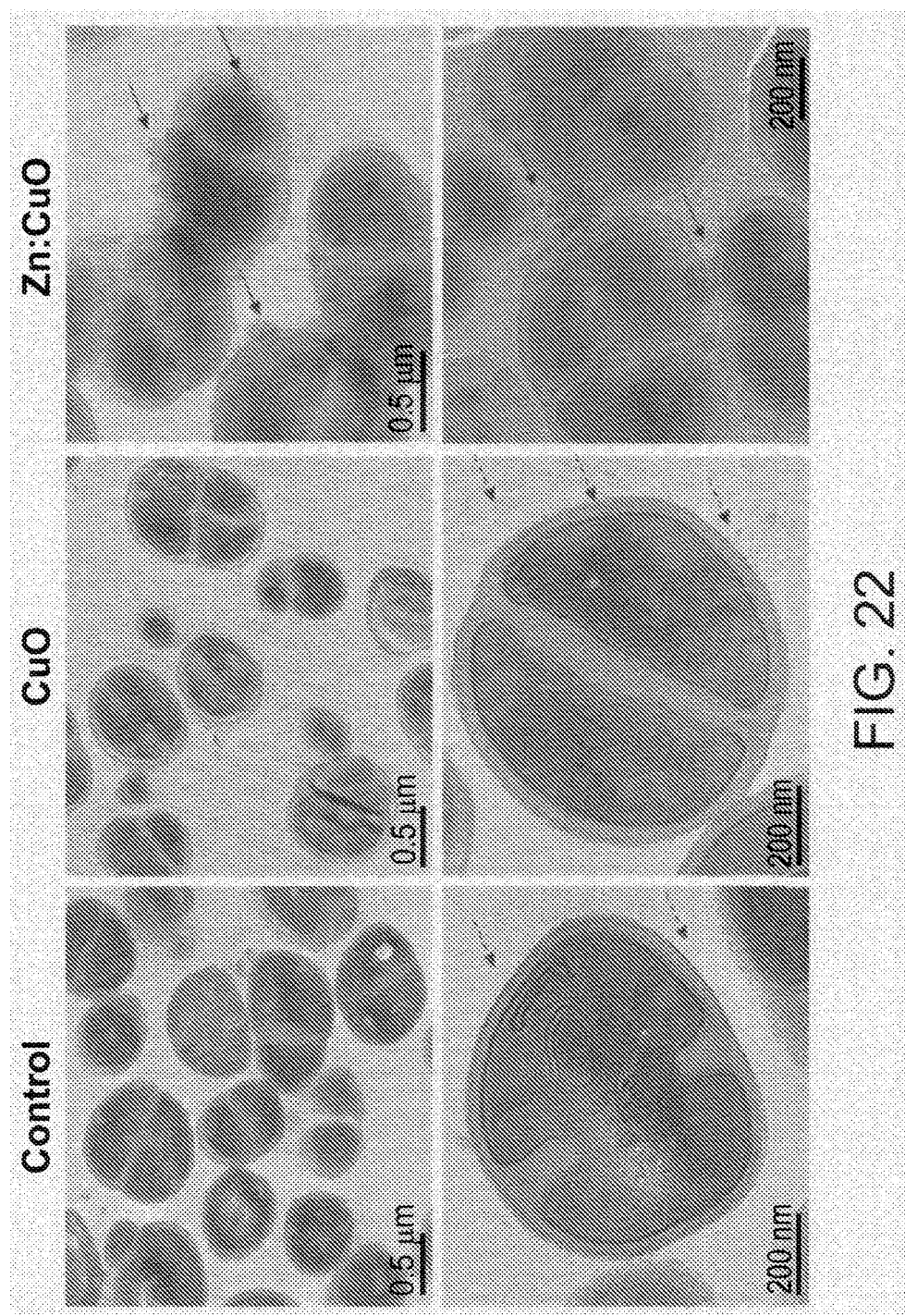
FIG. 22 presents TEM images showing the morphological changes in *S. mutans* cells, upon treatment with CuO nanoparticles, and with Zn-doped CuO nanoparticles, compared to control untreated cells, at a scale bar of 0.5 micron (upper panel) and 200 nm (lower panel), with arrows marking the cell surface or the cell membrane of the bacterial cells.

FIG. 22 presents TEM images exhibiting the morphological changes to S. mutans cells, following treatment with CuO nanoparticles or Zn-doped CuO nanoparticles, and further exhibiting the presence of the Zn-doped CuO nanoparticles localized either on the cell surface or within the cell membrane.

As shown in FIG. 22, the cell membrane, upon treatment with Zn-doped CuO nanoparticles, appeared to be damaged and disorganized, whereas in the case of treatment with the CuO nanoparticles, the cell membrane remained intact, without visible injury.

For comparison, TEM images exhibiting normal untreated cell morphology of S. mutans cells are further presented in FIG. 22 showing distinct cell walls and membrane structures typical of uninjured Gram-positive bacteria.

Table 6 below presents ICP data of the intracellular level of Cu and Zn following the exposure of the S. mutans cells to Zn-doped CuO nanoparticles.

As shown in Table 6 the exposure of the bacterial cells to Zn-doped CuO nanoparticles resulted in a dramatic increase in Cu within the cells compared to the exposure to CuO nanoparticles. The ratio between Cu and Zn was very close to 8:1, further supporting the internalization of the Zn-doped CuO nanoparticles characterized with this ratio.

TABLE 6

| | $[Cu^{+2}]$ µg/L | $[Zn^{+2}]$ µg/L |
|---|---|---|
| S. mutans | 5 | — |
| S. mutans + Zn—CuO nanoparticles | 327.6 | 42.86 |
| S. mutans + CuO nanoparticles | 19.9 | — |

Figure 23:
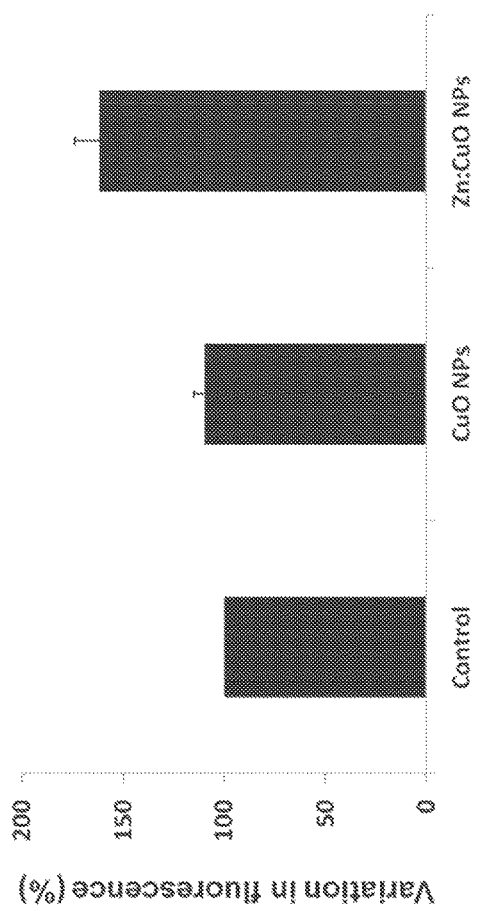
FIG. 23 is a bar graph showing the variation of fluorescence intensity in *S. mutans* cell samples upon treatment with the CuO nanoparticles and with Zn-doped CuO nanoparticles, compared to untreated samples (control) (error bars represent standard deviation of uncertainty).

FIG. 23 presents bars demonstrating the fluorescence intensity in the treated S. mutans cell samples compared to untreated samples (control).

As shown in FIG. 23 there is a slight increase in the ROS concentration in the cells treated with the CuO nanoparticles compared to the untreated control.

As can be further seen in FIG. 23 a more predominant effect of increase in the ROS concentration was observed for the cells treated with the Zn-doped CuO nanoparticles, whereby the emitted fluorescence was increased by approximately 62% relative to the untreated control.

Statistical analysis indicated a significant difference ($F_{(2,6)}=45.05$, $p<0.001$); post-hoc Scheffe test results indicated a significantly higher value for Zn-doped CuO (M=161.83, S.D=12) than the control (M=100, S.D=0) and CuO (M=110, S.D=8.7)

Figure 24:
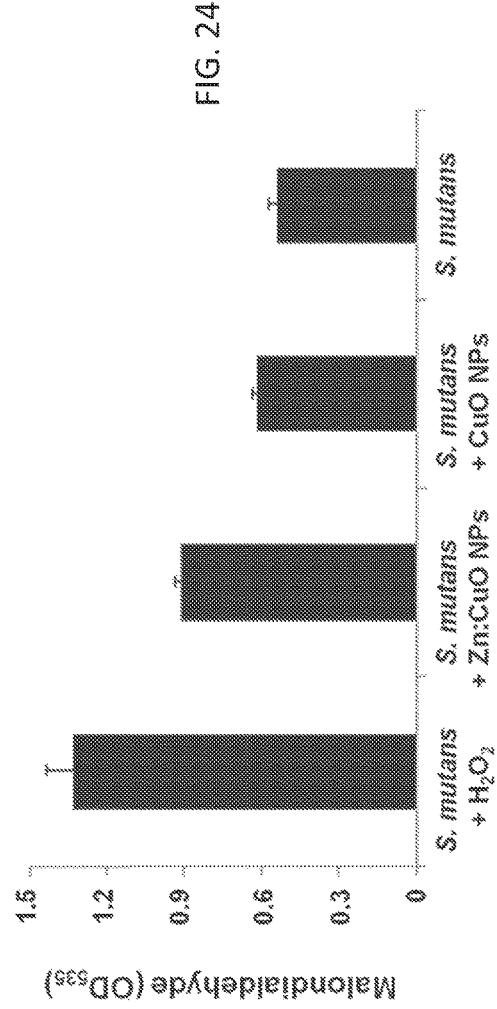
FIG. 24 is a bar graph showing the effect of Zn-doped CuO nanoparticles, CuO nanoparticles, and H$_2$O$_2$ (1 mM) on malondialdehyde (MDA) concentration in *S. mutans* samples compared with untreated samples (control) (error bars represent standard deviation of uncertainty).

As shown in FIG. 24, the addition of Zn-doped CuO nanoparticles increased the MDA concentration in the cells to a level that was higher than the amount produced by the same concentration of CuO.

A one-way ANOVA was performed for the samples, and the results indicated a significant difference ($F_{(3,8)}=111.18$, $p<0.001$). A post-hoc Scheffe test indicated a significantly higher value for $H_2O_2$ control (M=1.33, SD=0.11) than S. mutans alone (M=0.53, SD=0.04) and S. mutans+CuO nanoparticles (M=0.62, SD=0.02) and S. mutans+Zn-doped CuO nanoparticles (M=0.91, SD=0.03). The value for S. mutans+Zn-doped CuO nanoparticles was significantly higher than the untreated S. mutans control and S. mutans+CuO nanoparticles. There was no significant difference between S. mutans and S. mutans+CuO nanoparticles.

Example 5

Anti-Biofouling Assays

Antibiofouling Flow Cell Tests:
Catheter Flow Cell Model:

To test coated catheters the flow cell system was established. The system consists of several parts: (1) 2 L media bottle containing 1% of Muller-Hinton (MH) II Broth Cation-Adjusted, (2) peristaltic pump that supplies the fresh media from the bottle at a defined rate, (3) bubble trap, (4) flow chamber or any other interface in which the bacteria can form biofilm (5) waste bucket, to which the media and bacterial waste is excluded. The system is connected by silicone tubing. 4 cm length fragments of the coated catheters where connected through the silicone tubing.

Bacteria were grown overnight in Muller-Hinton, Bacterial growth was quantified by OD of 595 nm measurement and then diluted to fresh bacterial culture with $3 \times 10^8$ bacteria. This culture was injected into the catheter using a sterile syringe and incubated for 2.5 hours at 37° C. Afterwards, the catheter was connected to the flow cell system.

The pump was set to 2 rpm and the fluid flow in the system was accordingly. The experiment was done at 37° C., for 24 hours. The bacteria where removed from the catheter by mechanical scraping into 1 ml of sterile saline. The viable bacteria were estimate by counting the number of colony-forming units (CFU) on Luria Broth (LB) agar plates.

*Escherichia coli* ATCC 25922, *Staphylococcus aureus* ATCC 29213 and *Proteus mirabilis* (Bar Ilan University Bacteriology Lab Strain Collection) were grown in Mueller Hinton (MH) II Broth Cation-Adjusted (BD) media at 37° C. for 15-17 hours. Bacterial growth was quantified by OD of 595 nm measurement and then diluted to the appropriated density. 1 ml of MH with 99 ml of ddH$_2$O used as the operational solution for the catheters experiments. Catheters (Degania Silicone Ltd) are 100% Silicone and in scale of 8 French and were cut into 4 cm length fragments for flow cell experiments.

Flow Cell Assays:

In exemplary procedures Biofilm formation on a substrate (e.g, glass slide,) coated with either CuO nanoparticles, ZnO nanoparticles, or Zn-doped CuO nanoparticles was assayed.

In exemplary procedures to test coated glass slides the biofilm system was composed of a polycarbonate chamber into which the tested glass slides (coated and uncoated) were inserted. Using a Watson Marlow peristaltic pump and silicon manifold tubing (0.8 mm diameter), the growth medium was pumped at a constant rate (10 ml/hour) through the chamber.

The flow cell was initially inoculated with a 0.3 OD$_{595}$ cell culture of the bacteria (e.g., *E. coli* 1313 and *S. aureus* 195). The flow was initiated after 1 hour of incubation at room temperature (flow rate of 10 ml/hour), and 1% TSB or 1% TSB-Glu (BD Biosciences) (diluted in ddH$_2$O) was used as a growth medium for each bacterial strain, After several days (i.e., 7, 15) the coated substrates were removed from the experimental flow cell and washed with DDW to remove nonattached cells. For imaging, slides were stained using the Live/Dead BacLight kit (Molecular Probes, Invitrogen, manufacturer protocol). A SYTO9/propidium iodide (Molecular Probes, Invitrogen, manufacturer protocol) mixture stain was dissolved in a mixture of 3% DMSO and ddH$_2$O (15 minutes incubation). Viable bacteria with intact cell membranes are stained in green, whereas dead bacteria with damaged membranes are stained in red. Both excitation/emission maxima for these two dyes are 480/500 nm for the SYTO9 stain, and 490/635 nm for the propidium iodide. Biofilm formation was monitored using a confocal scanning laser microscope (Leica SPE, San Diego, Calif., United States). Obtained images were further processed by the Imaris Image Analysis software (Imaris v.6.0, Bitplane Scientific Software) and represent the general trend seen in three independent experiments. The images obtained were used to determine the biofilm biomass using the PHLIP software which provides the bio-volume of the biofilm. Alternatively, glass slides washed with ddH$_2$O and the biofilm cells were detached by exposure to low energy sonication water bath (TRANSSONIC 460, ELMA) for 1 minute and centrifuged at 4000 rpm for 5 minutes to form pellet cells. Cells were re-suspended and serial dilutions were plated on LB-agar plates to enumerate the viable cells. The experiment was conducted in triplicate and was repeated three times independently.

Static Antibiofilm Assays:

A coated substrate (e.g., artificial tooth) was placed in a 24-well plate (Greiner Bio-One); each well contained a 3 ml bacterial suspension (e.g., of *S. mutans*) at a final concentration of OD$_{595}$=0.15 (approximately 1.5×10$^8$ CFU/ml) in BH medium. After incubating for 24 h at 37° C., the teeth were washed twice with ddH$_2$O to remove the nonattached cells, and the biofilm biomass was stained with 1% crystal violet (CV, Sigma-Aldrich) for 15 minutes at room temperature (i.e. about 25° C.). The stained biofilm that formed on the tooth was washed five times with ddH$_2$O, and the remaining CV was eluted with absolute ethanol for 15 minutes. The biofilm biomass was then determined by measuring the absorbance at OD$_{595}$.

Morphological Examination:

In exemplary procedures for examining the biofilm morphology, the coated substrate was exposed after incubation to Karnovsky's fixative (glutaraldehyde+paraformaldehyde (Sigma-Aldrich) for 1 hour. The sample was washed three times with phosphate-buffered saline (PBS) which does not contain Ca$^{2+}$ and Mg$^{2+}$ ions. The samples were immersed for 1 hour in a mixture of titanic acid and a glutamate solution in a 4:5 concentration ratio (Sigma-Aldrich). After three cycles of washing with the PBS, the sample was exposed to an osmium tetraoxide solution (Sigma-Aldrich) for 1 hour. Lastly, the residual water was removed with water-ethanol and ethanol-freon solutions (from 50% to 100% of each solvent) (Sigma-Aldrich). The samples were then dried in air, carbon-coated, and imaged by HR-SEM (JEOL-6700F, accelerating voltage of 15 kV). Statistic analysis was further performed (a one-way analysis of variance (ANOVA) and post-hoc Scheffe test) to validate the significance of the results.

Results

Antifouling Flow Cell Tests

FIGS. 25A-C present diagrams showing the enhanced antifouling activity of Zn-doped CuO nanoparticle coated catheter against the urinary tract pathogens: *E. coli* (FIG. 25A) *S. aureus* (FIG. 25B) and *P. mirabilis* (FIG. 25C).

Flow Cell Assays: Antibiofilm Tests:

As shown in FIG. 26 the Zn-doped CuO nanoparticles-coated glass slides were able to almost completely restrict both *E. coli* (FIG. 26A) and *S. aureus* (FIG. 26B) biofilm formation throughout the entire 15 days and were significantly more active than the ZnO and CuO coatings. The biofilm images obtained by the confocal microscope were used to determine the biofilm biomass using the PHLIP software which provides the bio-volume of the biofilm.

Figure 27:
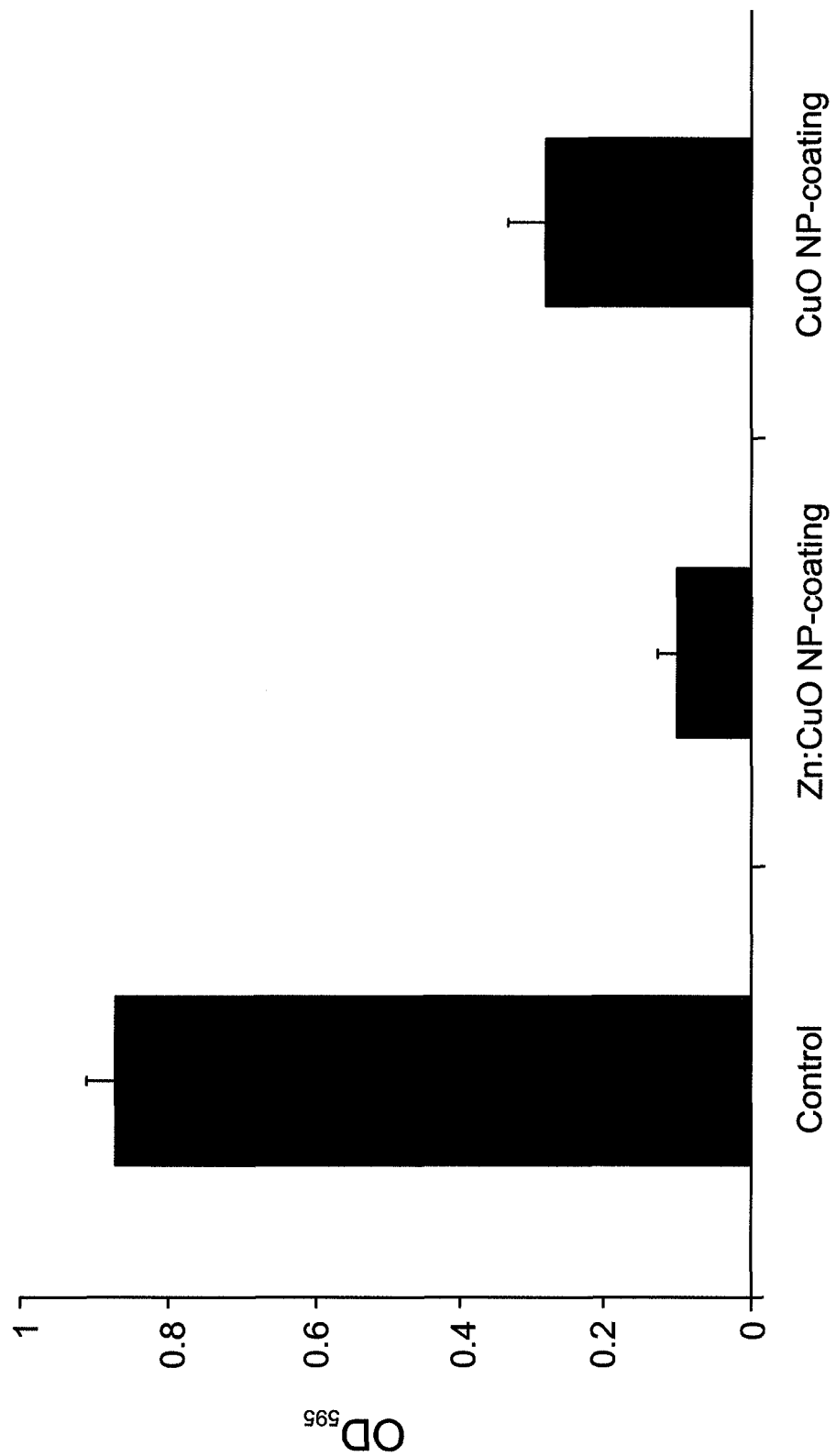
FIG. 27 is a bar graph presenting the biofilm biomass quantification of *S. mutans* formed on an uncoated artificial tooth substrate (control) and on teeth coated with either CuO nanoparticles or Zn-doped CuO nanoparticles (error bars represent standard deviation of uncertainty).

Static Antibiofilm Assays:

FIG. 27 shows the antibiofilm activity of on artificial teeth coated with either Zn-doped CuO nanoparticles or CuO nanoparticles with the reduction of the biofilm formation by 88% and 70%, respectively, compared to a massive biofilm on the uncoated tooth (control). The Statistical test ANOVA further confirmed the significant difference in the biofilm formation reduction ($F_{(2,6)}$=336.32, p<0.001). Post-hoc Scheffe statistical test confirmed that the biofilm was significantly smaller for the Zn-doped CuO coating ([M]=0.1, standard deviation [S.D]=0.24); Control (M=0.87, S.D=0.04); CuO coating (M=0.29, S.D=0.05).

Figure 28:
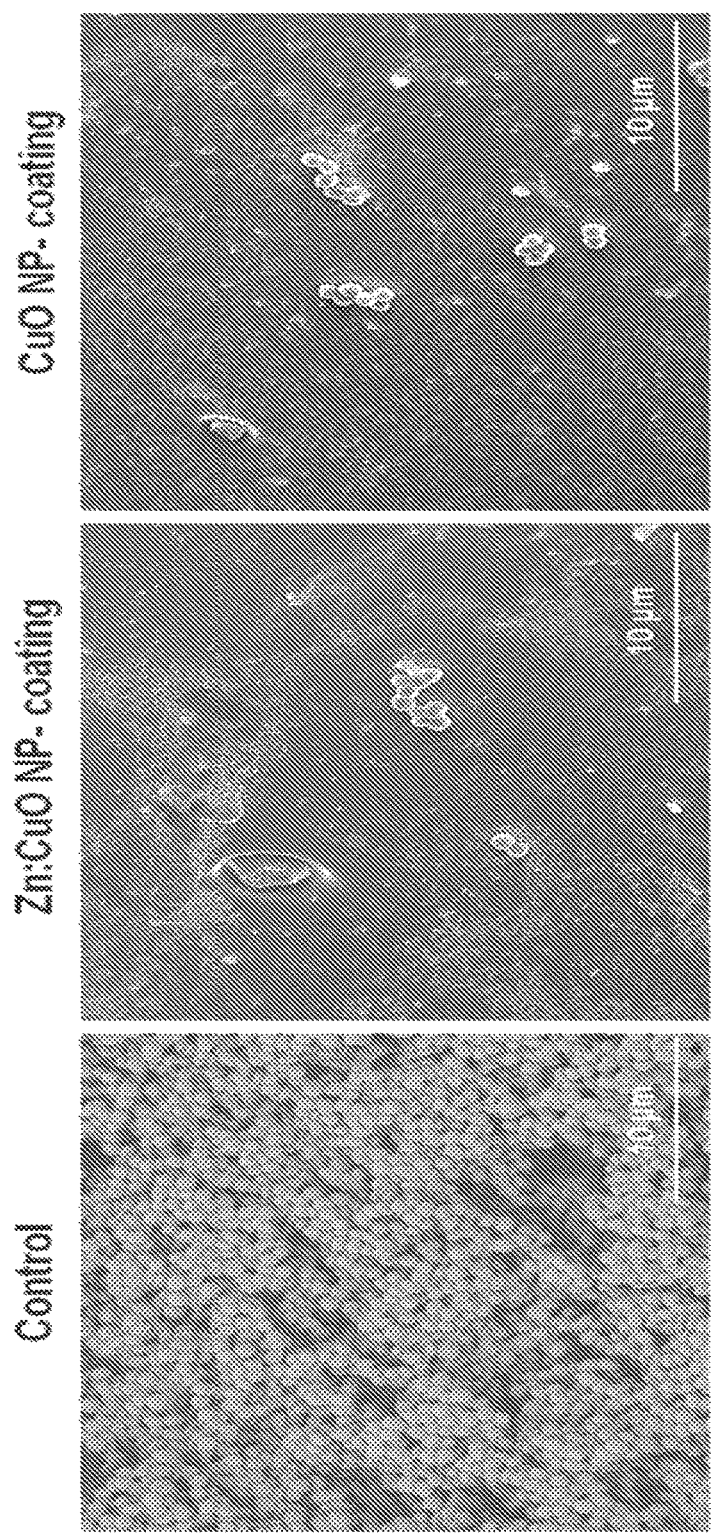
FIG. 28 present HRSEM images showing the morphological changes of *S. mutans* biofilm on a tooth coated with CuO nanoparticles, tooth coated with Zn-doped CuO nanoparticles, vis a vis the control of biofilm formation on a bare tooth.

Morphological Examination:

FIG. 28 presents HRSEM images, demonstrating that no *S. mutans* biofilm formation was observed on the artificial teeth coated with Zn-doped CuO nanoparticles and CuO nanoparticles.

Example 6

In-Vivo Efficacy Study and Biocompatability Assays

Materials and Experimental Methods

The experiments below were performed on extracts obtained from the pediatric silicon urinary catheter following a three-day incubation in saline solution (for the irritation test, TEVA)) and in growth medium L929 (contains: EMEM without phenol red (Gibco, Cat #51200-046) supplemented with 10% Fetal Bovine Serum (FBS, Cat #04-001-1), 4 mM L-glutamine, 100 U/ml Penicillin, 100 µg/ml Streptomycin) for the MTT test. The extract was then used in the relevant assay.

Irritation Tests:

In vitro eye irritation hen's egg test chorioalantoic membrane (HET-CAM) was performed using white Leghorn fresh fertile eggs.

In exemplary procedures, fertilized hen's eggs were rotated in an incubator for 8 days, thereafter rotation was stopped for one day. On the 10th day the shell around the air chamber was removed and the inner membranes were extracted to reveal the chorionallantoic membrane. Each of the test devices extracts: Zn-doped CuO nanoparticles coated catheter, positive controls (sodium hydroxide (NaOH 0.1M) and extracted vehicle control and negative control (0.9% sodium chloride (Saline) for intravenous injection) was applied on the membrane and left in contact for 5 minutes. The membrane was examined for vascular potential damage (Hemorrhage, Vascular Lysis & Coagulation). The time taken for injury to occur was recorded during the 5 minutes of observation. Irritancy was scored according to the duration at which damage occurs.

In Vitro Cytokine Secretion Tests:

The objective of this study is to assess the potential of leachable substances in extracts of test devices.

In exemplary procedures the test was applied on uncoated catheter and Zn-doped CuO nanoparticles coated catheter to induce cytokine secretion in mouse splenocytes. Cytokine levels were analyzed using Quansys Q-Plex Array Chemiluminescent kit. Each Test Device extract was further diluted with growth medium to dilutions designated as: 100%, 85%, 75%, 50%, 25% and 12.5%. Vehicle control's extract was applied non-diluted (100%). The positive control, Lipopolysaccharides (LPS) which is known as proliferative agent was dissolved with water, cell culture grade, to achieve a stock solution of 2000 µg/ml. Stock solution was further diluted 1:1000 with PBMCs (RPMI Medium supplemented with 10% Heat Inactivated FBS (Fetal Bovine Serum), 2 mM L-Glutamine, 1% non-essential amino acids, 100 U/ml Penicillin and 100 µg/ml Streptomycin) growth medium to achieve final concentration of 2 µg/ml.

The IL-12p70, IL-6, IL-1-β, MIP-1-α, TNF-α and IL-10 cytokines levels were determined following 22 hours of incubation using Quansys Q-Plex™ Array Chemiluminescent kit, according to the manufacture's instruction. The samples were tested as undiluted.

In Vivo Studies:

The feasibility of the Zn-doped CuO nanoparticles coated catheter to prevent the potential catheter-associated urinary tract infection and biofilm formation in the New Zealand white (NZW) male rabbit was assessed.

In exemplary procedures the exposure to the indwelling urinary catheters period lasted 7 successive days. Each Test Device-treated group was subjected to urethral catheterization with the respective coated indwelling urinary catheter and an additional equally sized group, subjected to urethral catheterization with the uncoated indwelling urinary catheter under identical experimental conditions, served as the control device group. All the groups in the study comprised n=5 animals/group, total of 15 rabbits in the study. All the animals were euthanized on the 7th day post the urethral catheterization, and following collection of the last urine sample, for macroscopic and microscopic examinations.

Results

Irritation Tests:

FIG. 29 show representative images of the CAM blood vessels following the irritation treatments.

FIG. 29A presents an image of the CAM blood vessels following the treatment with intravenous injection of 0.9% (Saline), showing no irritating effect on the blood vessels under the CAM with calculated mean irritancy score of 0.

FIG. 29B presents an image of the CAM blood vessels following the treatment with positive control (0.1 M NaOH), showing irritation effect on the blood vessel under the CAM with calculated mean irritancy score of 19.2.

FIG. 29C shows image of the CAM blood vessels following treatment with uncoated catheter extracts showing non-irritant effect.

FIG. 29D shows an image of the CAM blood vessels following treatment with Zn-doped CuO coated catheter extracts showing non-irritant effect.

In Vitro Cytokine Secretion Tests:

FIGS. 30A-F show that the Zn-doped CuO coated catheter extraction did not induce any cytokines compared to the uncoated catheter.

In Vivo Studies

Table 7 shows mean group hematology values, determined in NZW rabbits following urethral catheterization with catheter, Zn—CuO-coated catheter or uncoated catheter at the end of a 7-Day exposure period to the indwelling urinary catheters. The tests presented therein demonstrate no in vivo cytotoxicity in the tested values following catheterization with either uncoated or Zn—CuO-coated catheter.

TABLE 7

| PARAMETER | Uncoated Catheter (Control Device) | | Zn—CuO-Coated Catheter (Test Device) | |
| --- | --- | --- | --- | --- |
| | Mean (n = 5) | ±SD | Mean (n = 5) | ±SD |
| WBC ($10^3$ CMM) | 10.3 | 1.16 | 9.1 | 2.32 |
| RBC ($10^6$ CMM) | 5.85 | 1.110 | 5.37 | 1.195 |
| HGB (g/dl) | 11.9 | 2.43 | 11.1 | 2.51 |
| HCT (%) | 37.1 | 7.22 | 34.5 | 7.65 |
| MCV (fL) | 63.3 | 1.51 | 64.2 | 2.05 |
| MCH (PG) | 20.3 | 0.64 | 20.7 | 0.76 |
| MCHC (g/dl) | 32.0 | 0.35 | 32.2 | 0.28 |
| Platelets ($10^3$ CMM) | 648 | 121.4 | 709 | 125.2 |
| Neutrophils (%) | 53 | 3.6 | 45 | 7.1 |
| Stab (%) | 0 | 0.0 | 0 | 0.0 |
| Lymphocytes (%) | 40 | 3.3 | 47 | 7.1 |
| Monocytes (%) | 3 | 1.3 | 4 | 2.0 |
| Eosinophils (%) | 1 | 0.2 | 1 | 0.1 |
| Basophils (%) | 2 | 0.5 | 2 | 0.8 |

Table 8 presents mean group biochemistry values, determined in NZW Rabbits following urethral catheterization with catheter Zn—CuO-coated catheter or uncoated catheter at the end of a 7-day exposure period to the indwelling urinary catheters. The tests presented therein demonstrate no in vivo cytotoxicity in the tested values following catheterization with either uncoated or Zn—CuO-coated catheter.

Similar findings of no cytotoxicity were observed in macroscopic findings during urinary tract dissection in NZW Rabbits following urethral catheterization with Zn—CuO-coated catheter (Batch No. 07-13-Zn—CuO) and throughout an exposure period of 7 successive days to the indwelling urinary catheters (data not shown).

TABLE 8

| PARAMETER | Uncoated Catheter (Control Device) | | Zn—CuO-Coated Catheter (Test Device) | |
|---|---|---|---|---|
| | Mean (n = 5) | ±SD | Mean (n = 5) | ±SD |
| Creatinine (mg/dl) | 1.08 | 0.175 | 1.27 | 0.404 |
| Urea (mg/dl) | 37.2 | 8.50 | 41.4 | 18.51 |
| Potassium = K (mEq/L) | 3.6 | 0.16 | 4.3 | 0.36 |
| Sodium = Na (mEq/L) | 142 | 1.1 | 144 | 1.3 |
| Chloride = Cl (mEq/L) | 100 | 2.7 | 100 | 1.8 |
| Total Protein (g/dl) | 5.40 | 0.138 | 5.09 | 0.184 |
| Albumin (g/dl) | 2.11 | 0.686 | 2.41 | 0.255 |
| Globulin (g/dl) | 2.89 | 0.053 | 2.60 | 0.108 |
| AST = SGOT (IU/L) | 21 | 9.0 | 24 | 9.6 |
| ALT = SGPT (IU/L) | 42 | 7.4 | 35 | 17.9 |
| ALP (IU/L) | 51 | 41.4 | 22 | 3.0 |
| GGTP (IU/L) | 7 | 2.4 | 6 | 1.2 |
| Total Bilirubin (mg/dl) | 0.04 | 0.008 | 0.04 | 0.008 |
| Cholesterol (mg/dl) | 45 | 8.5 | 41 | 6.8 |
| TRIG (mg/dl) | 54 | 20.4 | 51 | 18.5 |
| Calcium (mg/dl) | 12.67 | 0.303 | 12.86 | 0.531 |
| Phosphorus (mg/dl) | 5.0 | 0.30 | 5.2 | 0.52 |
| Glucose (mg/dl) | 141 | 12.7 | 125 | 13.5 |
| CPK (IU/L) | 2236 | 1151.2 | 1232 | 677.4 |
| LDH (IU/L) | 168 | 39.3 | 156 | 46.2 |
| Albumin/Globulin ratio | 0.86 | 0.058 | 0.99 | 0.075 |
| BUN (mg/dl) | 17 | | | |

***↑ $P < 0.01$ vs. the Control Device (One-Way ANOVA, Dunnett Multiple Comparisons Test)

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising at least one nanoparticle composite, said at least one nanoparticle composite comprising a metal oxide and ions of a metallic element included in a crystal lattice of said metal oxide, wherein said metal oxide is copper oxide and said metallic element is zinc.

2. The composition-of-matter of claim 1, wherein an atomic ratio of said metal oxide and said ions of said metallic element in said at least one nanoparticle composite ranges from 10:1 to 4:1.

3. The composition-of-matter of claim 1, being prepared by subjecting a mixture of a first and a second metal precursor to high intensity ultrasonic irradiation, wherein said first metal precursor forms said metal oxide and said second metal precursor comprises said metallic element.

4. The composition-of-matter of claim 1, characterized by an X-Ray Powder Diffraction which is devoid of peaks at positions that correspond to a pristine metal oxide of said metallic element.

5. The composition-of-matter of claim 4, characterized by an X-Ray Powder Diffraction exhibiting at least one peak at a position and/or width that is different from a position and/or width of a corresponding peak in an X-Ray Powder Diffraction of said metal oxide.

6. The composition-of-matter of claim 1, characterized by a crystal lattice exhibiting at least one cell parameter that is different from a corresponding cell parameter of a pristine crystal lattice of said metal oxide.

7. The composition-of-matter of claim 6, wherein said cell parameter is different from a corresponding cell parameter of a pristine crystal lattice of said metal oxide by at least 0.005.

8. A composition-of-matter comprising at least one nanoparticle composite, said at least one nanoparticle composite comprising a metal oxide and ions of a metallic element included in a crystal lattice of said metal oxide, said metal oxide being copper oxide and said metallic element being zinc, the composition-of-matter being characterized by at least one of:
   an X-Ray Powder Diffraction which is devoid of peaks at positions that correspond to a pristine metal oxide of said metallic element;
   an X-Ray Powder Diffraction exhibiting at least one peak at a position and/or width that is different from a position and/or width of a corresponding peak in an X-Ray Powder Diffraction of said metal oxide; and
   a crystal lattice exhibiting at least one cell parameter that is different from a corresponding cell parameter of a pristine crystal lattice of said metal oxide.

9. The composition-of-matter of claim 1, wherein said at least one nanocomposite structure is represented by the formula: $A_xB_yO$, wherein:
   A is said metallic element;
   B is a metal of said metal oxide;
   x and y are each independently a value of between 0.01 to 0.99, such that x+y=1.

10. The composition-of-matter of claim 1, comprising a plurality of said nanoparticle composites, wherein an average diameter of said nanoparticle composites is less than 300 nm.

11. The composition-of-matter of claim 1, further comprising a substrate, wherein a plurality of said nanoparticle composites is incorporated in and/or on at least a portion of said substrate.

12. The composition-of-matter of claim 11, wherein said substrate is or forms a part of an article.

13. The composition-of-matter of claim 12, wherein said article is selected from the group consisting of a medical device, a pharmaceutical, cosmetic or cosmeceutic product, a fabric, a bandage, a microelectronic device, a microelectromechanic device, a photovoltaic device, a microfluidic device, an article having a corrosivable surface, an agricultural device, a package, a sealing article, a fuel container and a construction element.

14. A process of preparing a composition-of-matter comprising at least one nanoparticle composite, said at least one nanoparticle composite comprising a metal oxide and ions of a metallic element included in a crystal lattice of said metal oxide, said metal oxide being copper oxide and said metallic element being zinc, the process comprising subjecting a mixture of a first and a second metal precursor to high intensity ultrasonic irradiation, wherein said first metal precursor forms said metal oxide and said second metal precursor comprises said metallic element.

15. The process of claim 14, wherein said mixture further comprises an aqueous solution.

16. The process of claim 15, wherein a concentration of each of said first and second metal precursors in said aqueous solution independently ranges from 0.005M to 0.5M.

17. The process of claim 14, wherein each of said first and second metal precursors is independently a water-soluble salt of said metal of said metal oxide and said metallic element, respectively.

18. The process of claim 14, wherein said irradiation is carried out using ultrasonic waves at a frequency of at least 20 kHz.

19. The process of claim 14, wherein said composition-of-matter further comprises a substrate and wherein a plurality of said nanoparticle composites is incorporated in and/or on at least a portion of said substrate, the process comprising contacting said substrate or a portion thereof with said mixture of said first and said metal precursors.

20. The process of claim 19, wherein said contacting is effected by immersing said substrate or a portion thereof in an aqueous solution which comprises said first and second metal precursors.

* * * * *